US006859271B1

(12) United States Patent
Carney et al.

(10) Patent No.: US 6,859,271 B1
(45) Date of Patent: Feb. 22, 2005

(54) PLATEN FOR AUTOMATIC SAMPLER

(75) Inventors: Christopher F. Carney, Wilmington, DE (US); Fred L. Ferguson, Wilmington, DE (US); John R. Reader, Newark, DE (US); Weidong Liu, West Chester, PA (US)

(73) Assignee: TA Instruments-Waters LLC, New Castle, DE (US)

( * ) Notice: Subject to any disclaimer, the term of this patent is extended or adjusted under 35 U.S.C. 154(b) by 625 days.

(21) Appl. No.: 09/796,751

(22) Filed: Mar. 2, 2001

Related U.S. Application Data

(60) Provisional application No. 60/264,021, filed on Jan. 26, 2001.

(51) Int. Cl.[7] .............................................. G01N 21/01
(52) U.S. Cl. ...................................................... 356/244
(58) Field of Search ............................ 356/244, 36–38, 356/614–640; 250/252, 491.1; 702/85, 94, 95, 150, 151

(56) References Cited

U.S. PATENT DOCUMENTS

| | | | |
|---|---|---|---|
| 3,456,490 A | | 7/1969 | Stone |
| 4,298,570 A | | 11/1981 | Lillig et al. |
| 4,322,216 A | | 3/1982 | Lillig et al. |
| 4,695,727 A | | 9/1987 | Brierley et al. |
| 4,757,437 A | | 7/1988 | Nishimura |
| 4,816,730 A | | 3/1989 | Wihelm, Jr. et al. |
| 5,215,377 A | | 6/1993 | Sugano |
| 5,215,923 A | | 6/1993 | Kinoshita et al. |
| 5,224,775 A | | 7/1993 | Reading et al. |
| 5,258,931 A | * | 11/1993 | Hassler, Jr. .................. 702/105 |
| 5,286,652 A | | 2/1994 | James et al. |
| 5,293,404 A | | 3/1994 | Takeda |
| 5,398,556 A | | 3/1995 | Lang |
| 5,483,843 A | | 1/1996 | Miller et al. |
| 5,721,384 A | | 2/1998 | Tanihata |

OTHER PUBLICATIONS

U.S. Appl. No. 09/767,903.
U.S. Appl. No. 09/796,748.
U.S. Appl. No. 09/796,750.
U.S. Appl. No. 09/796,733.
U.S. Appl. No. 09/796,749.
TA Instruments, Thermal Analysis and Rheology, catalog of products.
TA Instruments, Thermal Analysis and Rheology, Auto DSC System.
http:\\www.e-thermal.com\dsc204.htm Differential Scanning Calorimeter DSC Phoenix, Nov. 2000.
http:\\www.e-thermal.com\dsc204_asc.htm DSC 204 ASC the Automatic Sample Changer.
file://C:\temp\Instruments Home Products.htm As6 Autosampler for Pyris 6 Series Thermal Analyzers, Perkin Elmer Instruments, 1998–2000.
file://C:/Windows/temp\SeikoRobotics.htm EXSTAR6000 Seiko Robotics.
Differential Scanning Calorimetry for all Requirements, Mettler Toledo, Feb. 1996.

\* cited by examiner

*Primary Examiner*—Tu T. Nguyen
(74) *Attorney, Agent, or Firm*—Shaw Pittman LLP

(57) ABSTRACT

The invention relates to a platen to be used with a sample tray of an automatic sampler. According to an aspect, the platen includes both electrically conductive and reflective areas that can be used to calibrate the sample tray. According to another aspect, calibration of the sample tray can be performed in all three dimensions. According to another aspect, the platen is used to calibrate the sample tray, including its height and the location of its wells. The platen may include electrically-responsive (i.e., conductive) and optically-responsive (i.e., reflective) areas that can be sensed by electrical sensors and optical sensors in order to compute the coordinates of representative wells.

6 Claims, 68 Drawing Sheets

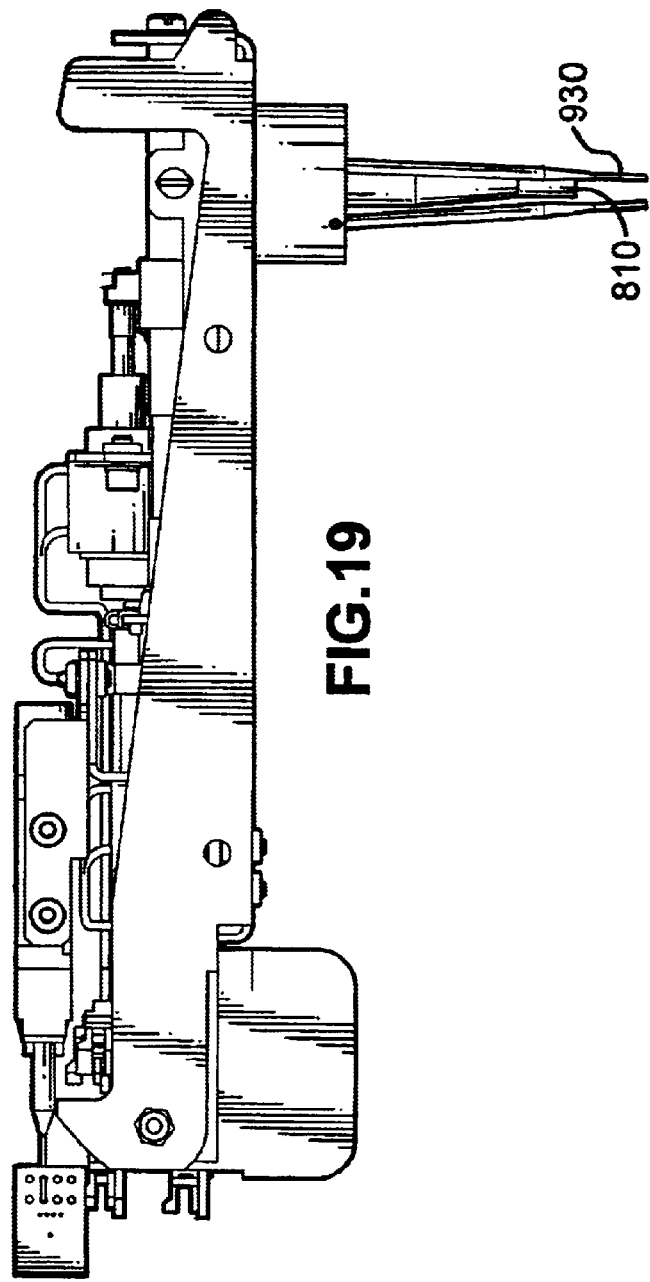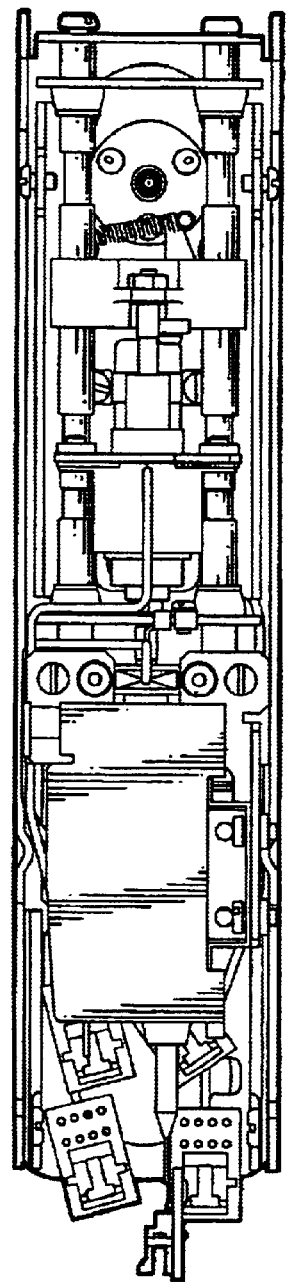
FIG.19
FIG.20

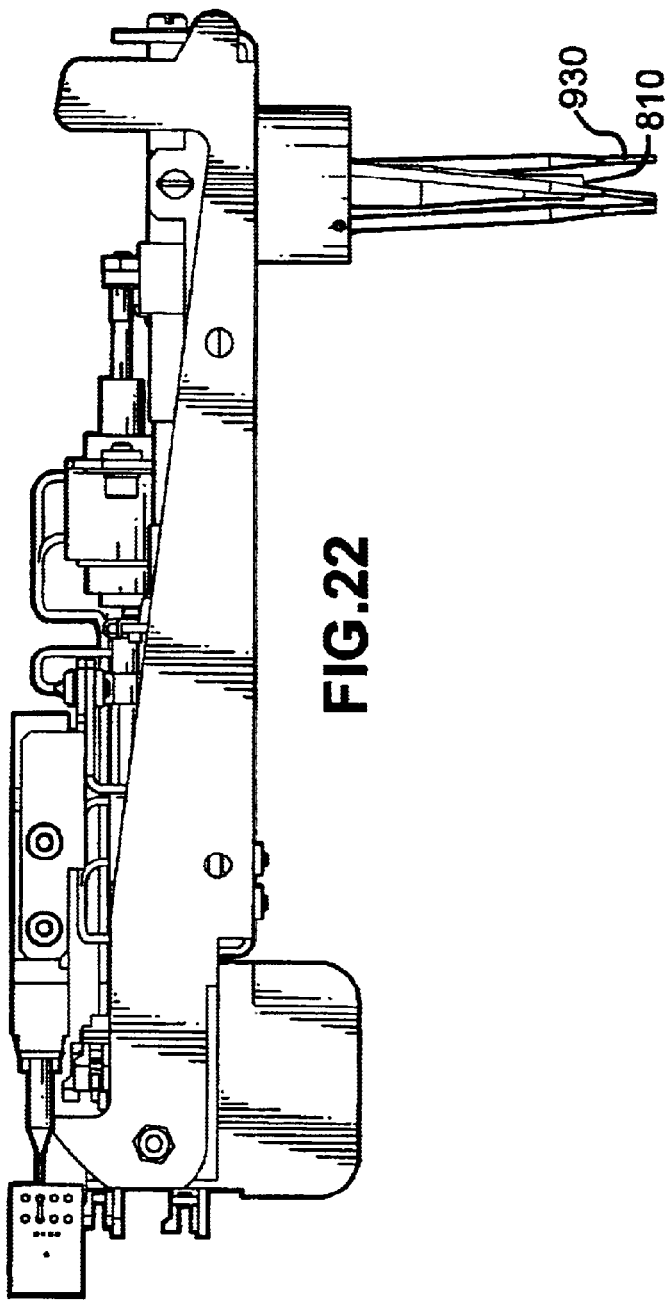
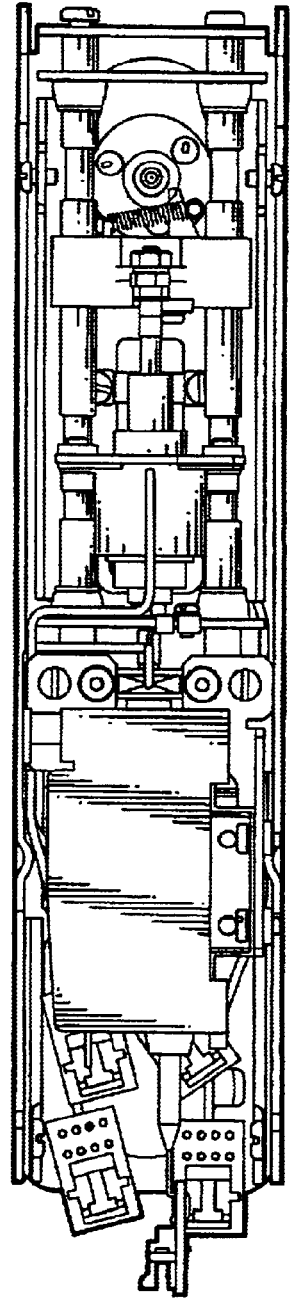

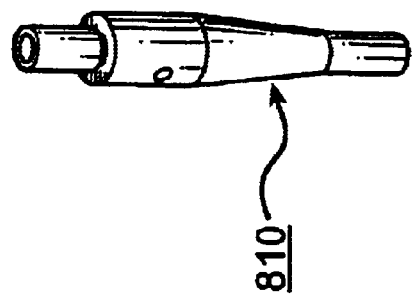
FIG.27
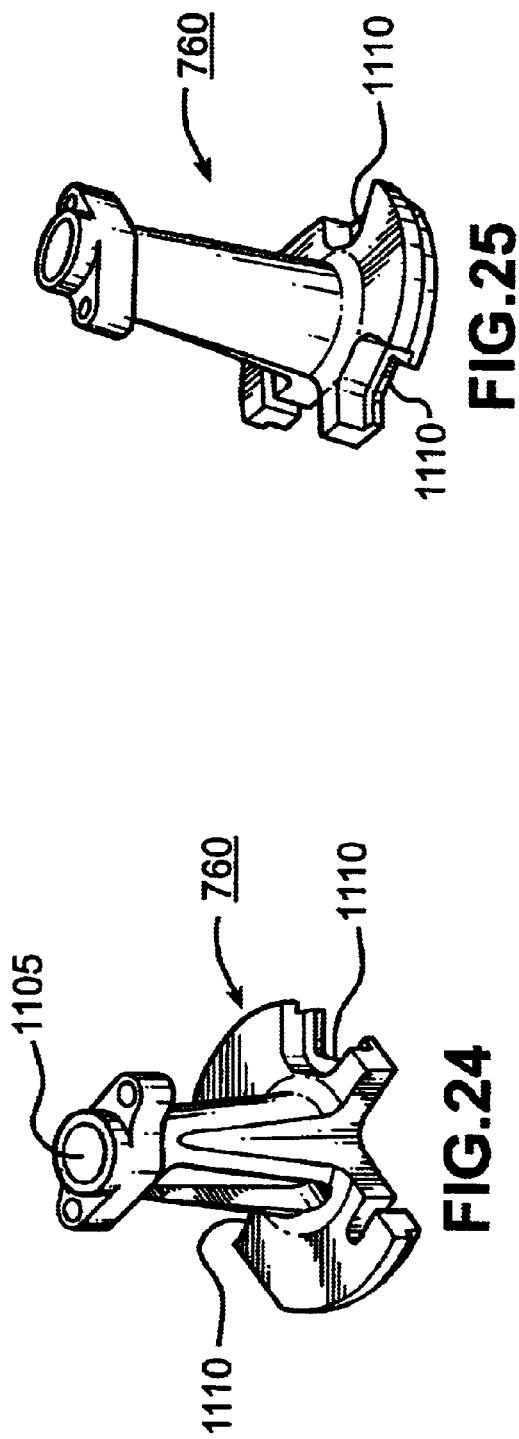
FIG.25
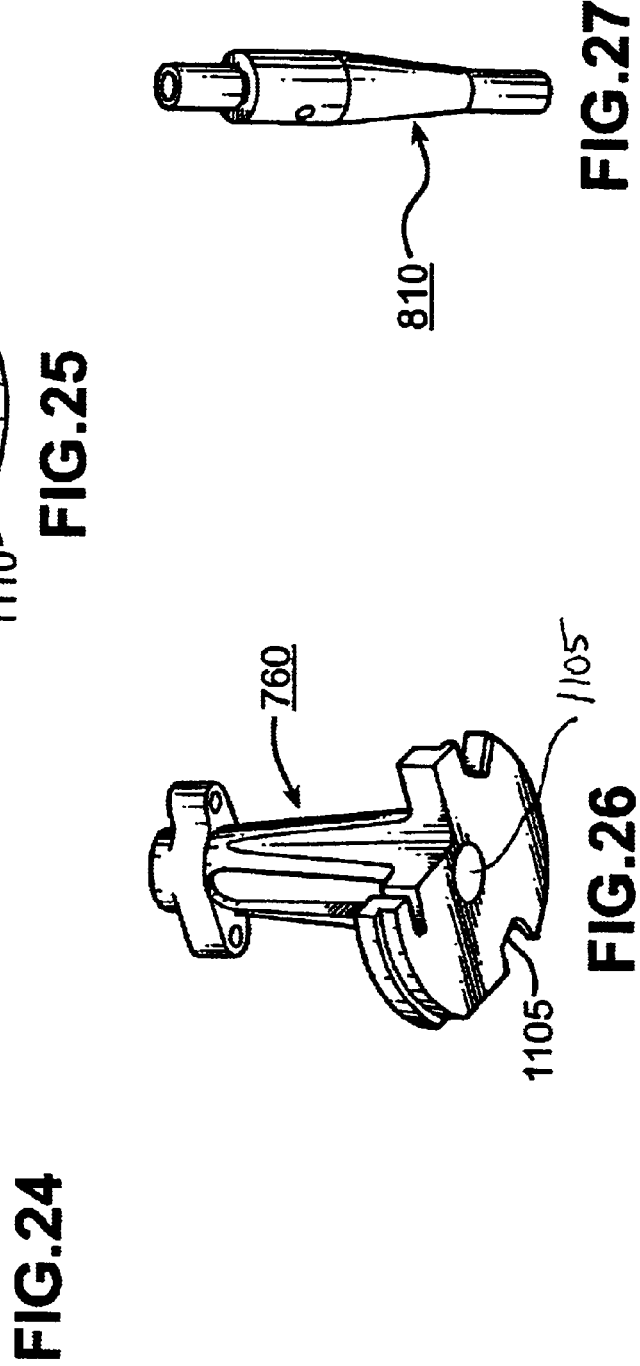
FIG.26
FIG.24

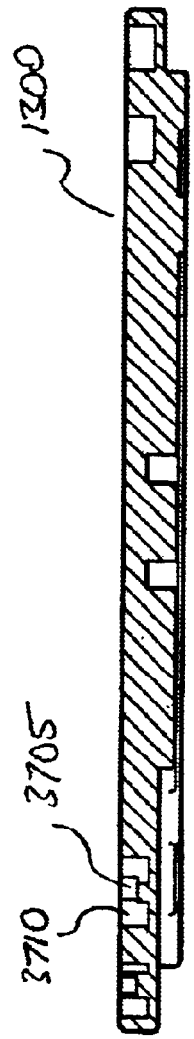
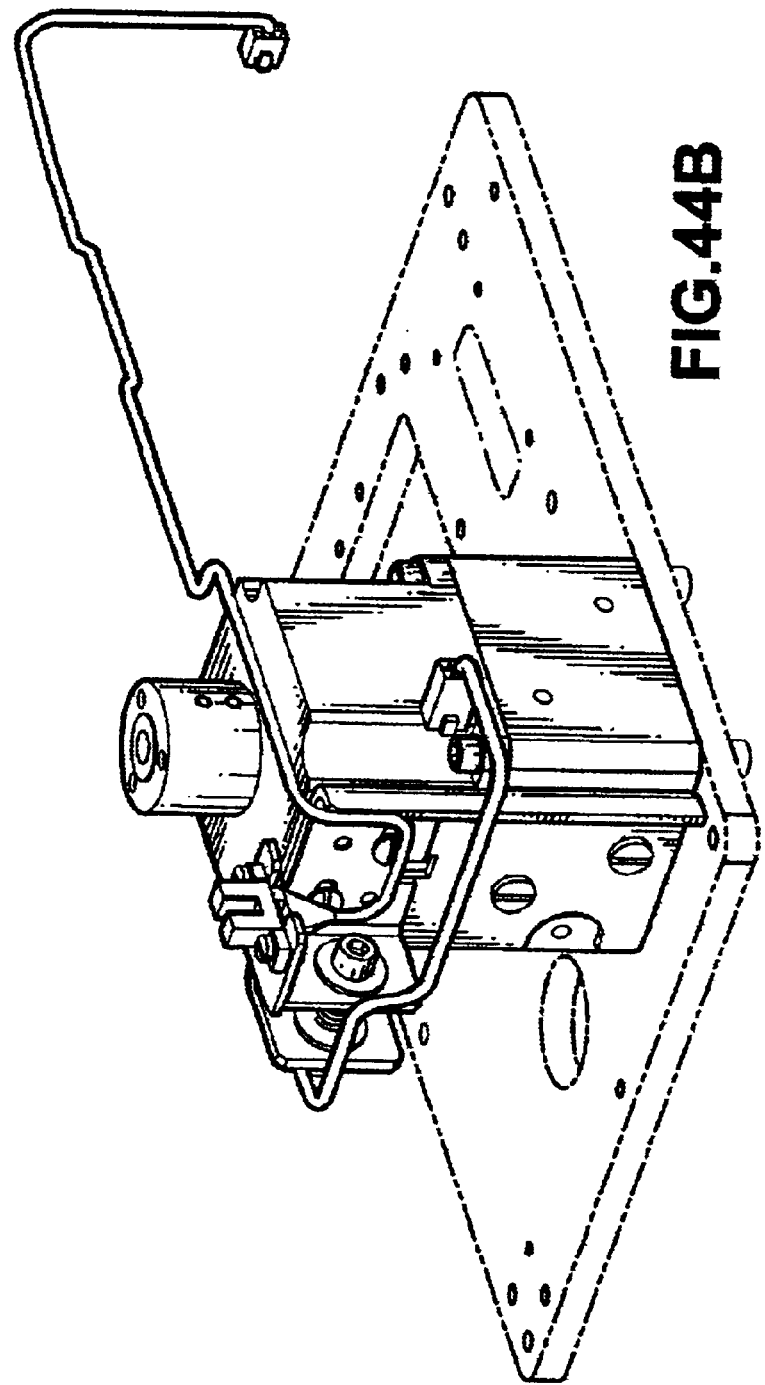

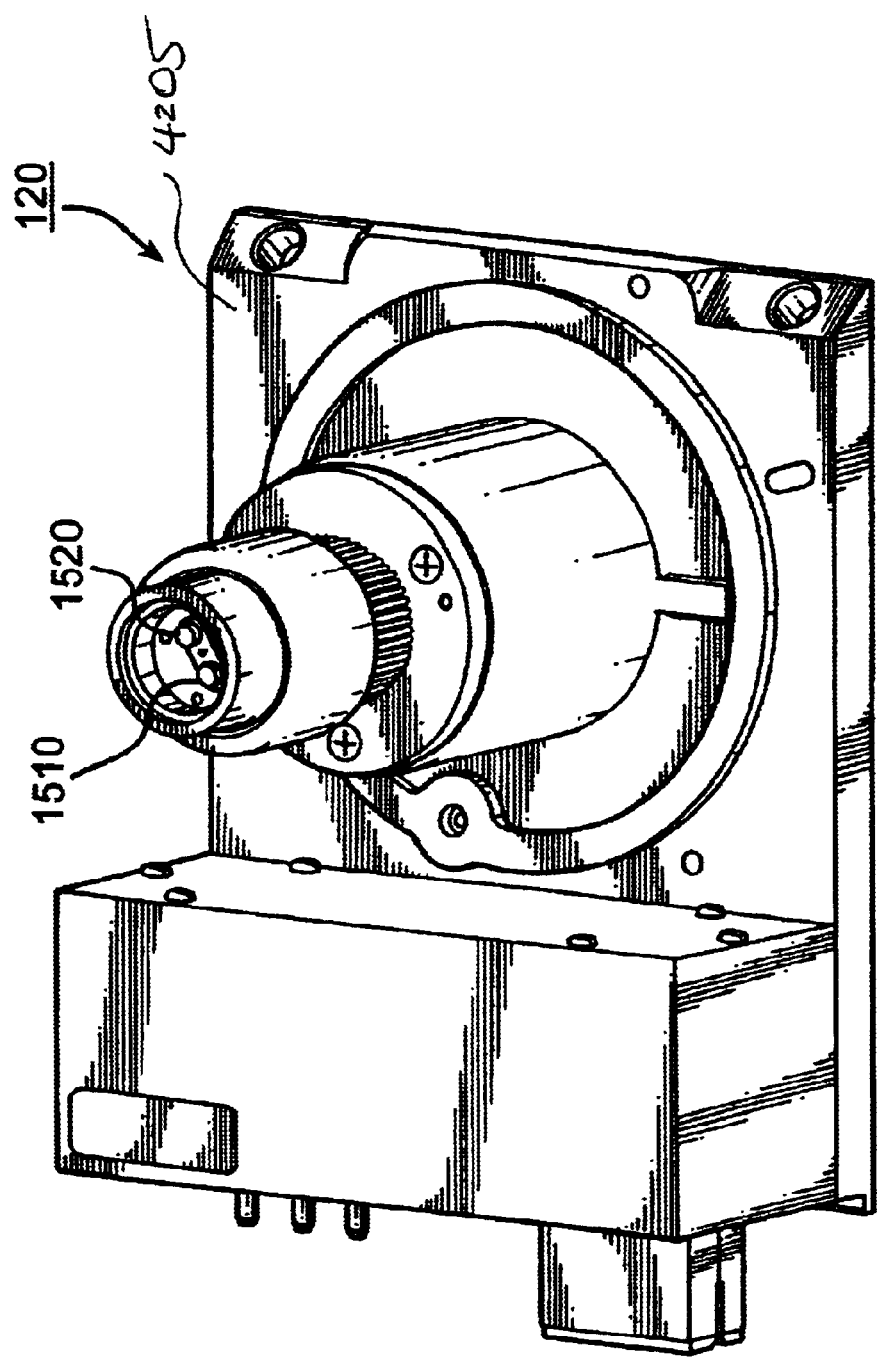

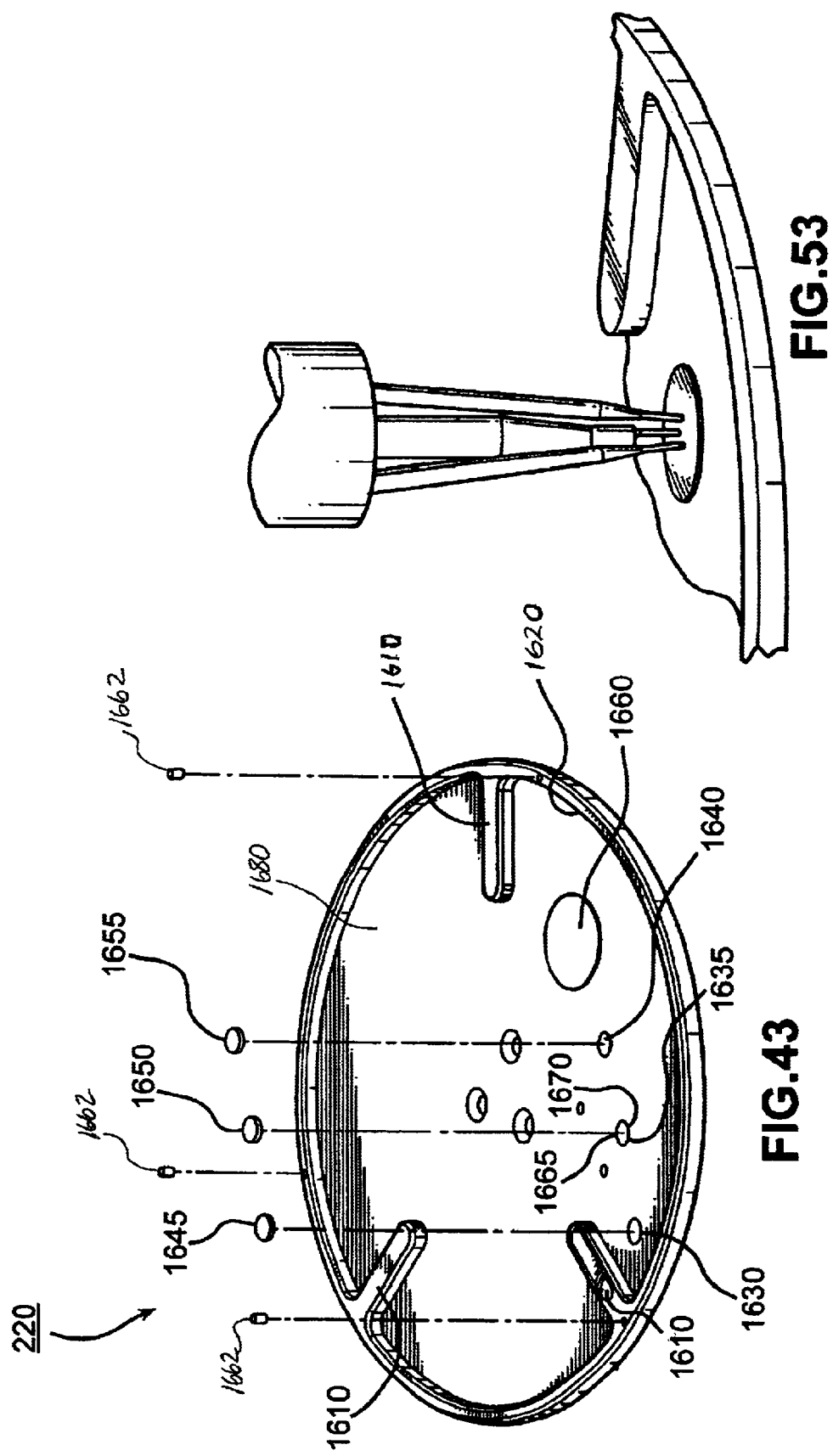

PLATEN FOR AUTOMATIC SAMPLER

RELATED APPLICATIONS

This application claims priority to U.S. Provisional Application No. 60/264,021 entitled "Automatic Sampling Device," which was filed on Jan. 26, 2001, which is incorporated by reference in its entirety.

FIELD OF THE INVENTION

The present invention relates to a device that provides samples to a measuring and testing apparatus. More particularly, the invention is directed to an automated device for providing samples to a measuring and testing apparatus.

BACKGROUND OF THE INVENTION

Differential thermal analysis (DTA) generally refers to a calorimetric technique for measuring physical properties of a substance by exposing the substance to different temperature regimes. DTA can be employed to measure parameters associated with phase transitions, glass transitions, polymerization/depolymerization, crystallization, softening, sublimation, dehydration, decomposition, oxidation, cure kinetics and so forth. A differential scanning calorimeter (DSC) measures the temperature and heat flow associated with energy-emitting or energy-absorbing (exothermic and endothermic, respectively) material transitions. DSCs are widely used in academic, government and private facilities for research purposes, as well as for quality control and production purposes. Hereinafter, reference will be made to DSC, although it is to be understood to encompass DTA as well.

During DSC testing, the material being analyzed ("sample") is heated or cooled according to a desired temperature profile. The results, such as differential temperature or heat flow, are measured and analyzed to understand the properties of the sample material. The basic theory of DSC analysis is well understood; the reader is referred to Reading, et al., U.S. Pat. No. 5,224,775 (the '775 patent) and U.S. Pat. No. 3,456,490 (the '490 patent) for details on the theory of operation of exemplary DSC systems. The '775 and '490 patents are herein incorporated by reference in their entirety. An improved DSC device is disclosed in U.S. Pat. No. 6,488,406, entitled "Differential Scanning Calorimeter", which was filed on Jan. 24, 2001, and which is herein incorporated by reference in its entirety.

There are also other well-known thermal analysis techniques, such as Pressure Differential Scanning Calorimetry (PDSC), Pressure Differential Thermal Analysis (PDTA), and Differential Photocalorimetry (DPC). The invention described hereafter may also be applied to instrumentation used for these techniques.

Typical DSC instrumentation includes the following basic components: a measurement module, a computer controller and associated software, and a results output device. The measurement module may include an interchangeable DSC cell, a cooling system, and a base cabinet. The DSC cell may also include a heated measurement chamber, which encloses a sensor assembly upon which the material to be analyzed is placed, and a furnace heater, which is used for heating the measurement chamber.

The cooling device may find application when temperature is being increased or decreased. Cooling devices used with DSC instrumentation include various types of heat exchangers, such as gas-cooled heat exchangers, liquid-cooled heat exchangers, and change-of-phase liquid-gas heat exchangers.

In the past, DSC testing was often a laborious, manual process, where a technician would have to load a sample pan with a sample, remove the cover(s) from the DSC cell, insert the loaded sample pan into the DSC measurement chamber, and replace the cover(s). After a test cycle was completed, the cover was removed from the DSC cell, the old sample pan was removed, the new sample pan was inserted, and so forth. If tests were to be conducted on multiple samples (such as might be the case for quality assurance testing in a large-scale manufacturing operation), the overall testing sequence would be very labor-intensive and time-consuming. Additionally, the manual nature of the process made it very likely that the testers would make errors, such as dropping or contaminating samples, misplacing samples, and so forth.

As a result, it was recognized that an apparatus for automatic sample retrieval and placement, an automatic sampler, would be beneficial. Accordingly, various automatic samplers have been developed. Some of these automatic samplers provide for a sample tray to be loaded with samples, which are retrieved and placed into the DSC cell.

However, current automatic samplers suffer significant disadvantages and drawbacks. For example, because some automatic samplers are robotic in nature, calibration becomes a significant issue. A number of factors may alter calibration: replacement of DSC cells; replacement of the sample tray; variations in sample tray size; autosampler component drift and wear; and so forth. Unfortunately, calibration of current automatic samplers is largely manual process. Not only is the calibration difficult and time-consuming, but the result is often suboptimal when performed by less-experienced personnel and/or when performed in a hurry. In fact, users of automatic samplers often avoid performing calibration because of these difficulties. Consequently, the DSC apparatus may begin to provide inaccurate measurements.

Additionally, some prior art automatic samplers perform calibration using a single sensing technique, e.g., an electrical sensor. However, a sensing technique can fail at times, such as when an electrical sensor is impaired by corrosion, oxidation, poor contact, and so forth. As a result, the calibration performed by such prior art automatic samplers can be inoperative or prone to errors.

Moreover, each of the various components in an automatic sampler (including calibration sensors) has its own tolerance and other variations. As a result, every automatic sampler that is produced can be slightly different from the others. Prior art automatic samplers have not taken this difference into account and, as a result, the calibration is suboptimal.

Some prior art autosamplers have employed robotic grippers for gripping sample pans to be placed in the DSC cell. However, prior art grippers have bad a number of significant drawbacks. For example, the gripped sample pan is sometimes not centered in the grippers, resulting in difficulties in placement of the sample pan. Prior art grippers sometimes apply uneven pressure to the sample pan, resulting in crimped or damaged sample pans. Pans may stick or adhere to a gripper finger, resulting in misplacement of the sample pan in the DSC cell. Replacement of fingers in the prior art grippers can require removal of a number of parts, making gripper maintenance a difficult task. Finally, some prior art grippers used a sensor, e.g., an electrical sensor, for pan location. However, reliance on a single sensor can lead to pan location failures when this single sensor is not receiving a proper reading.

Accordingly, prior art automatic samplers have not been robust or flexible in terms of the types of equipment they can use. In some cases, only standard DSC cell types or standard pan types (open versus closed, metallic versus ceramic, etc.) can be used. In other cases, only pans with standard dimensions can be used. Sometimes, the sample tray can accept only a certain type of sample pan having certain dimensions. This greatly limits the flexibility of the automatic sampler.

SUMMARY OF THE INVENTION

The present invention is directed to an automatic sampler. The automatic sampler device includes a cell having a sample platform and a reference platform, a sample tray; and a sample arm. The sample tray has wells into which sample pans and reference pans are inserted. The geometry of the automatic sampler device permits the sample platform, the reference platform, and the wells in the sample tray to be accessed by the sample arm along a common arc.

According to another aspect, the automatic sampler device includes a sample tray with wells, a sample arm, and a gripper device. The gripper device has gripping fingers. The gripping fingers open or close in a manner that tends to center objects grasped by the gripper device.

According to another aspect, the automatic sampler device includes a sample tray with wells, a sample arm, and a gripper device. The sample arm has an optical sensor and an electrical sensor. The optical sensor and electrical sensor can be used to detect a pan grasped by the gripper device.

According to another aspect, the automatic sampler device includes a sample tray with wells, a sample arm, and a gripper device. The gripper advice is capable of grasping pans of different sizes.

According to another aspect, the automatic sampler device includes a sample tray with wells, a platen, a sample arm, a gripper device, and an optical sensor. The platen includes a reflective area used to calibrate the sample tray.

Accordingly, one object of the invention is to provide an automatic sampler that provides precise and repeatable measurements.

Another object of the invention is to provide an automatic sampler that is easy to use.

Another object of the invention is to provide an automatic sampler that allows the user to quickly and efficiently perform thermal analysis measurements on large numbers of samples.

Another object of the invention is to provide an automatic sampler with an improved calibration function that can be operated in a substantially automated fashion.

Another object of the invention is to provide an automatic sampler with sensors for providing a pan location capability.

Another object of the invention is to provide an automatic sampler having a platen for calibrating the automatic sampler.

Another object of the invention is to provide an automatic sampler whereby a sample platform, reference platform, and well can be accessed by a sample arm along a common arc.

These and other objects of the present invention are described in greater detail in the following description of the invention, the appended drawings, and the attached claims.

The present invention is directed to a gripper device. According to one aspect, the gripper device includes fingers with grasping ends. The gripper device includes a means to cause the grasping ends to open and close. When the means is engaged, the grasping ends open and close to define a circumference.

According to another aspect, the gripper device includes fingers, an upper flat member, and a lower flat member. The upper flat member and lower flat member have holes. The upper flat member and lower flat member are substantially parallel. The fingers have grasping ends. The fingers are inserted into the upper flat member and lower flat member. When the upper flat member is rotated relative to the lower flat member, the grasping ends of the fingers open and close.

According to another aspect, a gripper assembly has a gripper device with fingers and a rotating member. The fingers have grasping ends. The gripper assembly also has a motor and means for rotating the rotating member. The gripper device opens or closes the grasping ends in response to the rotation of the rotating member.

According to another aspect, a gripper finger has a top section, a middle section, a bottom section. The gripper finger has a plurality of balls located above the grasping end of the gripper finger.

Accordingly, one object of the invention is to provide a gripper device that can be used to grasp objects of varying materials and dimensions.

Another object of the invention is to provide a gripper device that can be used to reliably to repeatedly retrieve and release pans used in thermal analysis testing.

Another object of the invention is to provide a gripper device that tends to center pans grasped by the fingers of the gripper device.

Another object of the invention is to provide a gripper device that includes multiple fingers that open and close along a common circumference.

These and other objects of the present invention are described in greater detail in the following description of the invention, the appended drawings, and the attached claims.

The present invention is directed to a gripper device having sensors. According to one aspect, a sample arm has a gripper device with multiple fingers, an electrical sensor, and an optical sensor. The electrical sensor and optical sensor move with the sample arm.

According to another aspect, a sample arm has a gripper device with multiple fingers and a plurality of sensors. The sensors move with the sample arm. The sensors are capable of detecting an object or calibrating a coordinate.

According to another aspect, a sample arm has a gripper device with multiple fingers and a plurality of sensors. The sensors can be used to detect pans held by the gripper device. The sensors permit different kinds of pans to be grasped by the gripper device.

Accordingly, one object of the invention is to provide a gripper device with multiple sensors.

Accordingly, one object of the invention is to provide a gripper device with an improved pan detection capability.

Another object of the invention is to provide a gripper device that permits improved calibration.

Another object of the invention is to provide a gripper device that includes a redundant pan detection capability.

Another object of the invention is to provide a gripper device that can grasp different types of pans.

These and other objects of the present invention are described in greater detail in the following description of the invention, the appended drawings, and the attached claims.

The present invention is directed to a technique for performing a substantially automatic calibration of an automatic sampler device. According to an aspect, the automatic sampler device includes a cell with a sample platform and a reference platform; a sample arm; a sample tray, and a platen. The sample tray includes wells into which pans are inserted. The platen may include conductive and/or reflective areas for calibration. The sample arm has an electronic sensor and an optical sensor. The electrical sensor and the optical sensor are used to calibrate the positions of one or more of: the sample platform, the reference platform, and a well.

According to another aspect, autocalibration is optimized further by adjusting autocalibration results with a set of stored offset coefficients. The offset coefficients are generated by performing a manual calibration. The difference between the results of the manual calibration and an autocalibration are stored as offset coefficients. The offset coefficients can be applied to subsequent autocalibrations.

Accordingly, one object of the invention is to provide an autocalibration feature that with an improved accuracy.

Another object of the invention is to provide an autocalibration feature that can be substantially automated.

Another object of the invention is to provide an autocalibration feature that uses multiple sensors to gather calibration information.

Another object of the invention is to provide an autocalibration feature that accounts for tolerances and/or biases in the autocalibration apparatus.

These and other objects of the present invention are described in greater detail in the following description of the invention, the appended drawings, and the attached claims.

Sample Tray

The invention relates to a sample tray to be used by an automatic sampler having a sample arm. According to an aspect, the sample tray includes wells that can be accessed by a sample arm along a common arc of rotation, without moving the sample arm in and out.

According to another aspect, the sample tray has several concentric rows of wells for holding sample pans and reference pans. Each row of wells lies along an inner circumference of the sample tray. The rows are placed so that when the sample tray is rotated, every well can be located on a common arc of rotation relative to a sample arm.

According to another aspect, a well in a sample tray is configured with a pan receiving area and finger receiving areas. Gripper fingers can be extended into the finger receiving areas to access pans of different sizes.

Accordingly, one object of the invention is to provide a sample tray that includes a large number of wells for testing multiple samples.

Another object of the invention is to provide a sample tray with wells that are oriented so that each well can be accessed by a sample arm along a common arc of rotation.

Another object of the invention is to provide a sample tray with wells that permit a variety of pan sizes to be used with an automatic sampler.

These and other objects of the present invention are described in greater detail in the following description of the invention, the appended drawings, and the attached claims.

Platen

The invention relates to a platen to be used with a sample tray of an automatic sampler. According to an aspect, the platen includes both electrically conductive and reflective areas that can be used to calibrate the sample tray. According to another aspect, calibration of the sample tray can be performed in all three dimensions.

Accordingly, an object of the invention is to provide a platen that can be used to calibrate a sample tray.

Another object of the invention is to provide a platen that includes electrically-responsive areas and optically-responsive areas that can be used to calibrate a sample tray.

Another object of the invention is to provide a platen that includes responsive areas that can be used to calibrate a sample tray in all three dimensions.

These and other objects of the present invention are described in greater detail in the following description of the invention, the appended drawings, and the attached claims.

BRIEF DESCRIPTION OF THE DRAWINGS

FIG. 19 is a side view of an arm with a gripper device in a closed position according to a preferred embodiment of the present invention.

FIG. 20 is a top view of an arm with a gripper device in a closed position according to a preferred embodiment of the present invention.

FIG. 22 is a side view of an arm with a gripper device in an open position according to a preferred embodiment of the present invention.

FIG. 23 is a top view of an arm with a gripper device in an open position according to a preferred embodiment of the present invention.

FIG. 24 is a top isometric view of a finger retainer according to a preferred embodiment of the present invention.

FIG. 25 shows another isometric view of a finger retainer according to a preferred embodiment of the present invention.

FIG. 26 is a bottom isometric view of a finger retainer according to a preferred embodiment of the present invention.

FIG. 27 is an isometric view of a sensor assembly according to a preferred embodiment of the present invention.

FIG. 33 is an enlarged view of a well according to a preferred embodiment of the present invention.

FIG. 34 is an enlarged view of another well according to a preferred embodiment of the present invention.

FIG. 35 is an enlarged view of yet another well according to a preferred embodiment of the present invention.

FIG. 37A is a cross-sectional view of a tray according to a preferred embodiment of the present invention.

FIG. 42 is an isometric view of a DSC cell according to a preferred embodiment of the present invention.

FIG. 43 is an isometric view of a rotating table according to a preferred embodiment of the present invention.

FIG. 44B is an assembled isometric view of a table motor and related parts according to a preferred embodiment of the present invention.

FIG. 53 is an isometric view of a preferred embodiment of a gripper device and a conductive area 1660.

DETAILED DESCRIPTION OF THE INVENTION

Figure 1:
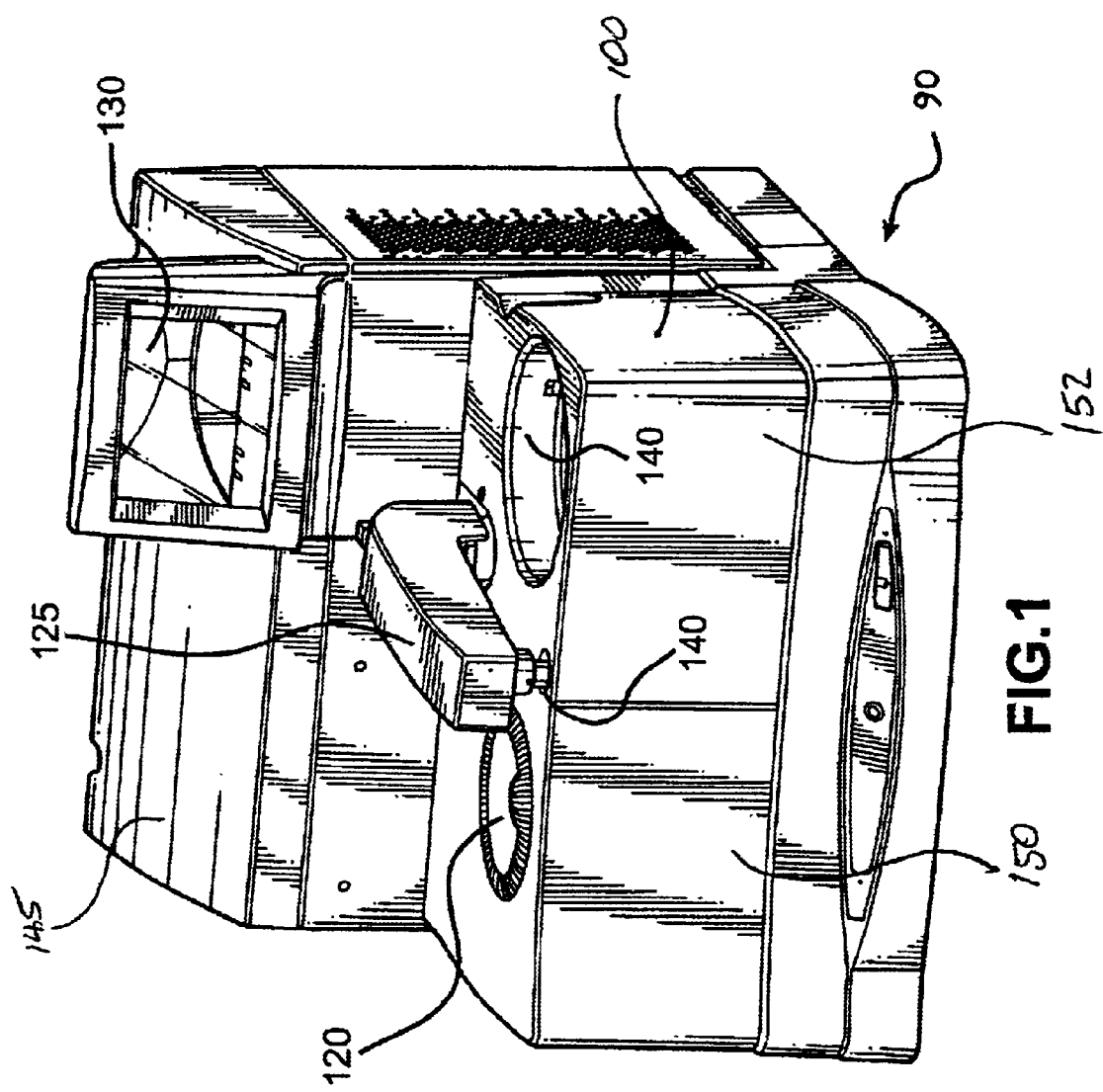
FIG. 1 shows an exemplary DSC system including an autosampler according to a preferred embodiment of the present invention.

FIG. 1 shows a preferred embodiment of a thermal measurement instrument 90. Thermal measurement instrument 90 includes a preferred embodiment of an automatic sampler 100 according to the present invention. Thermal measurement instrument 90 may perform measurements using DSC Pressure Differential Scanning Calorimetry (PDSC), Pressure Differential Thermal Analysis (PDTA), Differential Photocalorimetry (DPC), or other techniques. Preferably, thermal measurement instrument 90 performs differential scanning calorimetry (DSC) measurements.

Thermal measurement instrument 90 includes cell 120 and automatic sampler (or "autosampler") 100. Cell 120 can be any type of cell for conducting thermal measurements on a sample material placed in the cell. Preferably, cell 120 is a DSC cell. In FIG. 1, cell 120 is surrounded by cell cover 150. Cell cover 150 has a hole permitting access to cell 120. Thermal measurement instrument 90 also includes a body portion 145 that preferably includes a display 130.

Autosampler 100 includes autosampler cover 152, access area 140, disposal area 140, and arm 125. Display 130 is capable of displaying information to the user. Preferably, display 130 is a touchscreen-type display that can receive information by touchscreen commands.

Arm 125 is preferably located between cell 120 and access area 140 (discussed below). Preferably, arm 125 is located so that it can rotate to retrieve samples to be tested, to place samples to be tested, and to dispose of samples that have been tested. Preferably, arm 125 is capable of both rotational (angular) and longitudinal (radial) motion.

Access area 140 is an opening in autosampler 100 that permits access to samples or pans. Access area 140 is preferably located at a position that is accessible by arm 125. Preferably, access area 140 is located so that arm 125 can access wells in a sample tray held by access area 140. Access area 140 is surrounded by an autosampler cover 152. There is a hole in the top surface of autosampler cover 152.

Disposal area 140 is an opening in autosampler 100 that permits arm 125 to release or dispose of sample pans and/or reference pans. Disposal area can be located at various positions that are accessible by arm 125. Preferably, disposal area 140 is located between cell 120 and access area 140, as shown in FIG. 1.

Generally, autosampler 100 operates as follows. The user loads the samples into sample pans, which are inserted into a sample tray (not shown). The sample tray is placed into access well 140 of autosampler 100. The testing sequence is initiated. Arm 125 retrieves a sample pan. The sample pan is moved to DSC cell 120 and placed onto a sample platform so that an experiment can be conducted. Upon completion of the measurement, the sample pan is retrieved from the sample platform and is released into disposal area 140 or returned to the sample tray. The autosampler 100 then provides access to another sample pan, and the process repeats.

Preferably, arm 125 can access DSC cell 120 and disposal area 140 along a common arc. Preferably, the sample tray can move (e.g., rotate) to align different sample pans with arm 125.

Preferably, a testing sequence for a number of samples can be programmed using display 130. The testing sequence may identify which samples are to be tested and the experiments conducted with those samples.

Figure 2:
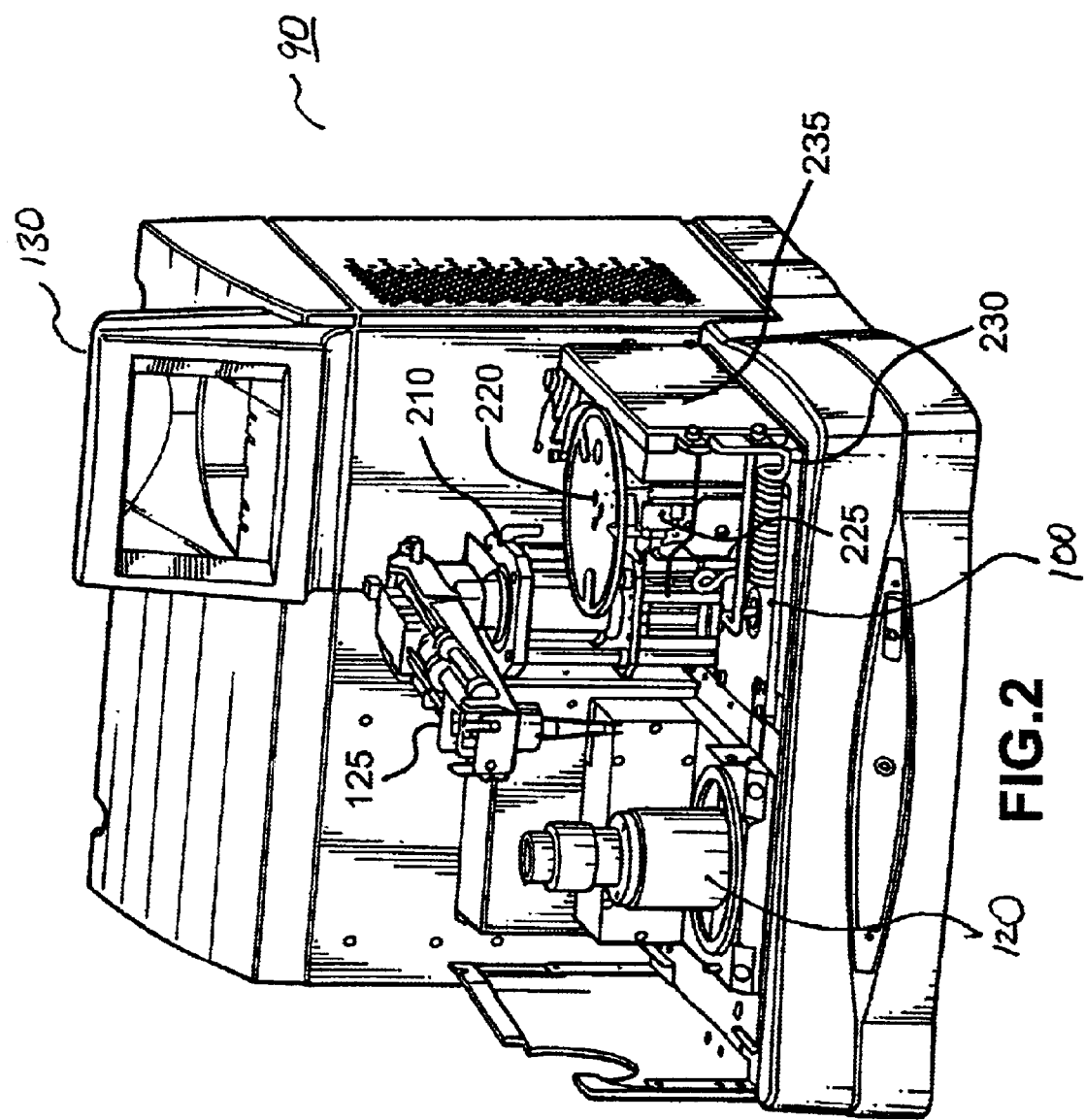
FIG. 2 shows an interior view of an exemplary DSC system according to a preferred embodiment of the present invention.

FIG. 2 shows a preferred embodiment of thermal analysis instrument 90 with cell cover 150, autosampler cover 152, and the cover of arm 125 removed. FIG. 2 shows DSC cell 120; arm 125; arm drive assembly 210; rotating table 220; table motor 225; base plate 230; and control module 235.

Arm 125 is coupled to arm drive assembly 210. Arm drive assembly 210 causes arm 125 to rotate and/or displace vertically. Preferably, arm drive assembly 210 imparts both rotational and vertical motion to arm 125.

Rotating table 220 is coupled to table motor 225. Table motor 225 imparts motion to rotating table 220. Preferably, table motor 225 imparts rotational motion to rotating table 220. Rotating table 220 is used for calibrating positions accessed by arm 125. Rotating table 220 is designed to receive a sample tray 1300 (See FIG. 30) adapted to hold pans. Preferably, rotating table 220 is also used for calibrating well positions on a sample tray.

Control module 235 communicates electronically with components in autosampler 100 to receive information and/or control their operation. In FIG. 2, control module 235 is preferably located adjacent to rotating table 220 and table motor 225. Control module 235 could be located in other positions in autosampler 100. Control module 235 could be located separately from autosampler 100. Preferably, control module 235 can be programmed using display 130.

Figure 3:
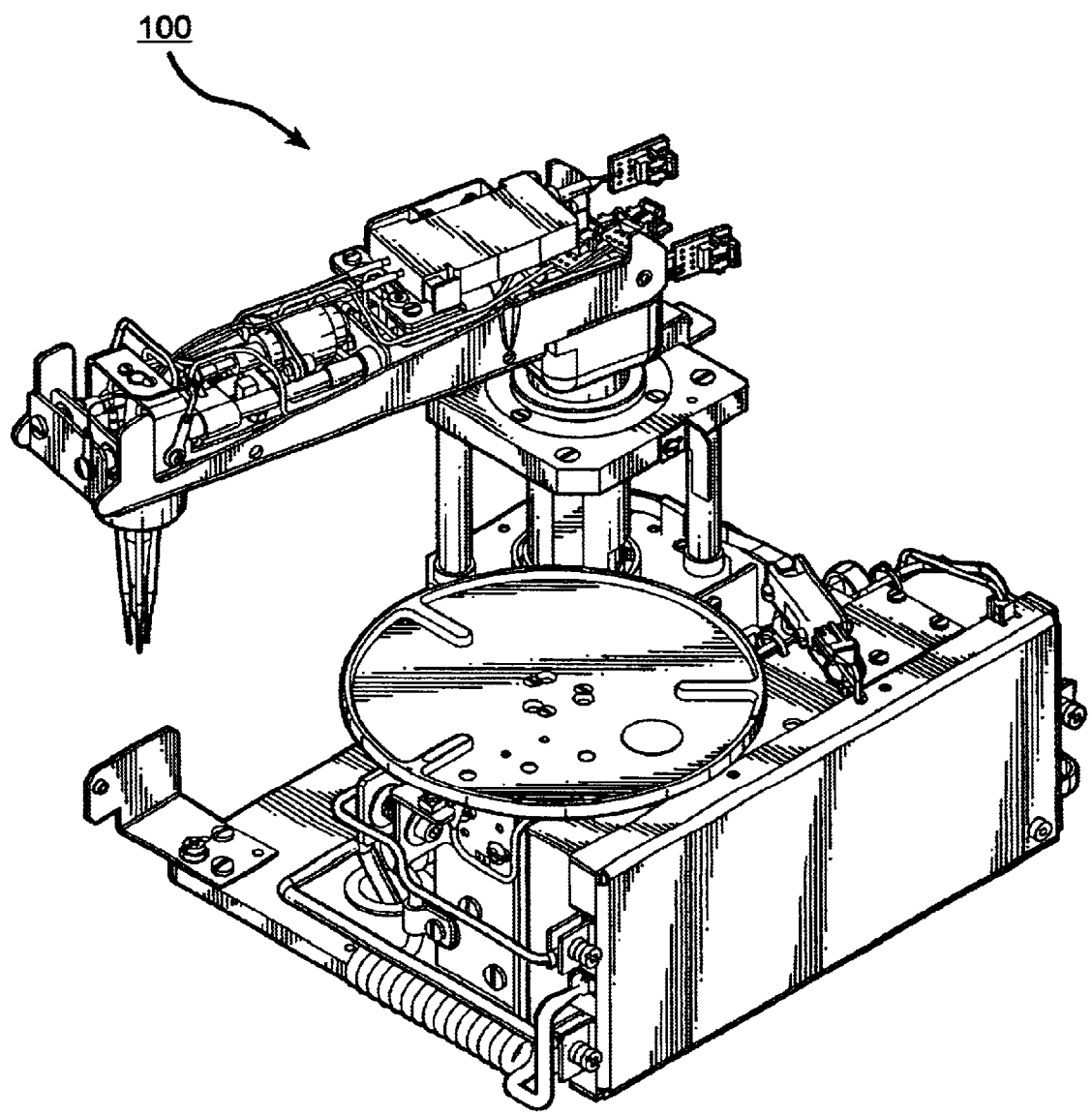
FIG. 3 is an isometric view of an autosampler according to a preferred embodiment of the present invention.
Figure 4:
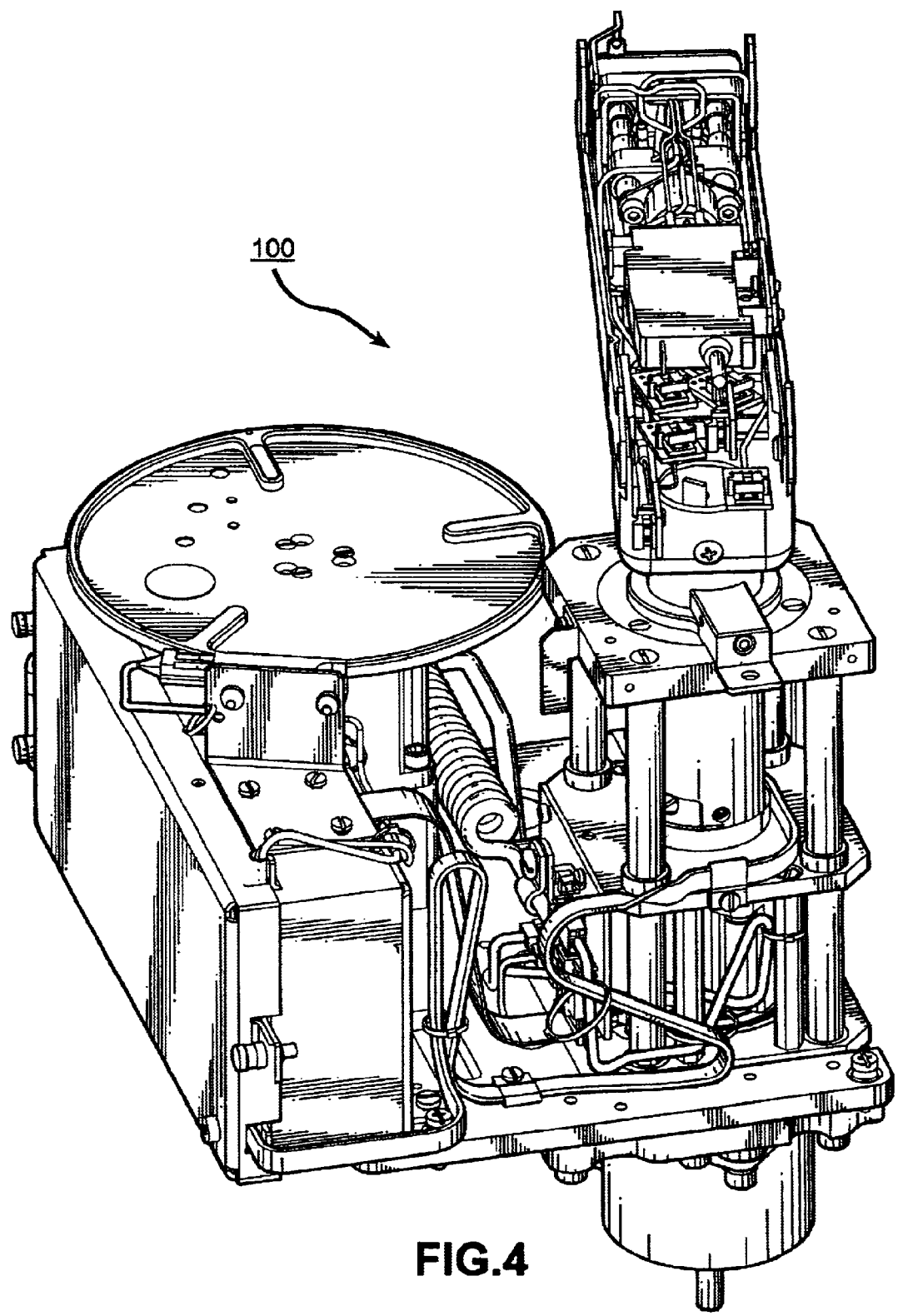
FIG. 4 is a rear isometric view of an autosampler according to a preferred embodiment of the present invention.

FIG. 3 is an isometric of a preferred embodiment of autosampler 100. FIG. 4 is a rear view of a preferred embodiment of autosampler 100. Preferably, autosampler 100 is a modular assembly that can be easily installed and removed from thermal analysis instrument 90.

Figure 5:
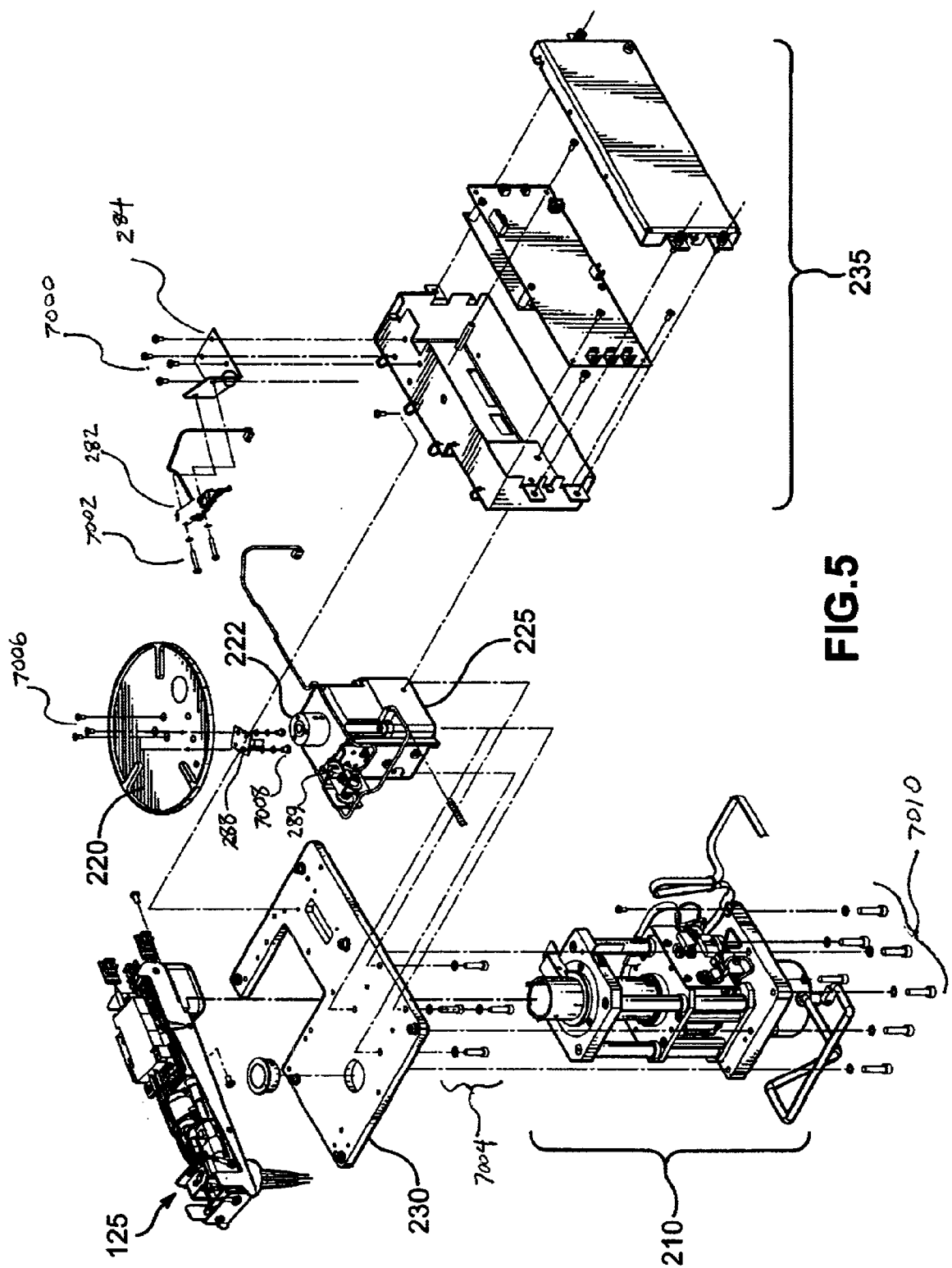
FIG. 5 is an exploded view of an autosampler according to a preferred embodiment of the present invention.

FIG. 5 is an exploded view of a preferred embodiment of autosampler 100. The major components of FIG. 5 include control module 235, rotating table 220, table motor 225, arm drive assembly 210, base plate 230, and arm 125.

As previously indicated, control module 235 may communicate electronically with various components of autosampler 100 in order to monitor and control operations. A bracket 284 is affixed to control module 235 using a first set of fasteners 286. Fasteners 286 may comprise any reliable means for coupling or attaching components, including screws, nuts, bolts, pins, rivets, welds, brackets, glue, monolithic casting and so forth. A photosensor 282 is attached to bracket 284 using a second set of fasteners 7002. Photosensor 282 may be any sensing device capable of sensing light, including fiber optic sensors, LED sensors, and so forth. Preferably, photosensor 282 is an optical transmitter and receiver that projects an optical beam to determine whether a sample tray (discussed below) is on top of rotating table 220. Control module 235 is attached to base plate 230. When attached to base plate 230, control module may be disposed in autosampler 100 as illustrated in FIG. 2.

Table motor 225 attaches at one end to base plate 230 using a third set of fasteners 7004. At the other end, table motor 225 is coupled to hub 222. Hub 222 attaches to rotating table 220 using a fourth set of fasteners 7006. Rotating table 220 may include a rotating table home flag 288 attached using a fifth set of fasteners 7008.

Table motor 225 can be any motor capable of rotating the rotating table 220. Preferably, table assembly drive motor 225 is a stepping motor. In an exemplary embodiment, table assembly drive motor 225 is a stepping motor having 400 steps per revolution that has been microstepped by sixty-fourths to provide 25,600 steps of rotational precision per revolution.

Hub 222 couples a rotating shaft (not shown) of table motor 225 to rotating table 220. Hub 222 could have various shapes, such as rectangular, spherical, and so forth Preferably, hub 222 is cylindrical.

Rotating table home flag 288 may be used in conjunction with a sensor to determine when rotating table 220 is in a home position. Rotating table home flag 288 may be any component capable of being sensed or detected. Preferably, rotating table home flag 288 has a light blocking member that is detected by rotating table sensor 289. Preferably, rotating table sensor 289 is an optical sensor that transmits a light beam between two shoulders. When rotating table 220 rotates to a position where rotating table home flag 288 blocks the light beam, table sensor 289 detects the break in the light beam. This break in the beam coincides with the home position. According to the preferred embodiment, this home position corresponds to a specific well in a sample tray attached to rotating table 220.

Also shown in FIG. 5 is arm 125 and arm drive assembly 210. Arm drive assembly 210 is mounted to base plate 230 using a sixth set of fasteners 7010. Any suitable mounting arrangement could be employed. In a preferred embodiment, arm drive assembly 210 is mounted so that approximately the top two-thirds of arm drive assembly 210 is above base plate 230. Arm drive assembly 210 attaches to sample arm 125 in order to move sample arm 125. In a preferred embodiment, arm drive assembly 210 moves sample arm 125 vertically and rotationally.

Preferably, control module 235 monitors and controls the various components, including controlling the displacement imparted by the motors. Under control of control module 235, table motor 225 rotates rotating table 220. Periodically, the home position of rotating table 220 is detected using rotating table home flag 286. Under control of control module 235, the sample arm 125 can be raised, lowered, and rotated by arm drive assembly 210. Sample arm 125 can be moved to touch or be near rotating table 220. Rotating table 220 can be rotated so that sample arm 125 can access different areas on rotating table 220.

Figure 6:
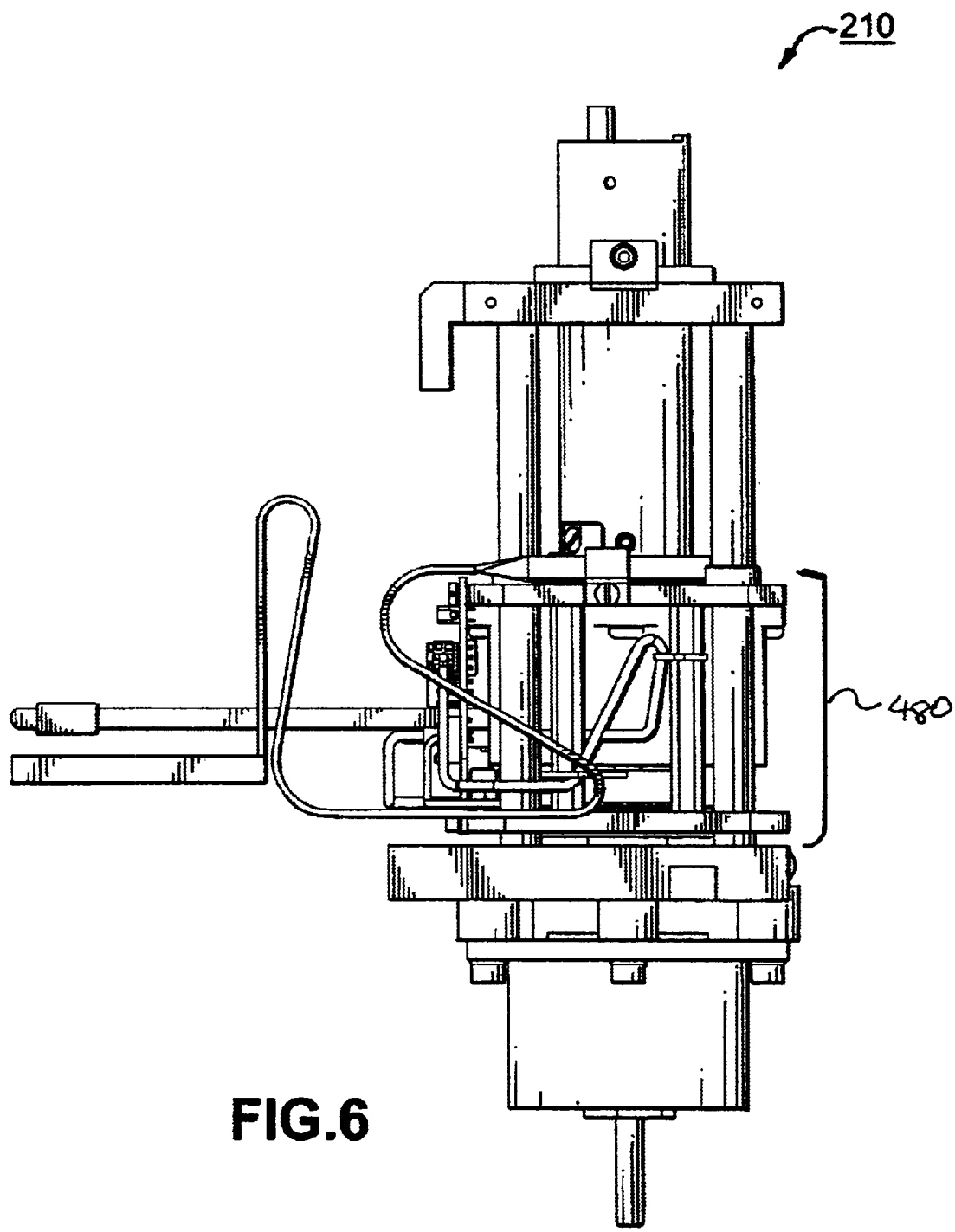
FIG. 6 is a side elevation view of an arm drive assembly according to a preferred embodiment of the present invention.
Figure 7:
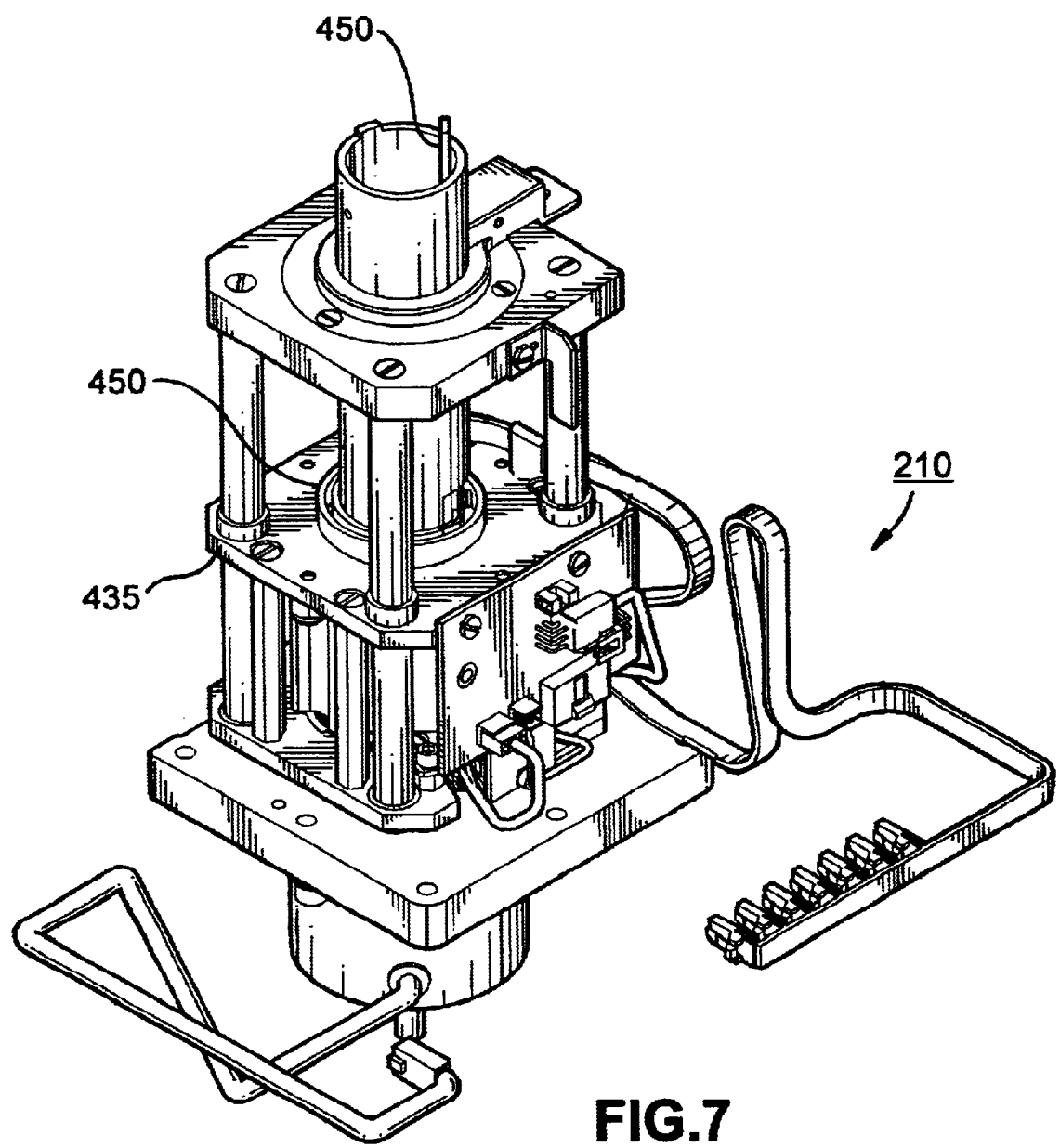
FIG. 7 is an isometric view of an arm drive assembly according to a preferred embodiment of the present invention.

FIG. 6 is a side view of arm drive assembly 210 according to an embodiment of the invention. FIG. 7 is an isometric view of arm drive assembly 210 according to an embodiment of the invention.

Figure 8:
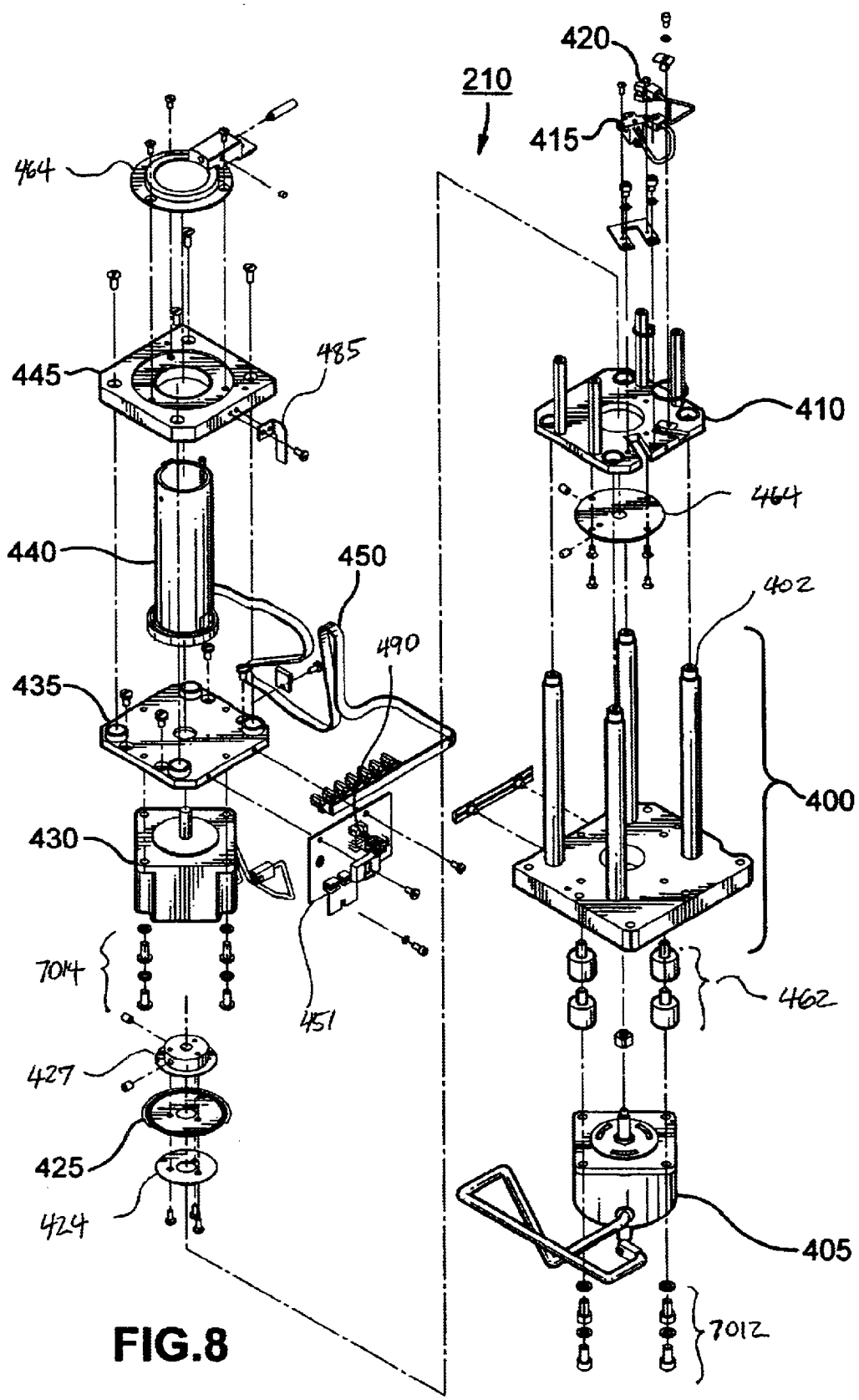
FIG. 8 is an exploded view of an arm drive assembly according to a preferred embodiment of the present invention.

FIG. 8 is an exploded view of a preferred embodiment of arm drive assembly 210. Moving from the bottom to the top of FIG. 8, the major components of arm drive assembly 210 include arm linear motor 405; vertical frame 400; bottom moving plate 410; rotation sensor 415; home sensor 420; rotation indicator 425; hub 427; arm rotational motor 430; top moving plate 435; rotating shaft 440; top frame plate 445; cable 450; and grounding retainer 464.

Arm linear motor 405 is attached to the bottom of vertical frame 400 using a seventh set of fasteners 7012. Preferably, isolators 462 are disposed between arm linear motor 405 and vertical frame 400 to provide mechanical vibration isolation. Isolators 462 could be made of rubber, foam, or any other material capable of providing dampening.

According to a preferred embodiment, arm linear motor 405 provides vertical (up and down) motion in order to raise and lower arm 125. Referring back to FIG. 6, arm linear motor 405 may control the vertical position of sample arm 125 by moving the moving portion 480 up and down. Arm linear motor 405 is preferably a stepper motor that provides precise vertical displacement based on steps or pulses sent to the motor from control module 235.

Returning to FIG. 8, vertical frame 400 includes posts 402 that accommodate apertures in bottom moving plate 410 and also accommodate apertures in top moving plate 435. Posts 402 attach to top frame plate 445 using fasteners (not shown). A collar 464 may be disposed on top frame plate 445.

A rotation sensor 415 and a home sensor 420 may be attached to bottom moving plate 410 or any other suitable location. Rotation sensor 415 is used to sense the rotational position of arm rotational motor 430. Home sensor 420 is used to sense the home position of arm rotational motor 430. Rotation sensor 415 and home sensor 420 could be any sensor capable of detecting a position. Preferably, rotation sensor 415 and home sensor 420 are optical sensors capable of detecting a light beam.

Arm rotational motor 430 is positioned above bottom moving plate 410 and below top moving plate 435. Arm rotational motor 430 is attached to the bottom of middle plate 435 using an eighth set of fasteners 7014. A support member 424, rotation indicator 425, and hub 427 are attached to arm rotational motor 430. Support member 424, rotation indicator 425, and hub 427 are preferably attached to a shaft (not shown) projecting downward from the bottom of arm rotation motor 430. Support member 424 and hub 427 are used to secure rotation indicator 425 in position. Support member 424 are preferably circular in shape, although any suitable means for securing rotation indicator 425 could be used.

Rotation indicator 425 provides information on the rotational position of arm rotational motor 430. Preferably, rotation indicator 425 is capable of providing information on a current rotational position and a home position. Rotation sensor 415 and home sensor 420 detect rotation indicator 425 to determine positions. According to a preferred embodiment, rotation sensor 415 and home sensor 420 can be used to detect a current position or a home position. Preferably rotation indicator 425 is an encoder wheel, further discussed in connection with FIGS. 9A and 9B.

Arm rotational motor 430 is preferably a stepping type motor providing precise control over the rotation. In one embodiment, rotation motor 430 is a stepping motor having 400 steps per revolution that has been micro-stepped down to sixty-four microsteps per revolution. Accordingly, there are about 25,600 step positions available per revolution.

Arm rotational motor 430 is used to rotate sample arm 125. The components coupling arm rotational motor 430 and sample arm 125 include rotating shaft 440, top plate 445, and grounding retainer 464. The top shaft of arm rotational motor 430 attaches to the bottom of rotating shaft 440. Rotating shaft 440 may be any longitudinal member capable of coupling arm rotational motor 430 and arm 125, including a shaft, solid tube, hollow tube, square tube, and so forth. Preferably, rotating shaft 440 is a hollow tube that is capable of routing cable 450 from a circuit board 451 to arm 125. Circuit board 451 uses cable 450 to receive data from and send data to sample arm 125.

Rotating shaft 440 extends through an aperture in top plate 445 to couple with arm 125. A grounding retainer 464 may be attached to top plate 445 in order to secure a ground wire.

Up/down flag 485 is attached to top plate 445. Up/down flag 485 may be detected by an up/down sensor 490 on circuit board 451. Up/down flag 485 may be used to detect a top dead position when moving portion 480 (FIG. 6) has moved to the top position.

Figure 10:
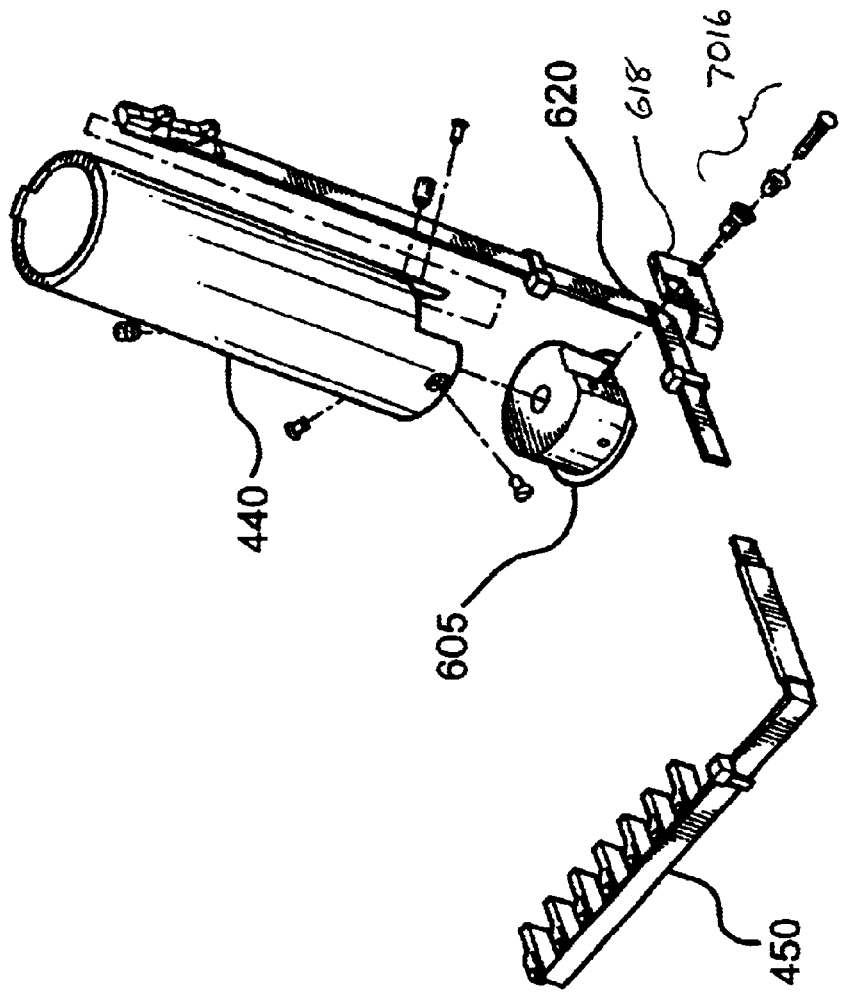
FIG. 10 is an exploded view of a subassembly of an arm drive assembly according to a preferred embodiment of the present invention.

FIG. 10 is an exploded view of rotating shaft 440 and some related components according to a preferred embodiment of the invention. FIG. 10 includes rotating shaft 440, bushing 605, cable 450, and retainer 618. Bushing 605 couples rotating shaft 605 to rotational motor 430. Using a ninth set of fasteners 7016, a retainer 618 may be attached to bushing 605 at attachment point 620. Cable 450 can be located between retainer 618 and bushing 605. This can provide a strain relief for cable 450 at attachment point 620. Preferably, cable 620 is disposed at a right angle at attachment point 620. Referring back to FIG. 7, when arm drive assembly 210 is assembled, cable 450 may wraps around rotating shaft 440 above middle plate 435. Cable 450 may exit at the top of rotating shaft 440.

Figure 9A:
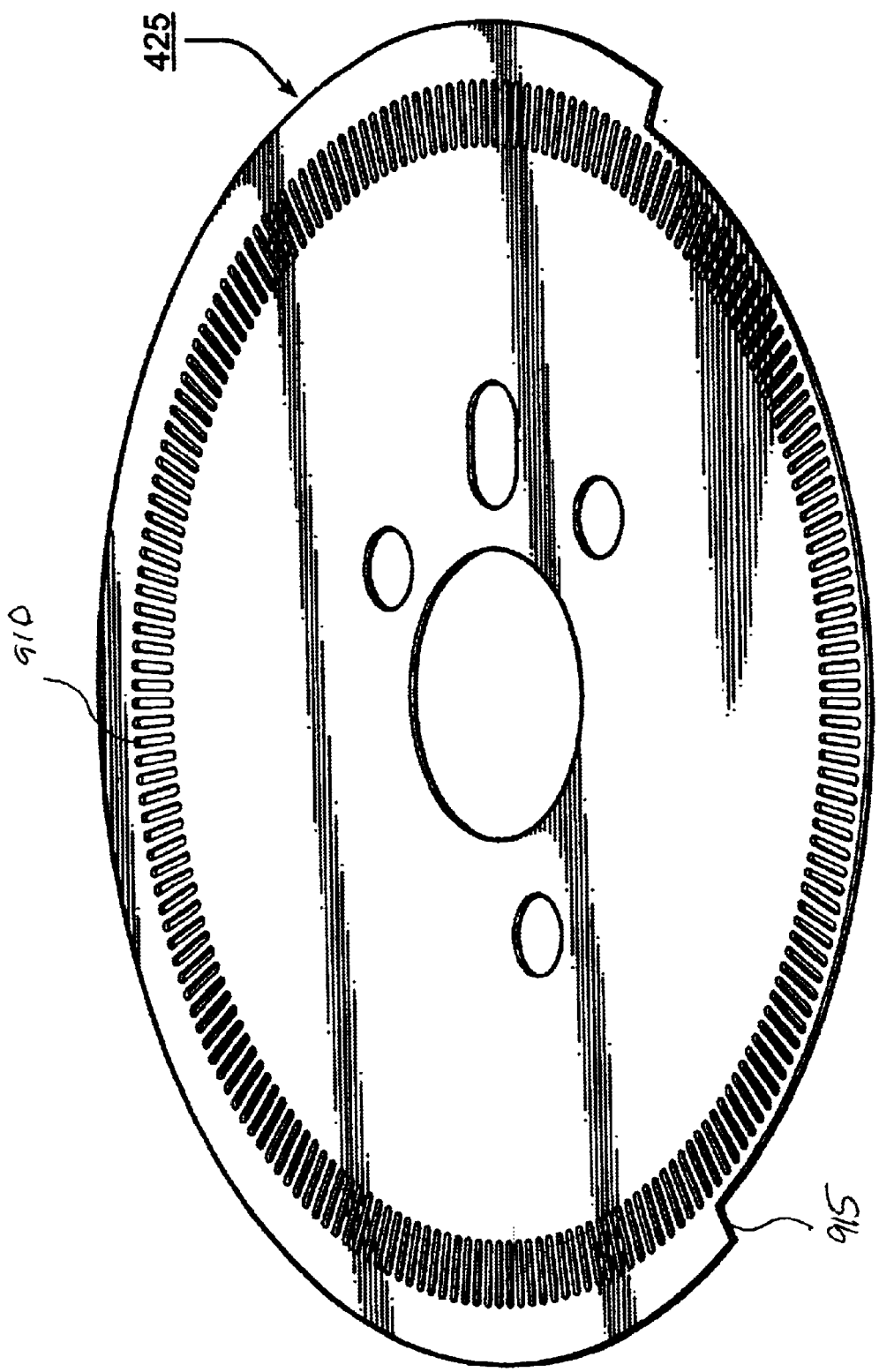
FIG. 9A is an isometric view of an encoder wheel according to a preferred embodiment of the invention.

FIG. 9A is an isometric view of a preferred embodiment of rotation indicator 425. In this embodiment, rotation indicator 425 is a so-called encoder wheel. Rotation indicator 425 can have various shapes; preferably it is a circular disk. Rotation indicator 425 has a number of fine slits 910 on its circumference for breaking a light beam or light rays. Other means for detecting a light beam or light rays could be employed.

In a preferred embodiment, rotation indicator 425 is used in conjunction with rotation sensor 415 and home sensor 420 to monitor the position of arm rotational motor 430. For example, a control signal may command arm rotational motor 430 to rotate a number of steps clockwise or counterclockwise. Rotation sensor 415 monitors the rotation based on light breaking the slits in rotation indicator 425. If the sensed rotation is different from the commanded rotation, an error signal is sent to control electronics module 235 (FIG. 2) so that a correction can be made. Home sensor 420 may monitor rotation sensor 415 to determine a home position of arm rotational motor 430 in a similar fashion. Referring to FIG. 9A, a home position might be defined by an edge 915. When edge 915 is detected, home sensor 420 determines that arm rotational motor 430 is in the home position.

Figure 9B:
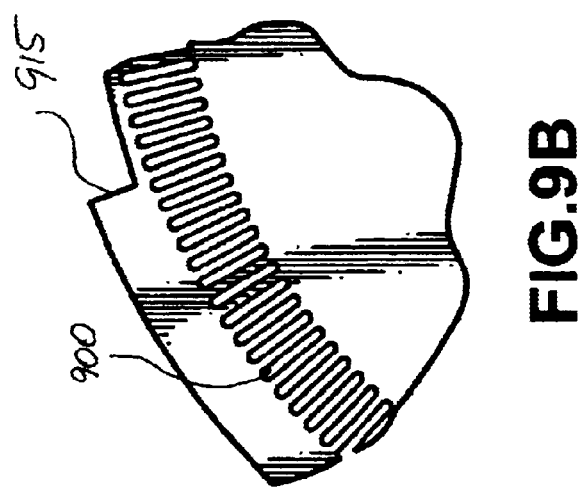
FIG. 9B is an enlarged view of an encoder wheel according to a preferred embodiment of the present invention.

FIG. 9B shows an enlarged view of a portion of rotation indicator 425 according to a preferred embodiment of the invention. Preferably, slits 900 are equally spaced along a circumference of rotation indicator 425. Slits 900 can have various shapes, including rectangular, circular, triangular, and so forth. Preferably, slits 900 are oblong. An aperture is cut along the circumference of rotation indicator 425 in order to define edge 915.

Figure 11:
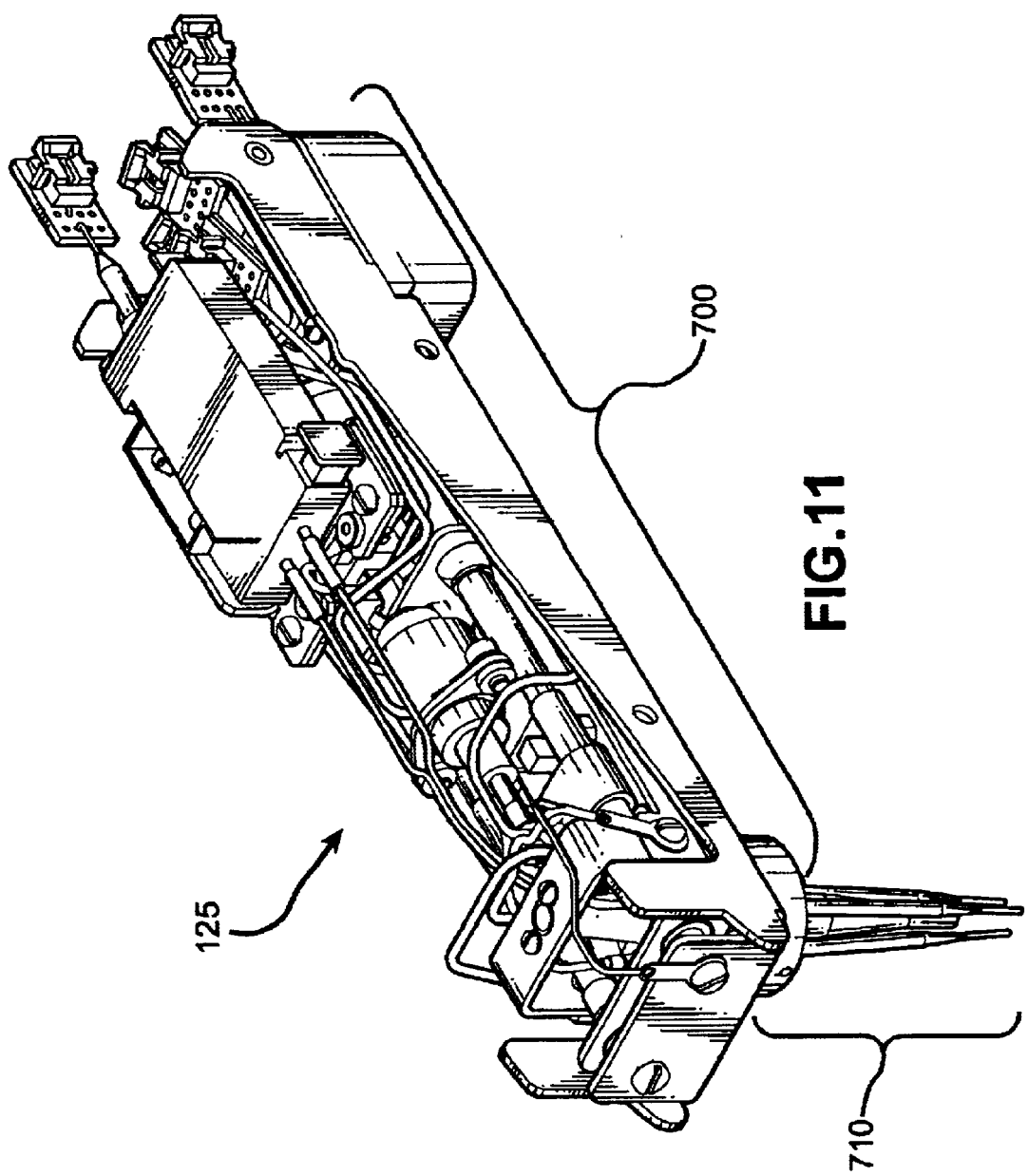
FIG. 11 is an isometric view of an arm according to a preferred embodiment of the present invention.

FIG. 11 is an isometric view of arm 125 with the cover removed. Arm 125 includes horizontal portion 700 and gripper device 710. According to an embodiment, horizontal portion 700 is rotated and raised and lowered. Preferably, horizontal portion 700 is rotated by arm rotational motor 430 and is raised and lowered by arm linear actuator. motor 405. Gripper device 710 is controlled to grasp objects.

Figure 12:
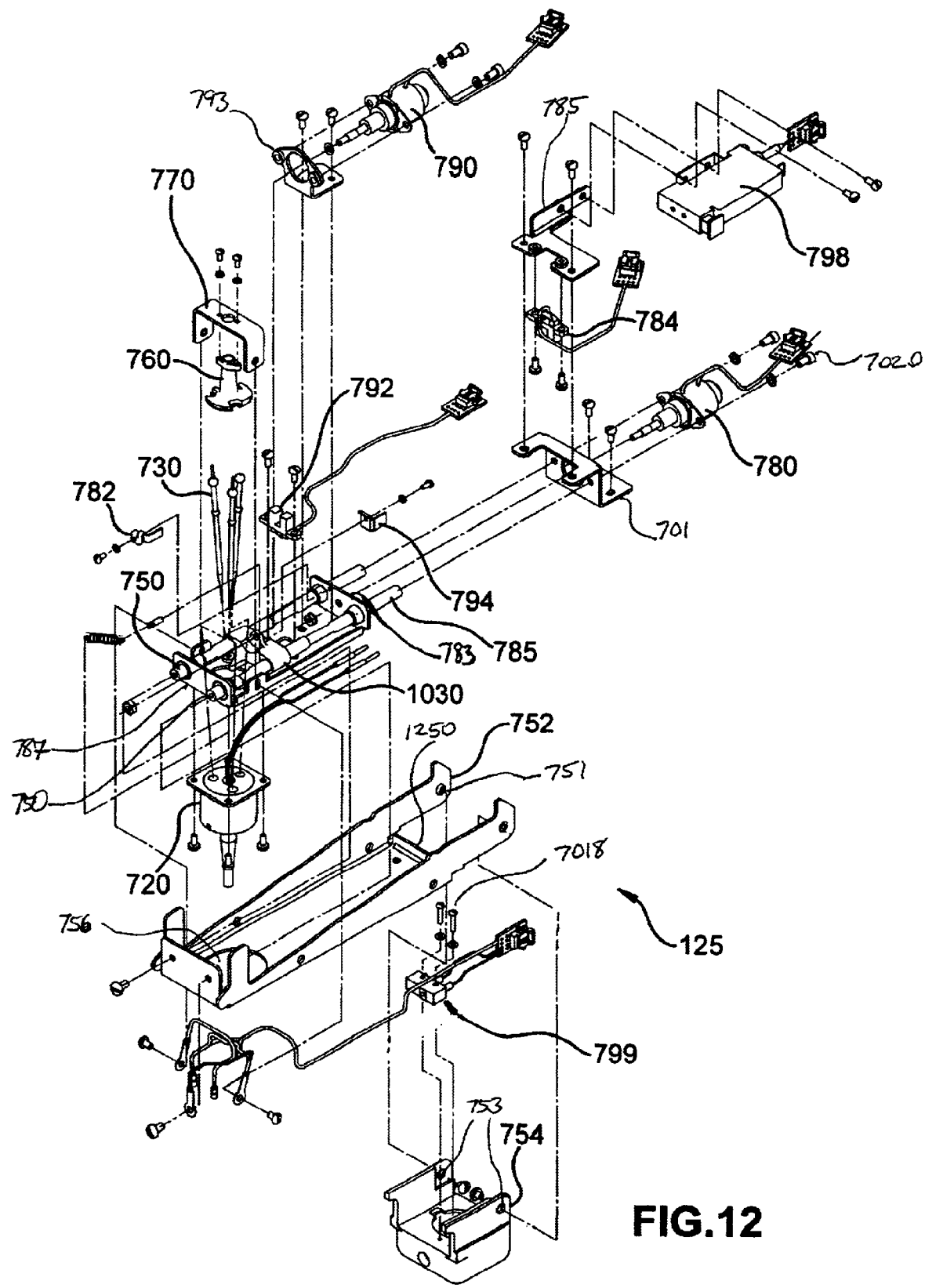
FIG. 12 is an exploded view of an arm 125 according to a preferred embodiment of the present invention.

FIG. 12 is an exploded view of sample arm 125 according to a preferred embodiment of the invention. Moving from the bottom to the top, the major components of sample arm 125 are: mounting block 754; arm chassis 752; gripper body 720; gripper fingers 730; slide assembly 1030; slide shaft 750; arm longitudinal motor 780; and gripper actuator motor 790.

Starting at the bottom of arm 125, the various components of arm 125 are mounted in arm chassis 752. Arm chassis 752 could have various shapes. Preferably, arm chassis 752 has a generally rectangular shape. Arm chassis 752 rotates as arm 125 rotates. Arm chassis 752 moves up and down as arm 125 raises and lowers. Arm chassis 752 is attached to mounting block 754. Arm chassis 752 could be attached to mounting block 754 in various manners, including screws, nuts/bolts, rivets, welds, and so forth. Preferably, arm chassis 752 is attached to mounting block 754 by protrusions 751 that insert into holes 753.

Arm 125 may include a tilt detector 799. Tilt detector 799 is attached to mounting block 754 using a tenth set of fasteners 7018. Tilt detector 799 may be used to determine when arm 125 is not horizontal, such as when arm 125 hits an obstruction. Tilt detector 799 may be used as a safety feature to protect autosampler 100 and a user.

Gripper body 720 feeds through an aperture 756 in arm chassis 752 at one end of gripper body 720. At the other end, gripper body 720 attaches to a fixed bottom 787 under slide assembly 1030. Slide assembly 1030 is mounted on slide shafts 750. Slide shafts 750 are preferably solid or hollow shafts that slide assembly 1030 can move along. Preferably, gripper body 720 remains stationary as slide assembly 1030 moves along slide shafts 750.

When arm 125 is assembled, fingers 730 protrude from the bottom of gripper body 720. The top ends of gripper fingers 730 are held secure by finger retainer 760 and bracket 770. The various components of gripper device 710 are discussed in greater detail below.

Gripper actuator motor 790 is mounted to slide shafts 750 to the rear of slide assembly 1030. A bracket 793 may be placed between slide assembly 1030 and gripper actuator motor 790. According to an embodiment, gripper actuator motor 790 is capable of moving slide assembly 1030 in and out along slide shafts 750. Preferably, gripper actuator motor 790 moves slide assembly 1030 in order to engage the gripper fingers 730 Further details are provided below.

Arm longitudinal motor 780 is attached to motor bracket 701 using an eleventh set of fasteners 7020. Motor bracket 770 attaches to the ends of slide shafts 750 using an eleventh set of fasteners 7020. According to an embodiment, arm longitudinal motor 770 is capable of moving slide shaft 750 longitudinally (in and out). Other components coupled to slide shafts 750, such as slide assembly 1030 and gripper body 720, move with slide shafts 750. In other words, arm longitudinal motor 780 may be used to move the entire arm 125 in and out.

Preferably, longitudinal movement of arm 125 is provided by sending electrical pulses or steps to arm longitudinal motor 780. The exact position is monitored by maintaining a count of these steps. A sensor may be used to check a present position count against the actual position. Periodically, sample arm 125 may be caused to return to the home position based on a present count. A sensor may then be used to confirm that the home position has actually been reached. According to one embodiment, each step causes about 0.00002 inches of displacement by the motor. Preferably, gripper actuator motor 790 is controlled in a manner similar to arm longitudinal motor 780. Sensors may be used to check the position of gripper actuator motor 790 as well.

The preferred embodiment of FIG. 12 includes components for monitoring position including sensor amplifier 798, home sensor 784, home flag 782, open/close sensor 792, and open/close flag 794.

Sensor amplifier 798 is mounted to sensor amplifier bracket 785. Home sensor 784 is mounted to sensor amplifier bracket 785. Sensor amplifier bracket 785 is mounted to motor bracket 770. Home flag 782 is mounted to a brace 783 that is fixably attached to slide shafts 750. Home flag 782 moves as slide shafts 750 move longitudinally.

Open/close sensor 792 is mounted to a fixed bottom 787 under slide assembly 1030 so that open/close sensor remains stationary as slide assembly 1030 moves. Open/close flag 794 is mounted to a rear portion of slide assembly 1030 so that open/close flag 794 moves as slide assembly 1030 moves.

Sensor amplifier 798 may be an electrical component for amplifying or otherwise processing a signal to be processed by control module 235 or another controller or signal processor. Preferably, sensor amplifier 798 is a fiber optic amplifier for amplifying optic signals. Home sensor 784 and open/close sensor 792 could be any component capable of sensing a position. Preferably, home sensor 784 and open/close sensor 792 are optic sensors.

Home flag 782 and open/close flag 794 could be any device or component capable of providing information or data regarding the position of a sensed device. Preferably, home flag 782 and open/close flag 794 have a light blocking member for blocking a light beam.

According to a preferred embodiment of arm 125, home sensor 784 and home flag 782 can be used to detect the longitudinal home position of arm 125. Home flag 782 moves with slide shafts 750 as they move in and out. When arm longitudinal motor 780 returns to a home position, home flag 782 is detected by home sensor 784. This may result from a light blocking member of home flag 782 breaking a beam projected between two shoulders of home sensor 784.

According to an embodiment, home sensor 784 and home flag 782 are used to recalibrate the home position periodically. Preferably, calibration of the longitudinal home position occurs each time sample arm 125 retrieves a sample pan and inserts the sample pan in cell 150. Calibration of the home position may occur at different times.

According to a preferred embodiment of arm 125, open/close sensor 792 and open/close flag 794 can be used to detect the engagement of the gripper device 710 on arm 125. As will be discussed below, movement of slide assembly 1030 causes gripper device 710 to engage and disengage. Open/close flag 794 moves as slide assembly 1030 moves in and out. Open/close sensor 792 can be located to detect open/close flag 794 at a position corresponding to a predetermined state of engagement of gripper device 710 (e.g., fingers open or closed). Thus, when open/close flag 794 is detected by open/close sensor 792, the gripper device is in the predetermined state of engagement.

The operation of the preferred arm 125 of FIG. 12 can be described as follows. Arm longitudinal motor 780 moves sample arm 125 in and out. Sample arm 125 may be moved in and out (and rotated or raised or lowered, as previously discussed) to retrieve sample pans, insert sample pans, dispose of sample pans, and so forth. Gripper actuator motor 790 controls gripper device 710 in order to grasp and release sample pans, reference pans, and so forth. Gripper device 710 is discussed in further detail below.

FIG. 11 is an isometric view of an arm 125 including a gripper device 710 according to a preferred embodiment of the invention. Referring now to FIG. 12, the preferred gripper device 710 includes gripper body 720, gripper fingers 730, finger retainer 760, and bracket 770.

Gripper body 720 holds gripper fingers 730. Gripper fingers 730 could be inserted into gripper body 720 in various fashions. For example, gripper fingers 730 could be inserted into the bottom of gripper body 720. Preferably, gripper fingers 730 are inserted into the top of gripper body 720. In the preferred embodiment of sample arm 125, gripper body 720 is attached to a fixed bottom 787 under slide assembly 1030. Gripper fingers 730 can be inserted from the top of slide assembly 1030, as indicated in FIG. 12. This is a significant advantage, as will be discussed further below.

Gripper fingers 730 are used to touch and/or grasp objects. According to an embodiment, gripper fingers 730 are used to grasp sample pans. In a preferred embodiment, gripper fingers 730 may be used to detect sample pans and to perform calibration operations. Gripper device 710 may have various numbers of gripper fingers 730. Preferably, gripper device 710 has three fingers.

Generally, the operation of gripper device 710 is as follows. A gripper actuator, such as gripper actuator motor 790, causes fingers 730 to open or close. Accordingly, arm 125 can be rotated to a position to grasp or release an object, such as a sample pan or reference pan.

In a preferred embodiment of gripper device 710, the gripper fingers 730 are held in place by finger retainer 760. In the preferred sample arm 125 of FIG. 12, finger retainer 760 may be secured onto arm 125 using bracket 770.

FIG. 24 is an isometric view of a preferred embodiment of finger retainer 760. Finger retainer 760 includes aperture 1105 for feeding a cable (e.g., cable 850 in FIG. 14, discussed below) and slots 1110. Slots 1110 may used to holding fingers 730 in place. In a preferred embodiment, slots 1110 are used to hold two electrically conductive front fingers 730 (see FIG. 12) in place. The two electrically conductive front fingers 730 can carry a current used by gripper device 710 for pan location and for calibration.

Figure 15A:
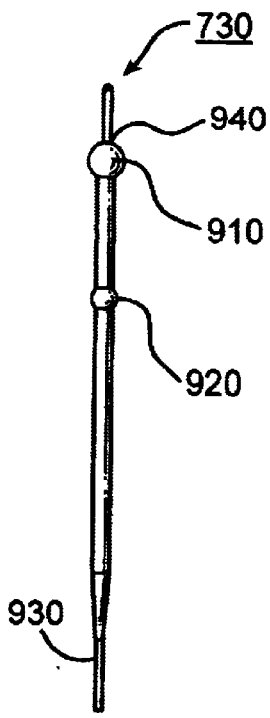
FIG. 15A is a front view of a gripper finger according to a preferred embodiment of the present invention.

Various designs could be used for gripper fingers 730 of gripper device 710. FIG. 15A is a front view of a preferred embodiment of gripper finger 730. Gripper finger 730 includes an upper ball 910, a lower ball 920, and a grasping end 930. Grasping end 930 is used to grasp or touch objects, such as sample pans.

According to one embodiment, gripper fingers 730 are approximately 2.5 to 4.0 inches long, preferably about 3.4 inches long. Upper ball 910 is preferably larger than lower ball 930. According to one embodiment, upper ball 910 is a sphere with a radius between 0.05 and 0.3 inches, preferably about 0.19 inches. According to an embodiment, lower ball 930 is a sphere with a radius between 0.03 and 0.28 inches, preferably about 0.14 inches.

Gripper fingers 730 can be made of various materials. Gripper fingers 730 can be constructed of a conductive material to facilitate electrical sensing. Alternatively, gripper fingers can be constructed of an elastic material. When constructed of an elastic material, fingers 730 can be designed for a specific gripping force by controlling fingers 730 so that the target grip is slightly smaller than the grasped object. The compliance of the fingers 730 may provide a gripping force that is proportional to the elasticity of the bending fingers.

If constructed of a conductor, fingers 730 can be used for electrical sensing. A conductive object can be detected by measuring its resistance; a nonconductive object can be detected by measuring its dialectric properties. Preferably, fingers 730 are constructed of 300 series stainless steel.

According to an embodiment, finger 730 also has groove 940. Groove 940 permits the portion of the finger above upper ball 910 to be hand-removed. As will be discussed below, a preferred embodiment of gripper 710 uses two fingers 730 for electrical sensing. Accordingly, the tops of two fingers 730 may be used to make an electrical contact. For a remaining finger(s), the portion of the finger above upper ball 910 can be removed. Referring back to the preferred embodiment of FIG. 12, it can be seen that one of the fingers 730 has had this portion removed.

Figure 15B:
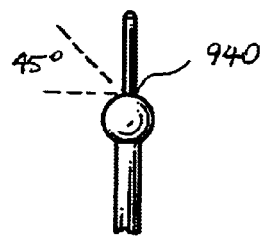
FIG. 15B is an enlarged view of a portion of a gripper finger according to a preferred embodiment of the present invention.

FIG. 15B shows an enlarged view of a preferred groove 940. Groove 940 is cut at an angle of approximately 45 degrees. According to an embodiment, groove 940 is machined at 45 degrees +5 degrees. Preferably, groove 940 has a depth of about 0.004 inches.

Figure 13:
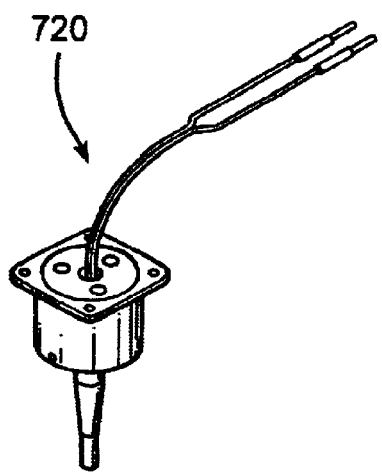
FIG. 13 is an isometric view of a gripper body according to a preferred embodiment of the present invention.
Figure 14:
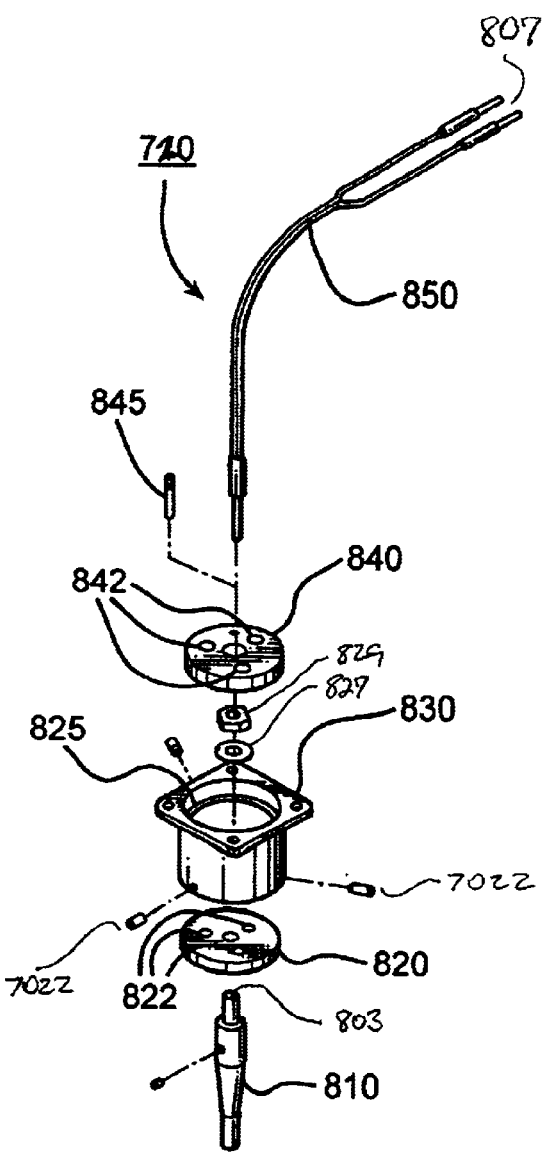
FIG. 14 is an exploded view of gripper body according to a preferred embodiment of the present invention.

FIG. 13 is an isometric view of a preferred embodiment of gripper body 720. FIG. 14 is an exploded view of a preferred embodiment of gripper body 720. Gripper body 720 may include sensor assembly 810, lower flat member 820, housing 830, upper flat member 840, protruding member 845, and optic cable 850.

Optic cable 850 threads through center apertures in upper flat member 840 and lower flat member 820. Optic cable 850 inserts into the open end 803 of optic sensor lens assembly 810. According to an embodiment, a forked upper end 807 of optic cable 850 includes a lead for transmitting a light beam and a lead for receiving reflected light. Referring back to FIG. 12, forked upper end 807 is preferably connected to sensor amplifier 798. Optic cable 850 is preferably a fiber optic cable. Preferably, sensor assembly 810 focuses a light beam between fingers 730.

Returning to FIG. 14, sensor assembly 810 attaches to an aperture in lower flat member 820. Sensor assembly 810 is preferably an optical sensor that receives light transmitted from optic cable 850. Sensor assembly 810 also transmits reflected light back up optic cable 850. Preferably, sensor assembly 810 is disposed between fingers 730 when fingers 730 are inserted into gripper body 720.

Upper flat member 840 rests against flange 825 in housing 830. Preferably, upper flat member 840 is rotatable within flange 825. Lower flat member 820 is fastened with a twelfth set of fasteners 7022 to the open bottom of housing 830. Upper flat member 840 and lower flat member 820 can have various shapes. Preferably, upper flat member 840 and lower flat member 820 are circular disks. They may be made of various nonconductive materials, such as Delron™, a plastic manufactured by Dupont Corp.

The housing 830 retains upper flat member 840 and lower flat member 820. Nut 829 and washer 830 are used to secure various components of gripper body 720. Upper flat member 840 and lower flat member 820 are used to retain gripper fingers 730.

There are several upper apertures 842 located along an inner circumference of upper flat member 840. There are several lower apertures 822 located along an inner circumference of lower flat member 820. When each finger 730 is inserted through the apertures in the two flat members (840 and 820), upper ball 910 rests against an upper aperture 842, and lower ball 920 rests against a lower aperture 822.

Preferably, upper flat member 840 has a larger outer circumference and a larger inner circumference than lower flat member 820. When inserted, fingers 730 may tilt inwardly in the amount of 1–5 degrees. Preferably, fingers 730 tilt inwardly about 3 degrees.

When the fingers 730 are inserted in gripper body 720, rotation of the upper flat member 840 relative to fixed lower flat member 820 causes fingers 730 to open and close. Lower ball 920 pivots about lower aperture 822 in lower flat member 820. Fingers 730 open and close in a manner that grasping ends 930 (see FIG. 15A) tend to define a common circumference. In an embodiment where there are three fingers 730, the tips of the grasping fingers are generally equidistant (roughly defining an isosceles triangle). This characteristic means that gripper device 710 tends to center an object within its grasp. This is a very beneficial feature that improves pan location and reduces the incidence of crimped/damaged pans. It also reduces the incidence of pans sticking to fingers, thus improving pan insertion.

When upper flat member 840 is rotated to open fingers 730, the grasping ends 930 rotate in a common direction to define a larger common circumference. This characteristic means that gripper device 710 will tend to rotate an object within its grasp when the object is being released. This is another very beneficial feature that reduces the incidence of pans sticking to fingers, thus improving pan insertion.

Figure 16:
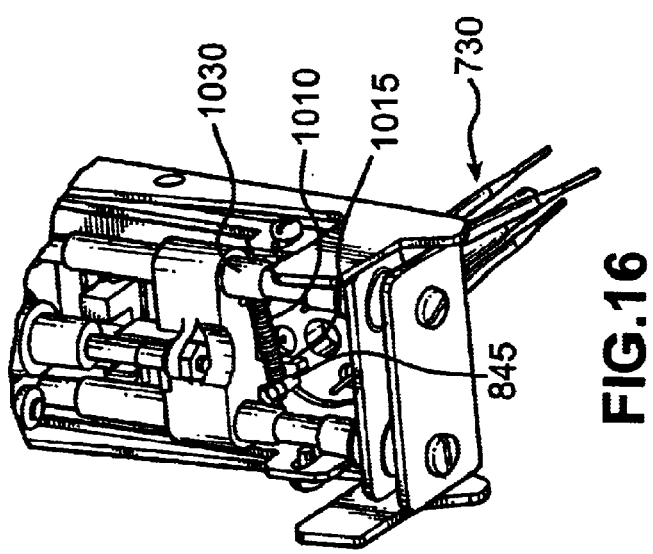
FIG. 16 shows a portion of an arm with a gripper device in an open position according to a preferred embodiment of the present invention.

FIGS. 16-23 further illustrate the operation of a preferred embodiment of gripper device 710. FIG. 16 shows a top view of a portion of arm 125 with the preferred gripper device 710 in the open position. A gripper control assembly makes fingers 730 open by causing rotation of upper flat member 840 relative to lower flat member 820. Various designs for a gripper control assembly could be employed to cause this rotation.

In the preferred embodiment in FIG. 16, the gripper control assembly (hereinafter gripper control assembly 1050) comprises a cam-type device including slide assembly 1030, displacing member 1015, protruding member 845, and bias member 1010.

Bias member 1010 is coupled to upper flat member 840. Bias member 1010 provides a rotational bias or resistance. When the gripper control assembly 1050 is not engaged, fingers 730 tend towards a nominal position (e.g., closed or open, preferably closed). According to a preferred embodiment, bias member 1010 is a spring attached to protruding member 845. Alternative devices for imparting a rotational bias, such as a rubber band type element, could be employed.

Protruding member 845 is attached to upper flat member 840. Protruding member 845 could be any shape that protrudes from upper flat member 840. Preferably, protruding member 845 is a post. As shown in the preferred embodiment of FIG. 16, protruding member 845 is engaged by bias member 1010 and displacing member 1015.

Displacing member 1015 engages protruding member 845 in order to rotate upper flat member 840. Displacing member 1015 could have any shape capable of imparting this rotation. Preferably, displacing member 1015 is a foot-shaped member that is part of or attached to longitudinal slide assembly 1030. The preferred foot-shaped member 1015 includes a sloped portion on one side.

Slide assembly 1030 extends or retracts so that displacing member 1015 engages protruding member 845. When this occurs, upper flat member 840 is rotated and fingers 730 open or close, as previously described. In FIG. 16, longitudinal slide 1030 has extended to rotate upper flat member 840 in a counter-clockwise direction, opening fingers 730.

Figure 17:
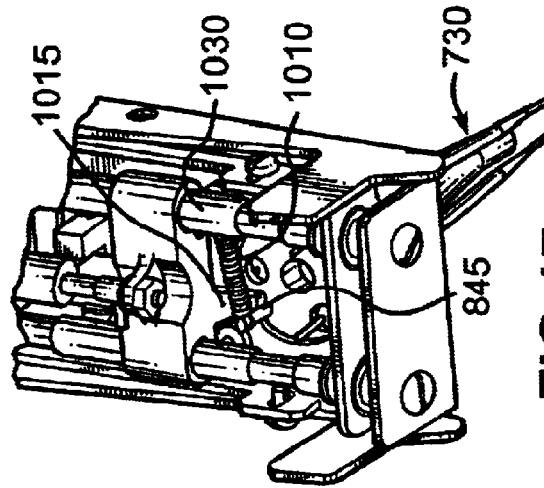
FIG. 17 shows a portion of an arm with a gripper device in a closed position according to a preferred embodiment of the present invention.

FIG. 17 shows a top view of a portion of arm 125 with the preferred gripper device 710 in the closed position. Slide assembly 1030 has retracted so as to permit upper flat member 840 to rotate in the clockwise position, closing fingers 730.

Figure 18:
FIG. 18 is a bottom view of an arm with a gripper device in a closed position according to a preferred embodiment of the present invention.

FIG. 18 is a bottom view of a preferred embodiment of arm 125 with the preferred gripper device 710 in the closed position. Sensor assembly 810 is located in between fingers 730. Fingers 730 are generally equidistant, roughly defining an isosceles triangle.

FIG. 19 is a side view of a portion of arm 125 with the preferred gripper device 710 in the closed position. Sensor assembly 810 is disposed in between the grasping ends 930 of fingers 730.

FIG. 20 is a top view of a portion of arm 125 with the preferred gripper device 710 in the closed position. Slide assembly 1030 has retracted to allow gripper device 710 to close.

Figure 21:
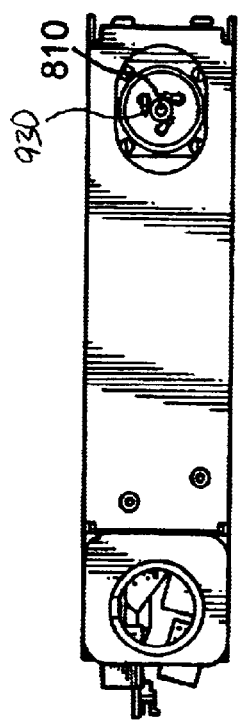
FIG. 21 is a bottom view of an arm with a gripper device in an open position according to a preferred embodiment of the present invention.

FIG. 21 is a bottom view of a portion of arm 125 with the preferred gripper device 710 in the open position. The tips of grasping ends 930 are generally equidistant, roughly defining an isosceles triangle. It can be seen that as gripper device 710 opens, the grasping ends 930 move angularly as well as radially. In other words, as gripper device 710 opens, the grasping ends 930 not only move outwardly; they also rotate. This characteristic means that gripper device 710 will tend to rotate objects as they are released.

FIG. 22 is a side view of a portion of arm 125 with the preferred gripper device 710 in the open position. Sensor assembly 810 is disposed in between the grasping ends 930 of fingers 730.

FIG. 23 is a top view of a portion of arm 125 with the preferred gripper device 710 in the open position. Slide assembly 1030 has extended to allow gripper device 710 to close.

Several additional beneficial aspects to the preferred gripper device 710 and gripper control assembly 1050 can be seen by referring back to FIG. 12. Gripper body 720 is attached to sliding carriage 787. Slide assembly 1030 is mounted on rails 750. Slide assembly 1030 provides a cam-type action to control the gripper device 710 as previously described. Gripper body 720 is installed before fingers 730 are installed.

Fingers 730 are installed by dropping them in between rails 750 and into gripper body 720. This is an extremely beneficial aspect of the invention because users can replace gripper fingers 730 without removing gripper body 720. After the fingers are inserted, only finger retainer 760 and finger retainer bracket 770 need to be removed. This is a significant improvement over prior designs.

There is another benefit. FIG. 12 also shows gripper actuator motor 790, which provides the displacement (translated in the cam operation) that engages gripper device 710. Once gripper actuator motor 790 stops, it is the spring bias action of bias member 1010 on protruding 845 that provides the gripping action of fingers 730. Consequently, fingers 730 tend to grip objects with an even, fairly constant amount of force. This is a significant advantage. The amount of force is based on the spring constant of spring 1010. If it were desirable to vary the amount of force, a spring with a nonlinear spring constant can be selected.

Having described a preferred embodiment of gripper device 710, it can be seen that gripper device 710 can be a dual-sensed device. There is the fiber optical sensor (e.g., sensor assembly 810) disposed between gripper fingers 730. There is an electrical sensor based on two conductive fingers.

According to a preferred embodiment, these sensors can be used for both pan location (or "pan sensing") and calibration purposes, to be discussed further below. During pan location, the use of two sensors provides a redundant pan location capability that improves performance. During calibration, one sensor can be employed for calibration in a first dimension (e.g., the vertical z-axis) and the other can be employed for calibration in the remaining two dimensions (e.g., the horizontal x and y axes). Thus, accurate and precise calibration in three dimensions can be performed.

Regarding electrically-sensed pan location, the electrical sensor can be used to sense the presence of a conductive or nonconductive pan. Resistance or dialectric properties can be measured. A measured property can be compared to a threshold in order to determine if fingers 730 are grasping a pan. Electrical sensing thresholds can be varied based on the pan type that is being used.

According to one embodiment, these thresholds can be adjusted using a "learning" or "teaching" mode that recalculates the thresholds for a given pan type. The coding of an electrical sensing algorithm (which could reside in control module 235 (See FIG. 2)) for implementing this capability is well within the skill of the ordinary artisan.

Regarding optically-sensed pan location, reference is made to FIGS. 12 and 14. A preferred fiber optical sensor may comprise sensor assembly 810, optic cable 850, and fiber optic amplifier 798. The overall assembly is hereafter referred to as sample arm fiber optic sensor 1000. Fiber optic amplifier 798 may be a high precision fiber optic amplifier #E3X-NH11. Fiber optic cable 850 may be a fiber optic cable E32-D32. Both of the above are manufactured by Omron Corporation.

The operation of sample arm fiber optic sensor 1000 for pan location is now described. Fiber optic amplifier 798 creates a light beam (preferably an LED-generated infrared beam) that is transmitted by fiber optic cable 850 down to sensor assembly 810. Lens assembly 810 is mounted between gripper fingers 730 in order to project the beam in a downward direction.

The light beam intersects a pan grasped by fingers 730 and returns a reflected beam. The reflected light beam is received by sensor assembly 810 and transmitted back up fiber optic cable 850. Generally, a pan having a metallic (e.g., aluminum) cover readily reflects the light beam.

An optical sensing pan location algorithm (which may reside in fiber optic amplifier 798 or control module 235 (See FIG. 2) may compare the amplitude of the reflected beam to a threshold. If the threshold is exceeded, the algorithm may determine that a pan is present.

The above threshold may be varied so that different pan types can be detected, such as a pan with a ceramic cover or a pan with no cover at all. The optical sensing pan location algorithm may have an adaptive learning feature that permits it to auto-adjust the threshold based on different pan types. The coding of such the optical sensing pan location algorithm is well within the skill of the ordinary artisan.

Figure 28:
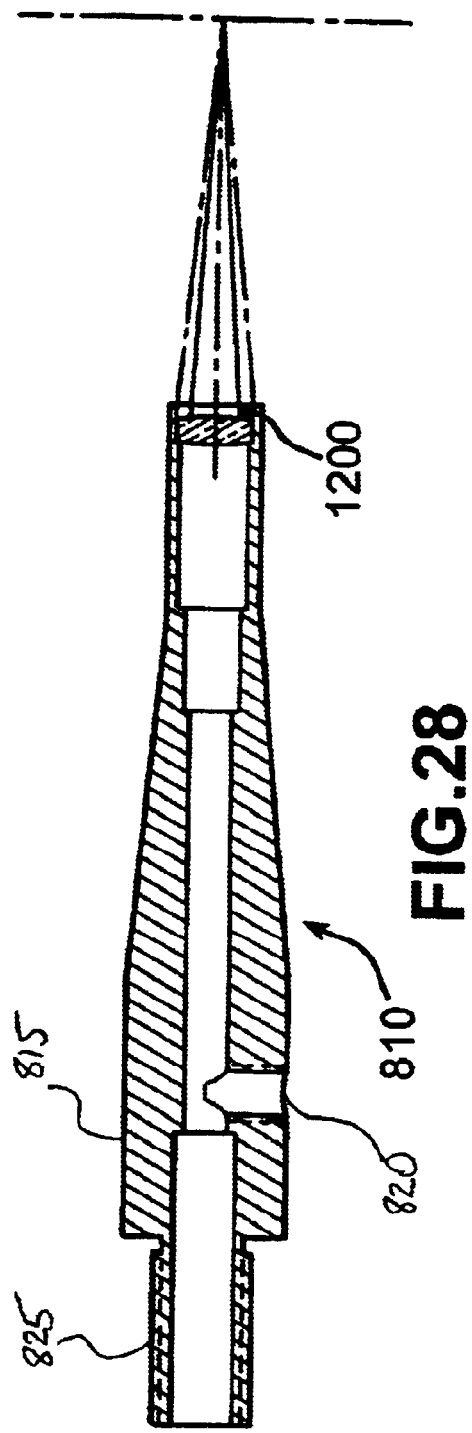
FIG. 28 is a cross-sectional side view of a sensor assembly according to a preferred embodiment of the present invention.

FIG. 27 is an isometric view of a preferred embodiment of sensor assembly 810. FIG. 28 is a side view of a preferred embodiment of sensor assembly 810. Sensor assembly 810 includes a housing 815, cable entry member 825, aperture 820, and lens 1200.

Figure 29:
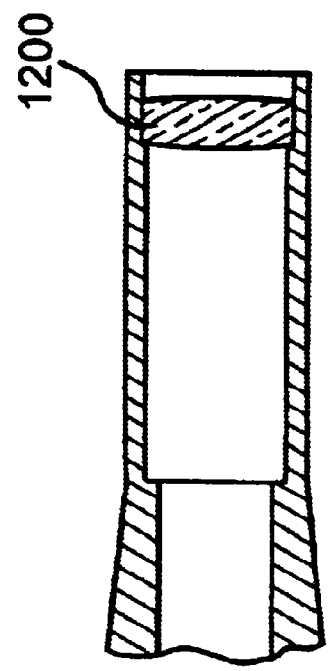
FIG. 29 is an enlarged cross-sectional side view of a portion of a sensor assembly according to a preferred embodiment of the present invention.

Housing 815 receives fiber optic cable that is fed through cable entry member 825. Aperture 820 may be used to crimp or lock down the fiber optic cable. Lens 1200 focuses a light beam carried by the fiber optic cable. Preferably, lens 1200 has a focal length of about three quarters of an inch, preferably about 0.783 inches. At this focal length, pans having a height of 0.5 to 0.75 inches can be readily detected. FIG. 29 shows an enlarged side view of a portion of a preferred sensor assembly 810.

Dual sensors in a preferred gripper device 710 are not only useful for pan location, the dual sensors can also be used for calibration. First, the geometry of autosampler 100 is discussed to set the backdrop for calibration.

Referring back to FIGS. 1 and 2, in a preferred embodiment of autosampler 100 the arm 125 is capable of a vertical displacement of about 2.0–2.5 inches in order to: retrieve a sample pan from a sample tray inside well 140; rotate a sample pan to the cell 120; insert a sample pan down into DSC cell 120; and retrieve a sample pan from cell 120 after a test cycle is complete, and so forth.

Arm 125 not only raises up and down to perform the above operations. Arm 125 rotates as well. According to a preferred embodiment, the geometry of thermal analysis instrument 90, particularly autosampler 100, is configured so that arm 125 can rotate to each of these points along a common arc of rotation. Preferably, this arc of rotation is about 6.5+0.25 inches. Other arcs of rotation could be used.

Figure 30:
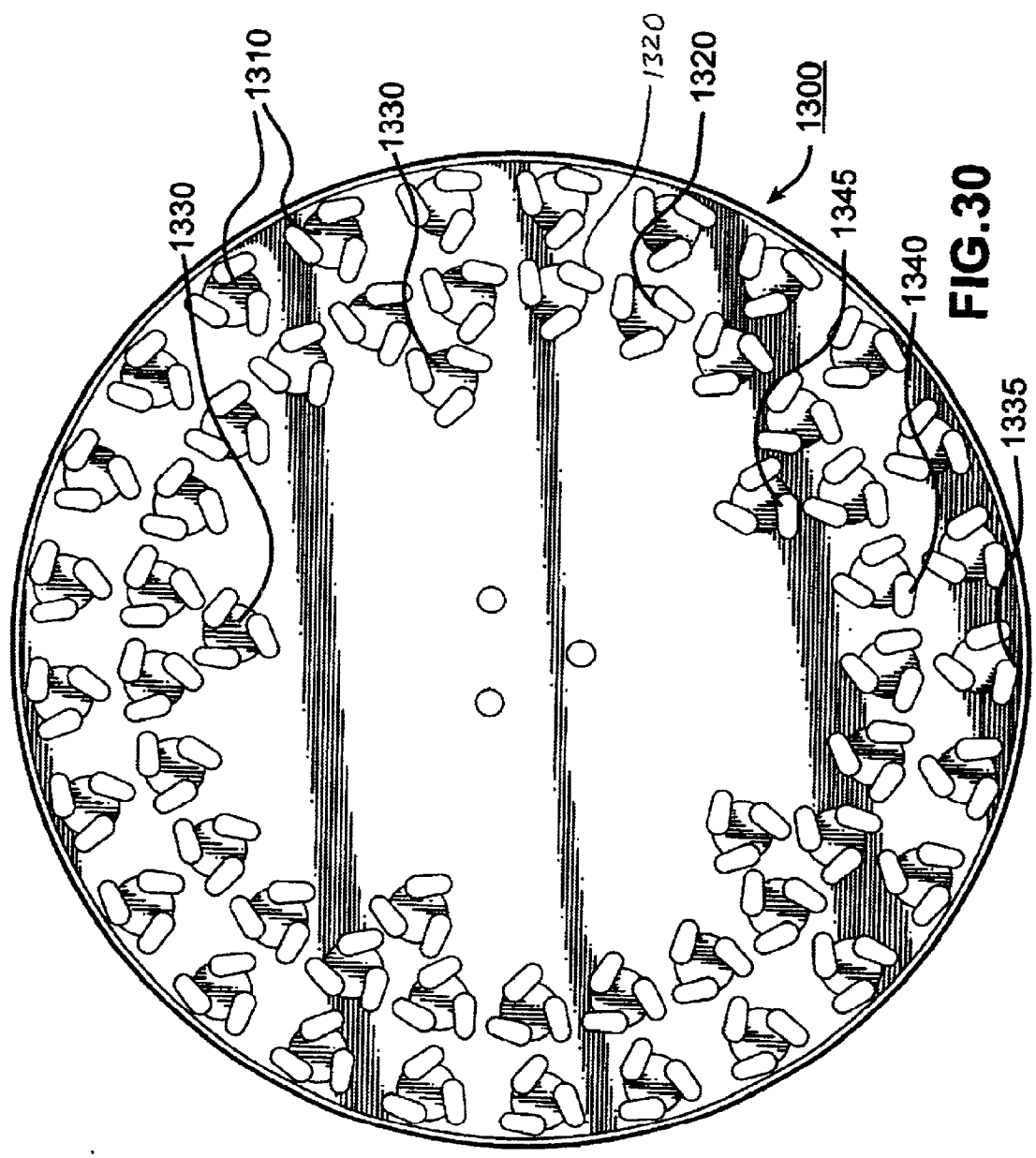
FIG. 30 is a top view of a tray according to a preferred embodiment of the present invention.

In autosampling devices, sample trays may be used to hold a number of sample pans. FIG. 30 is a top view of a preferred embodiment of a tray 1300 (also referred to as "Sample tray" 1300) that allows multiple wells 1310, 1320 and 1330 on a tray 1300 to be accessed along a common arc of rotation for arm 125. Preferably, tray 1300 is made of a black anodized aluminum.

Referring to FIG. 30, the preferred tray 1300 includes three substantially concentric rows of wells: a first outer row 1310, a second middle row 1320, and a third inner row 1330. According to an embodiment, first outer row 1310 has a first series of sample wells (e.g., sample wells #1–#25); second middle row 1320 has a second series of sample wells (e.g., sample wells #26–#50); and third inner row has a series of reference wells (reference wells #1–#5).

In a preferred embodiment, the rows are rotationally offset so that multiple wells can be accessed when at least one well is on the common arc of rotation. For example, sample well #1 1335, sample well #26 1345, and reference well #1 1345 lie along the common arc, as shown in FIG. 30. Likewise, sample well #6, sample well #31, and reference well #2 line on the common arc, and so forth.

At every fifth well (from sample well #1), at least three wells line up along the common arc: a first row sample well, a second row sample well, and a reference well. In between these locations, at least two wells line up along the common arc: a first row sample well and a second row sample.

As a result of this beneficial geometry, sample tray 1300 can be rotated so that each well can be accessed by arm 125 along the common arc. Moreover, multiple wells can be accessed.

In the preferred embodiment of sample tray 1300, there are three concentric rows of wells. However, a greater or lesser number of concentric rows could easily be used.

Figure 40:
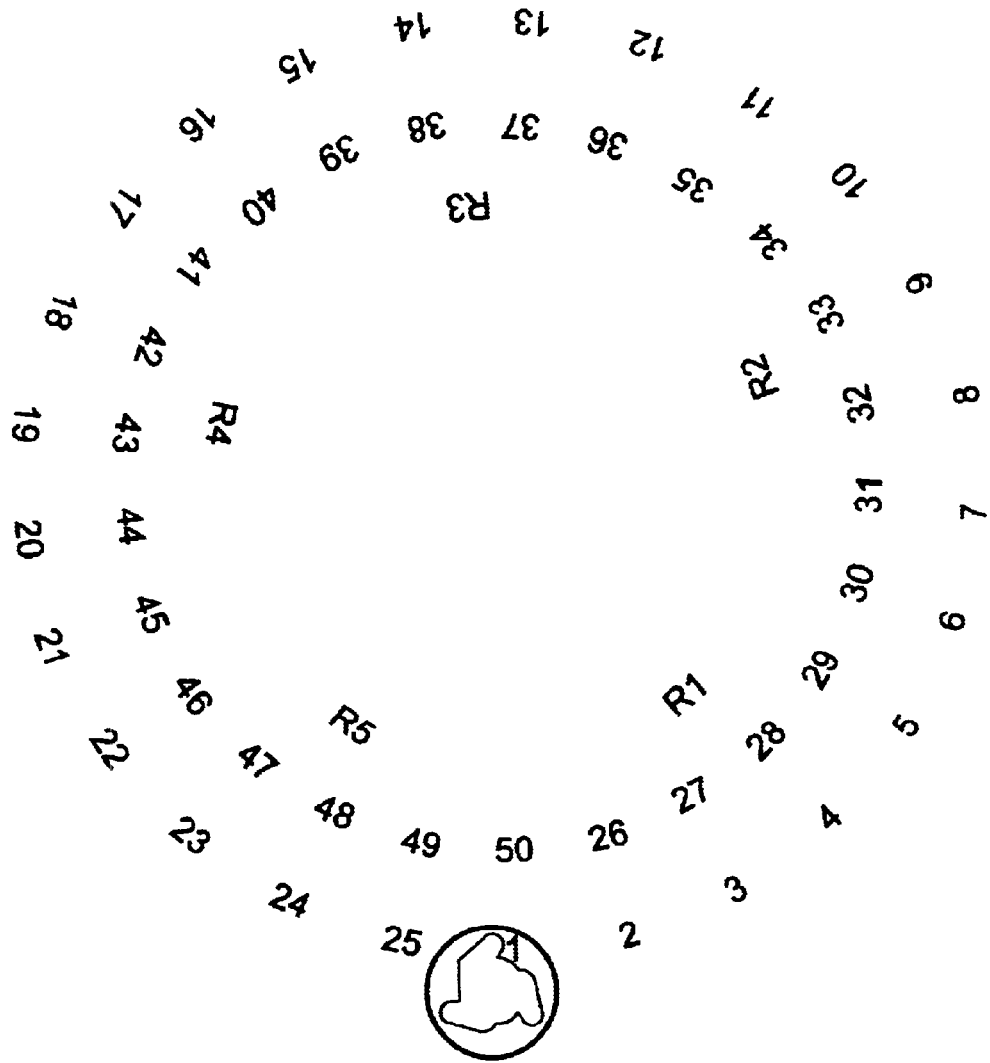
FIG. 40 shows an exemplary numbering scheme for a tray according to a preferred embodiment of the present invention.

FIG. 40 illustrates an exemplary numbering system employed for sample tray 1300 according to one embodiment. The wells of sample tray 1300 can be labeled, for example, using silk screening. Other numbering systems could be employed.

FIGS. 33, 34, and 35 show a representative well 3300 from the three rows (e.g., sample well #1 1335, sample well #26 1345, and reference well #1 1345). As can be seen from FIGS. 33-35, well 3300 includes a pan receiving portion 1360 and finger receiving portions 1370. Pan receiving portion 1360 is used to hold a pan. In a preferred embodiment, finger receiving portion 1370 receives grasping ends 930 of gripper device 710. Of course, finger receiving portion 1370 could receive the grasping ends of alternative gripper devices.

Generally, well 3300 includes a number of finger receiving portions 1370 equal to the number of fingers of a gripper device. In a preferred embodiment, there are three finger receiving portions 1370 in well 3300.

Pan receiving portion 1360 is preferably circular. Finger receiving portions 1370 are preferably oriented in a somewhat tangential manner around pan receiving portion 1360. As illustrated in FIG. 33, finger receiving portions 1370 are preferably oblong in shape with a longer dimension A and a shorter dimension B. According to an embodiment of the present invention, longer dimension A is about twice as large as shorter dimension B.

Figure 36:
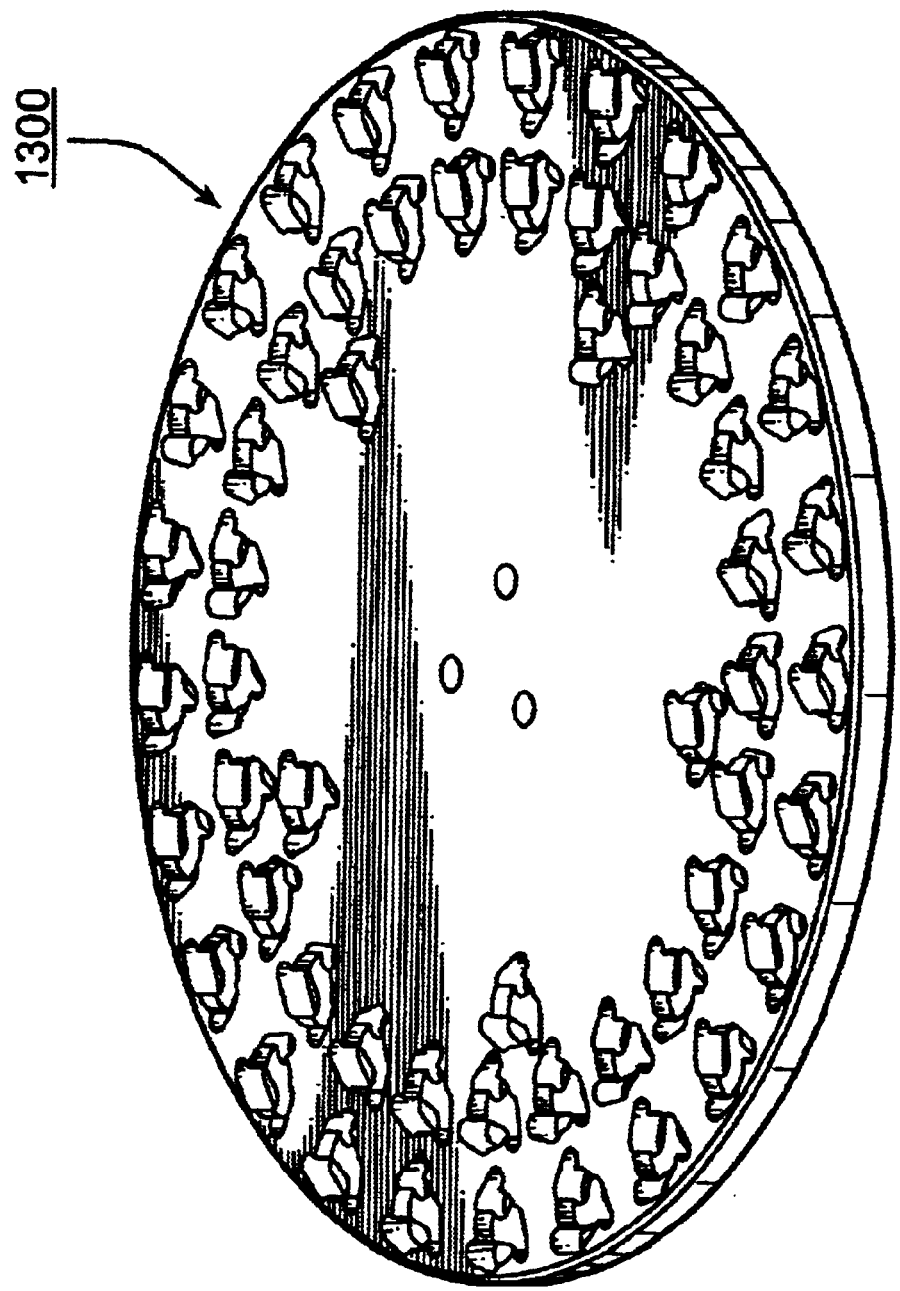
FIG. 36 is a top isometric view of a tray a according to a preferred embodiment of the present invention.
Figure 37:
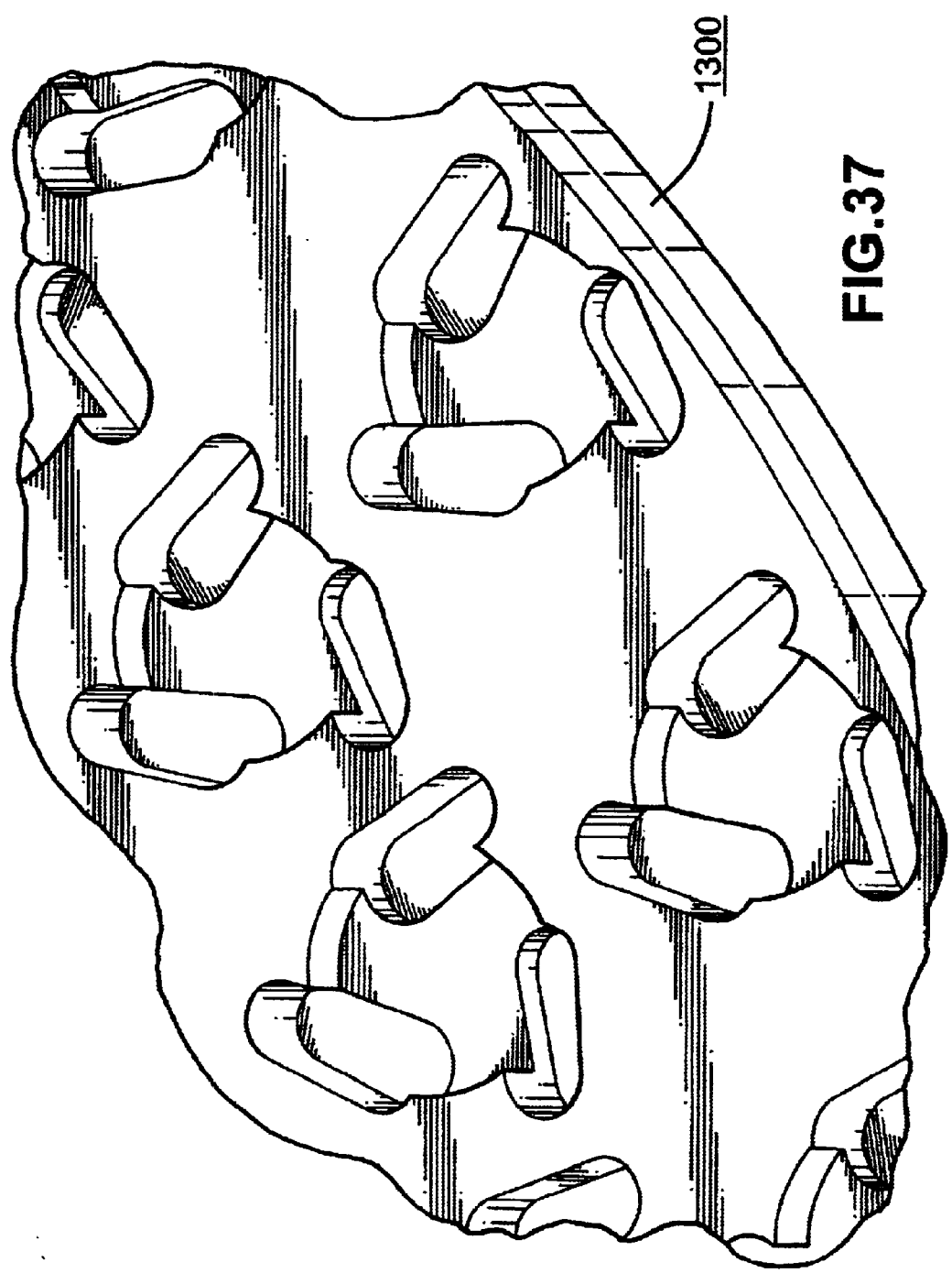
FIG. 37 is an enlarged isometric view of a tray according to a preferred embodiment of the present invention.

FIG. 36 is an isometric top view of a preferred embodiment of sample tray 1300. FIG. 37 shows an enlarged isometric view of a preferred embodiment of wells 3300 on tray 1300. FIG. 37A is a cross-sectional view of a preferred embodiment of tray 1300. As reflected in these figures, finger receiving portion 1370 may extend deeper into tray 1300 than pan receiving portion 1360. This permits gripper fingers 730 to extend below the pan for effective grasping of the pan. Referring to FIG. 37A, finger receiving portion depth 3710 is significantly deeper than pan receiving portion depth 3705.

According to an embodiment, pan receiving portion 1360 is sized to accommodate various sizes of pans, preferably pans as small as about 0.247 inches in diameter and as large as about 0.295 inches in diameter. Pans of various heights can be accommodated, preferably pans as short as 0.030 inches to as high as 0.181 inches or more. According to an embodiment, pan receiving portion 1360 may be about 0.340 inches in diameter and about 0.094 inches deep. Oblong slots 1370 may have a depth of about 0.156 inches.

One benefit of the preferred embodiment of sample tray 1300 is that different sized pans can be accommodated by autosampler 100. This flexibility results from the well geometry in conjunction with the characteristics of the dual-sensored gripper device 710, particularly, the self-centering feature.

Because fingers 730 open and close along a common circumference, pans of varying sizes can be picked up even if they have moved off the center of a well. This is a significant advantage. Unlike prior art autosamplers that were limited to specific pan types/sizes, the present design permits a variety of pan types/sizes to be used with autosampler 100.

Figure 39:
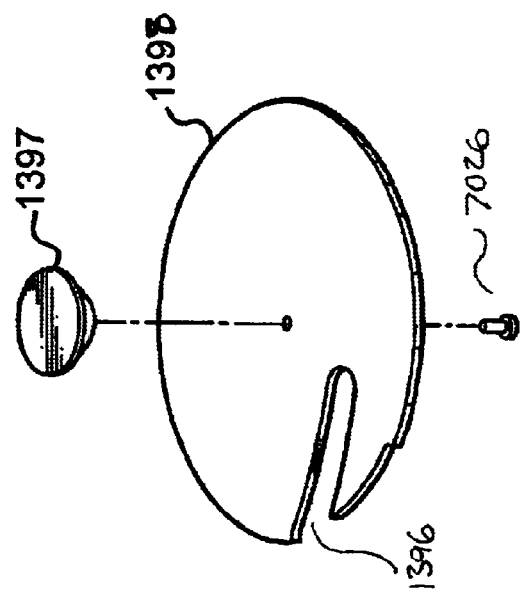
FIG. 39 is an exploded view of a handle and a cover according to a preferred embodiment of the present invention.
Figure 38:
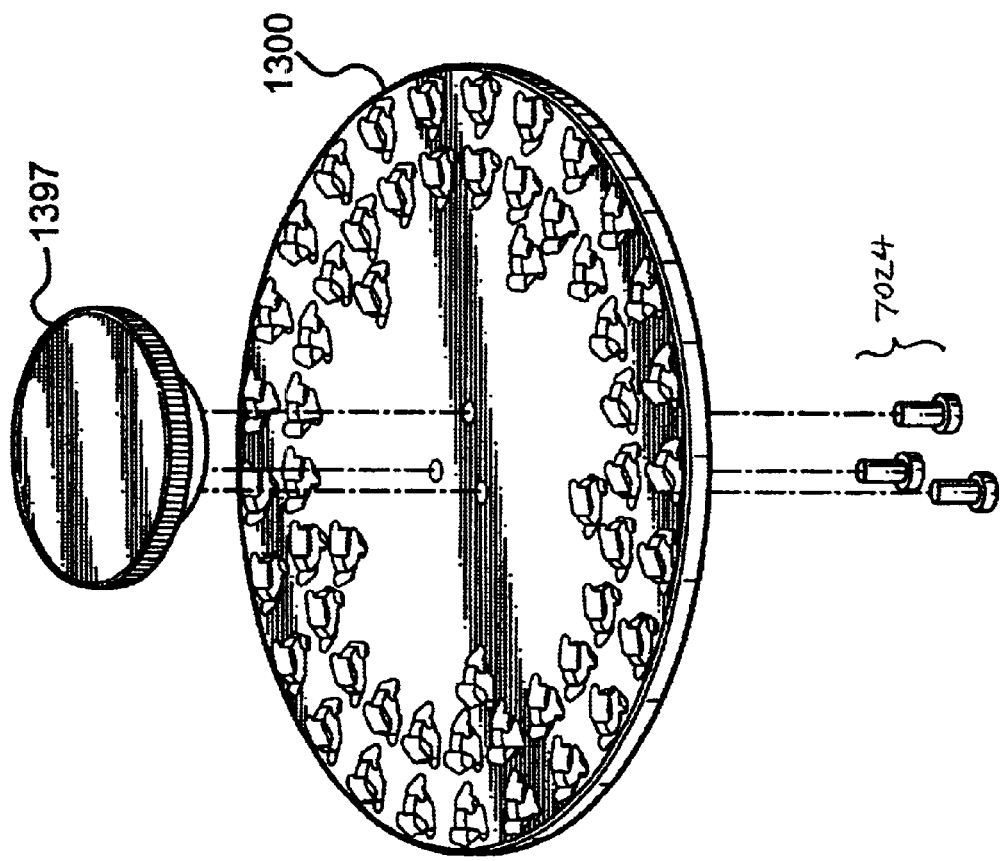
FIG. 38 is an exploded view of a tray and a handle according to a preferred embodiment of the present invention.

FIG. 38 shows a handle 1397 that may be attached to sample tray 1300 for handling. Handle 1397 is attached using a thirteenth set of fasteners 7024. FIG. 39 shows a dust cover 1398 that may be placed over sample tray 1300 while measurements are being taken. Dust cover 1398 may be fastened to handle 1397 using a fourteenth fastener 7026. Preferably, dusk cover 1398 includes a slot 1396 allowing arm 125 to access wells along the common arc.

Figure 41:
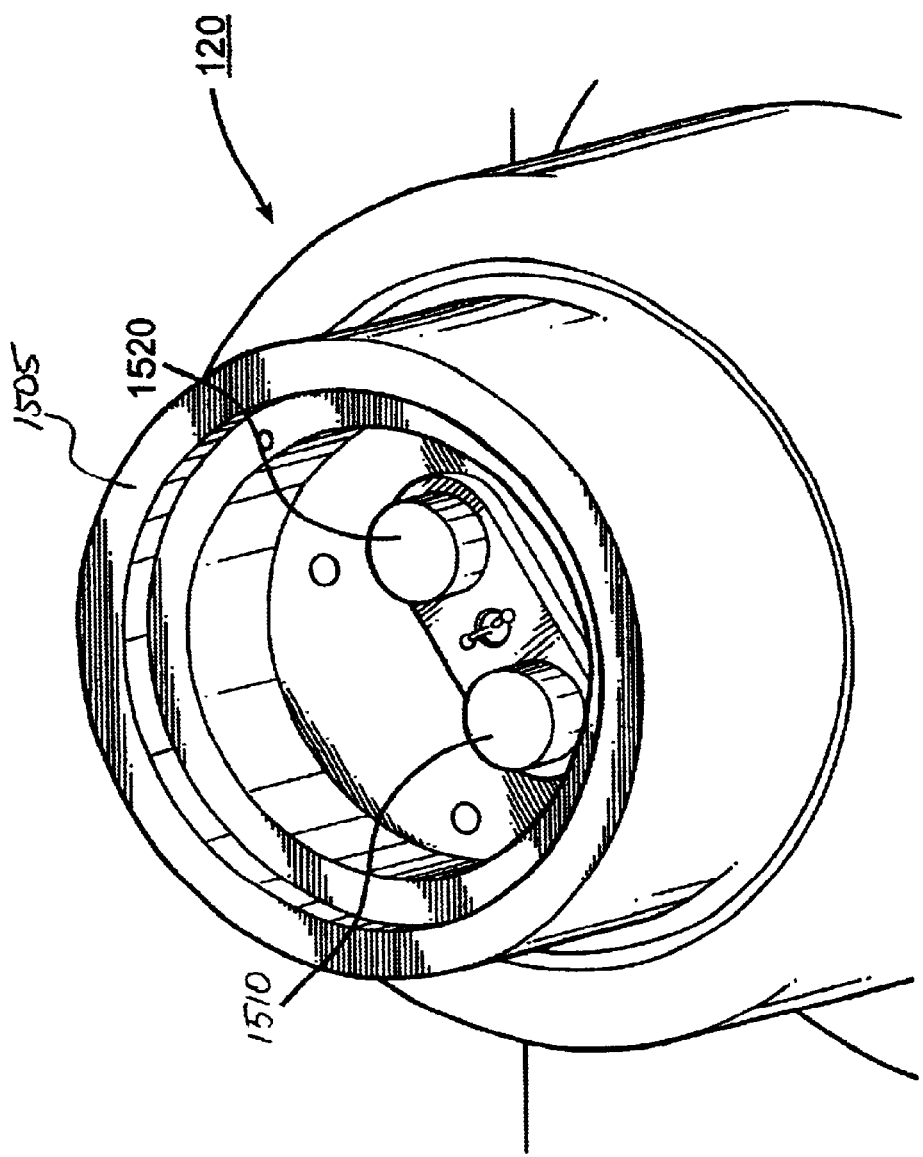
FIG. 41 shows an enlarged view of a DSC cell according to a preferred embodiment of the present invention.

As with the wells 3300 in sample tray 1300, the sample platform and reference platform of cell 120 (see FIG. 2) preferably lie along the common arc. FIG. 41 shows an enlarged view of an exemplary cell 120 including a sample platform 1510 and reference platform 1520. FIG. 42 shows a view of a cell 120 mounted on a measurement platform 4205. Cell 120 includes sample platform 1510 and reference platform 1520. The cells 120 illustrated in FIGS. 41 and 42 are exemplary only. Other cells could be used with autosampler 100, such as cells incorporating multiple sample platforms.

According to a preferred embodiment, the common arc may also intersect the following: disposal area 140 (FIG. 1); a park position for arm 125 during testing; and a shipping position for arm 125 during shipping.

Overall, according to a preferred embodiment, arm 125 may access the following coordinate points along the common arc: cell reference platform; cell sample platform; park position; shipping position; disposal area; first row well; second row well; and reference row well. Coordinates for each of these points may be stored in control electronics module 225.

It is desirable to have a substantially automatic calibration feature for some of these coordinate points. An automatic calibration ("autocalibration") simplifies procedures for the user. It can improve the accuracy of measurements. Mishaps like dropped or misplaced pans can be reduced.

This substantially automatic calibration may be used after the user replaces a cell, replaces a cooling accessory, replaces a sample pan, and so forth. All of these events can affect calibration. Ordinary wear and tear and component drift may also affect calibration.

According to an embodiment, rotating table (also referred to as "platen") 220 may be used for calibrating positions on sample tray 1300.

Figure 44A:
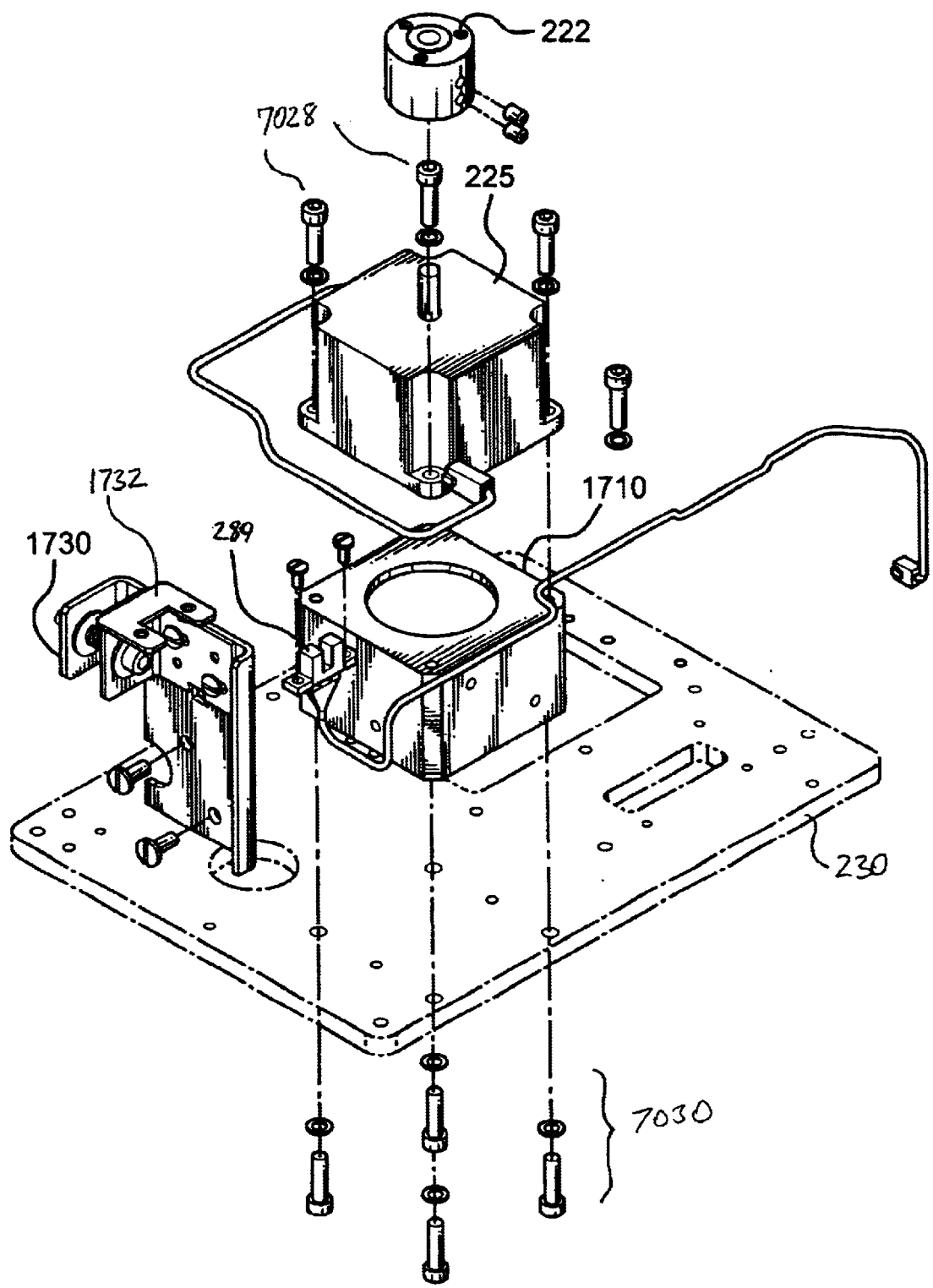
FIG. 44A is an exploded view of a table motor and related parts according to a preferred embodiment of the present invention.

FIG. 44A is an exploded view of a preferred assembly for rotating platen 220. FIG. 44B is an isometric view of a preferred assembly for rotating platen 220. FIG. 44A includes depicts base plate 230, table motor mount 1710, table motor 225, hub 222, rotating table sensor 289, sensor slide mount 1732, and sensor adjuster 1730.

Table motor 225 is mounted to table motor mount 1710 and base plate 230 using a fifteenth set of fasteners 7028. Hub 222 couples to the shaft of table motor 225. As previously described for FIG. 5, hub 222 attaches to rotating table 220. Table motor mount 1710 is attached to base plate 230 with a seventeenth set of fasteners 7030.

The use of rotating table sensor 289 to detect a rotating table 220 home position was discussed in connection with FIG. 5. Rotating table sensor 289 is mounted to sensor slide mount 1732. Sensor adjuster 1730 can be used to move sensor slide mount 1732. Accordingly, sensor adjuster 1730 can be used to adjust the position of rotating table sensor 289 and, therefore, the home position of rotating table 220.

Preferably, rotating table sensor 289 is adjusted during manufacture to locate rotating table sensor 289 sensor exactly along the common arc, e.g., 6.5 inches from the axis of rotation of arm 125.

Figure 31:
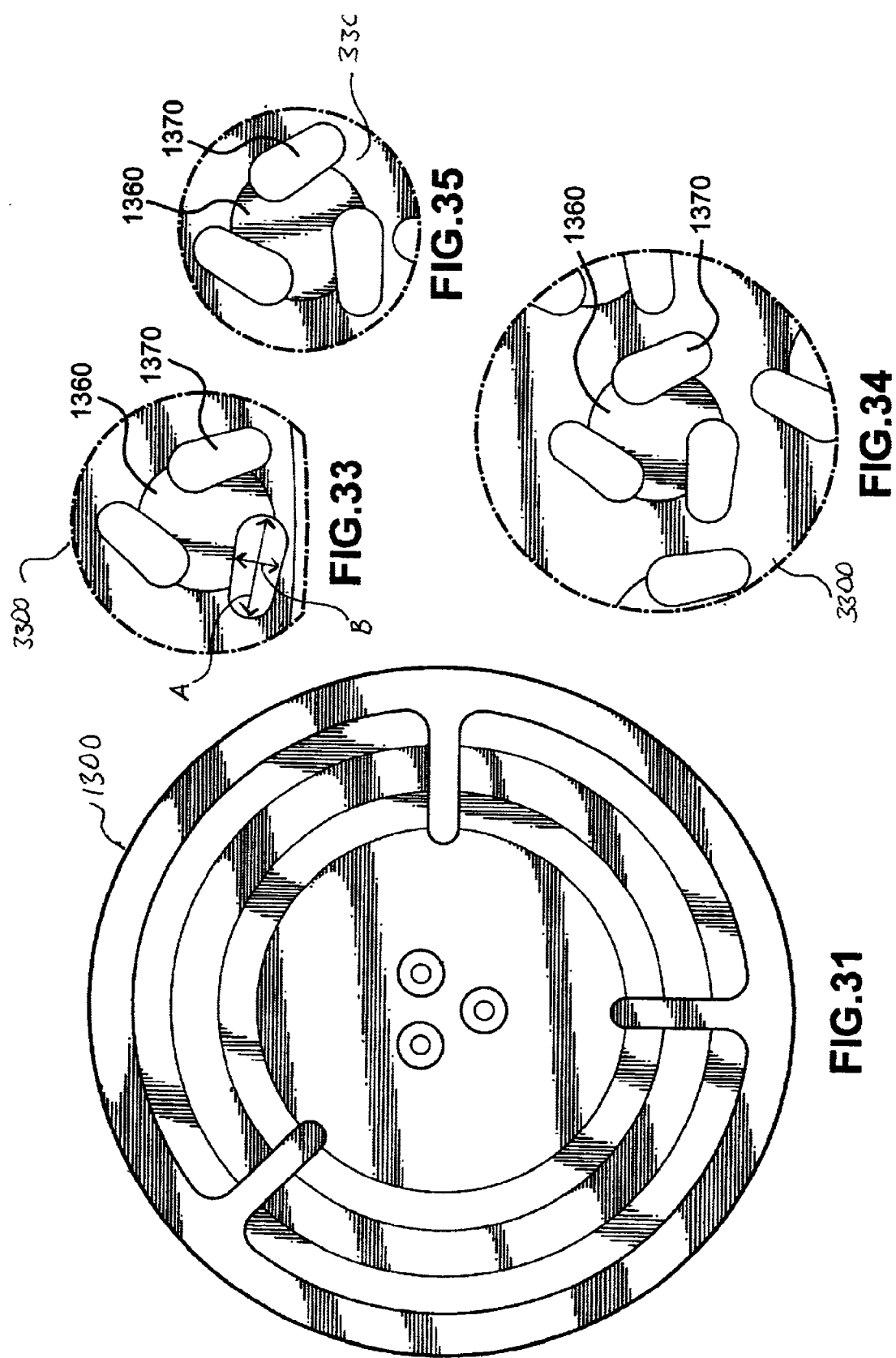
FIG. 31 is a bottom view of a tray according to a preferred embodiment of the present invention.
Figure 32:
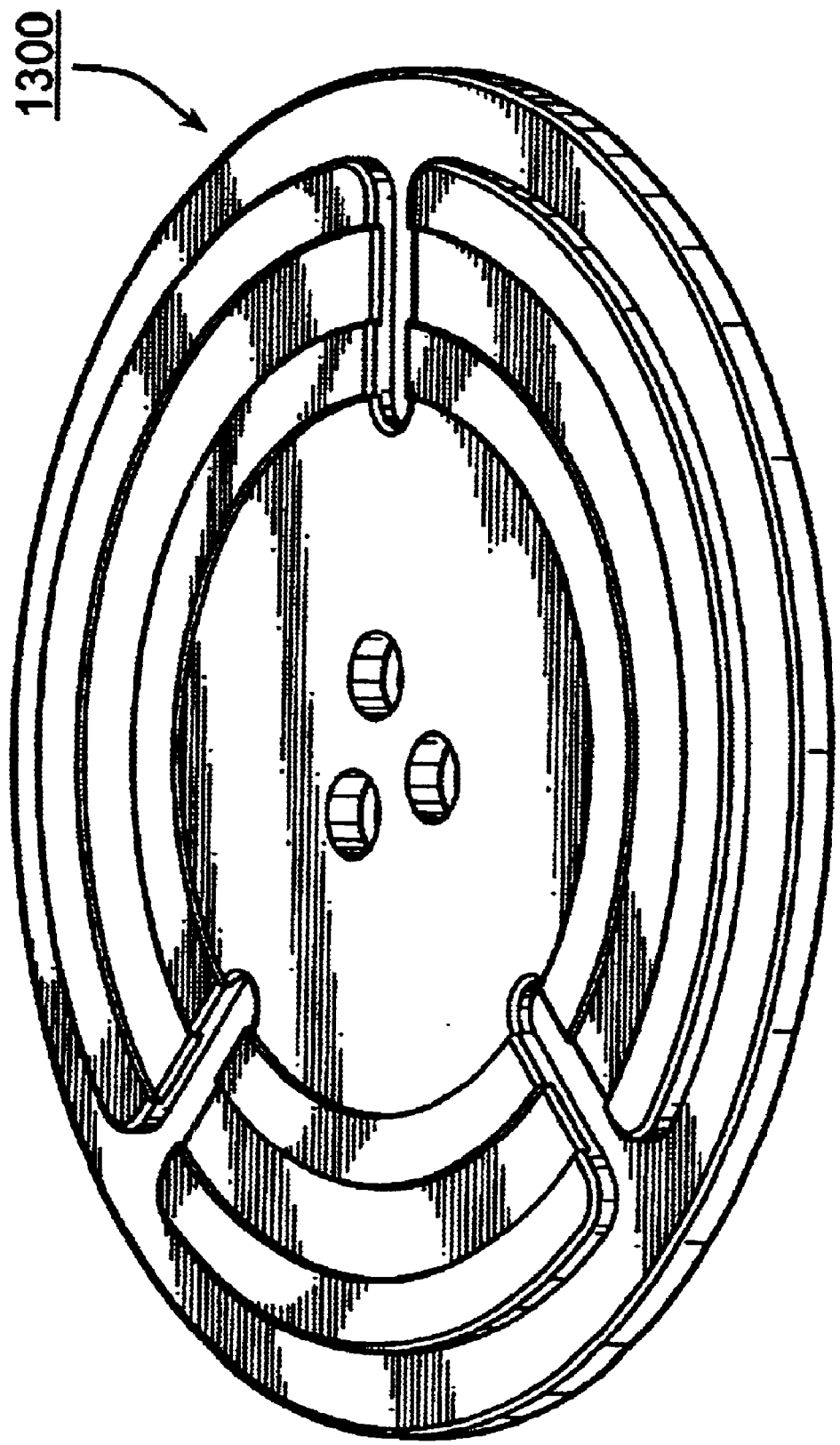
FIG. 32 is a bottom isometric view of a tray according to a preferred embodiment of the present invention.

FIG. 43 is an isometric view of a preferred rotating table 220 according to an embodiment. Rotating table 220 includes surface 1680, lip 1620, location members 1610, and pins 1662. Location members 1610 and lip 1620 may be used to locate a sample tray 1300 onto rotating table 220. As reflected by FIGS. 31 and 32, a preferred sample tray 1300 has structure that is reciprocal to location members 1610 and lip 1620. Preferably, location members 1610 are asymmetric so that sample tray 1300 is not misplaced onto rotating able 220. Pins 1662 are used to provide a statically determinant and stable mount that allows rotating table 220 to support sample tray 1300 with substantially no wobble.

The preferred rotating table 220 in FIG. 43 also includes reflective areas on surface 1680 that can be used for optical detection during calibration. Rotating table 220 includes first aperture 1630, second aperture 1635, and third aperture 1640 for receiving first calibration mirror 1645, second calibration mirror 1650, and third calibration mirror 1655, respectively.

When installed, calibration mirrors 1645, 1650, and 1655 fall along the common arc. According to one embodiment, first calibration mirror 1645 falls under sample well #26 (second row of wells 1320, FIG. 30); the second calibration mirror 1650 falls under reference well #1 (third row of wells 1330, FIG. 30); and the third calibration mirror 1655 falls inside the third row of wells. Third calibration mirror 1655 corresponds to a fictitious well. Third calibration mirror 1655 is used in place of a calibration mirror under sample well #1 (first row of wells 1310, FIG. 13A) that would fall too close to the edge of rotating table 220.

According to a preferred embodiment, apertures 1630, 1635 and 1640 have a diameter of about 0.200 inches, preferably about 0.202 inches. In an embodiment, mirrors 1645, 1650, and 1655 are so-called "front surface" mirrors.

Preferably, platen 220 is made of a conductive material that is finished (excepting the mirrors) with a nonreflective coating, such as a black anodized coating.

The preferred rotating table 220 in FIG. 43 also includes a conductive area on surface 1680 that may be used for electrical detection. For example, conductive area 1660 may be used for electrical sensing by the gripper fingers 730 during a calibration process. According to an embodiment, conductive area 1660 has a diameter of about 0.75 inches. Preferably, conductive area 1660 falls along the common arc of rotation. Conductive area 1660 may be created by removing an area of black anodized coating after rotating table 220 is finished with a nonreflective coating. These features permit a preferred embodiment of rotating table 220 to be used to calibrate positions on sample tray 1300 using electrical and optical sensing.

The invention includes provisions that permit the automatic sampler to automatically calibrate itself. The term "automatic" as refers to automatic calibration, means that the calibration process requires less technician or human participation than a fully manual calibration process. While the automatic calibration process may be fully automatic, meaning that the calibration process requires no human or technician participation, automatic calibration also refers to those calibration processes that require less human or technician participation up to and including a calibration process that requires no human or technician participation.

Figure 49:
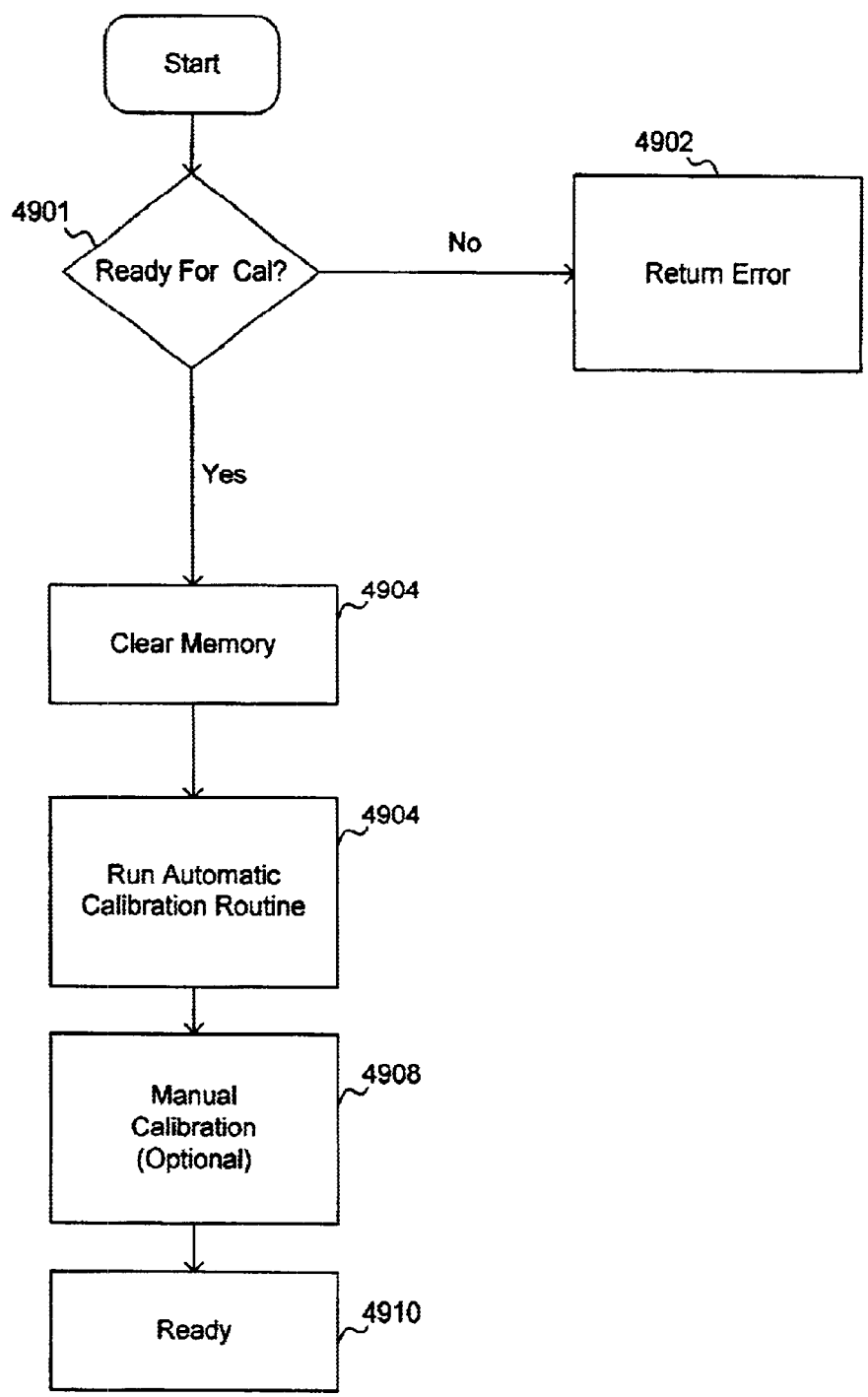
FIG. 49 is an overview of a preferred embodiment of a preferred calibration routine.
Figure 50:
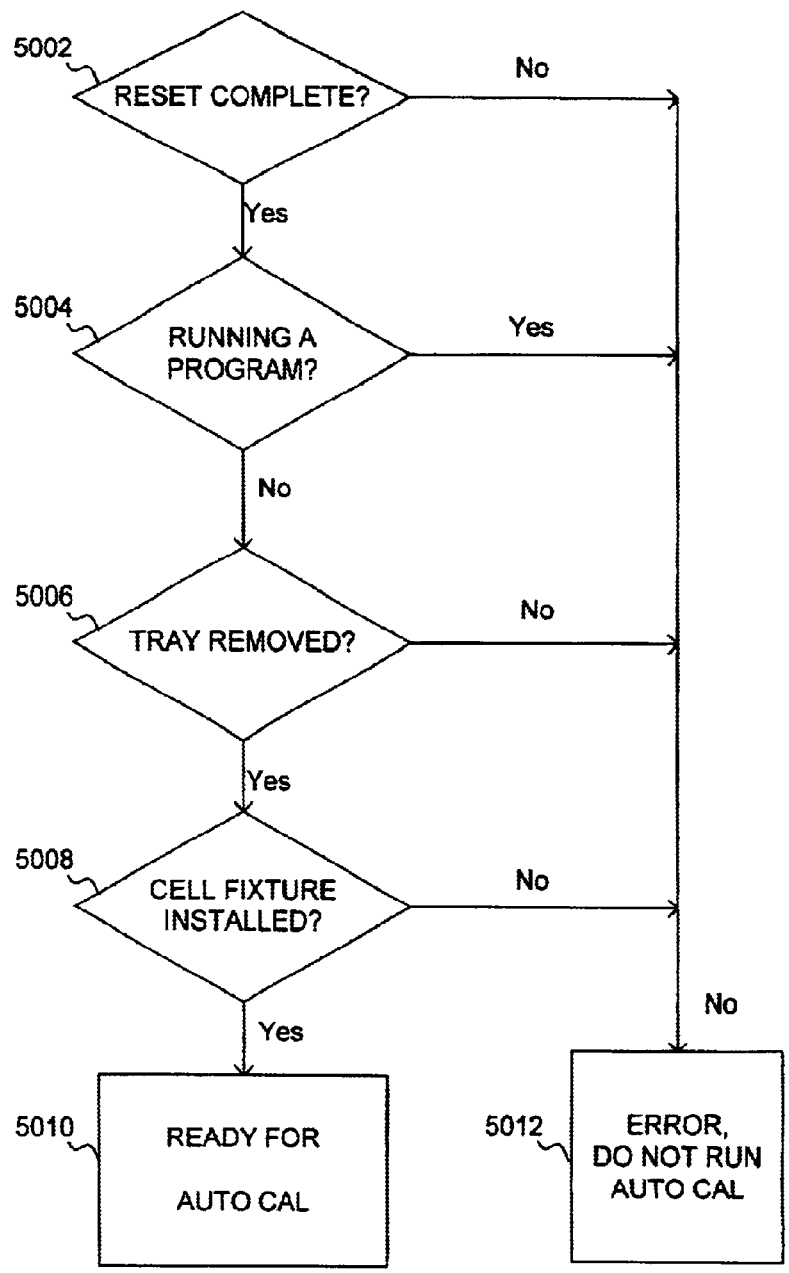
FIG. 50 is a preferred embodiment of a flow diagram for step 4901.
Figure 51:
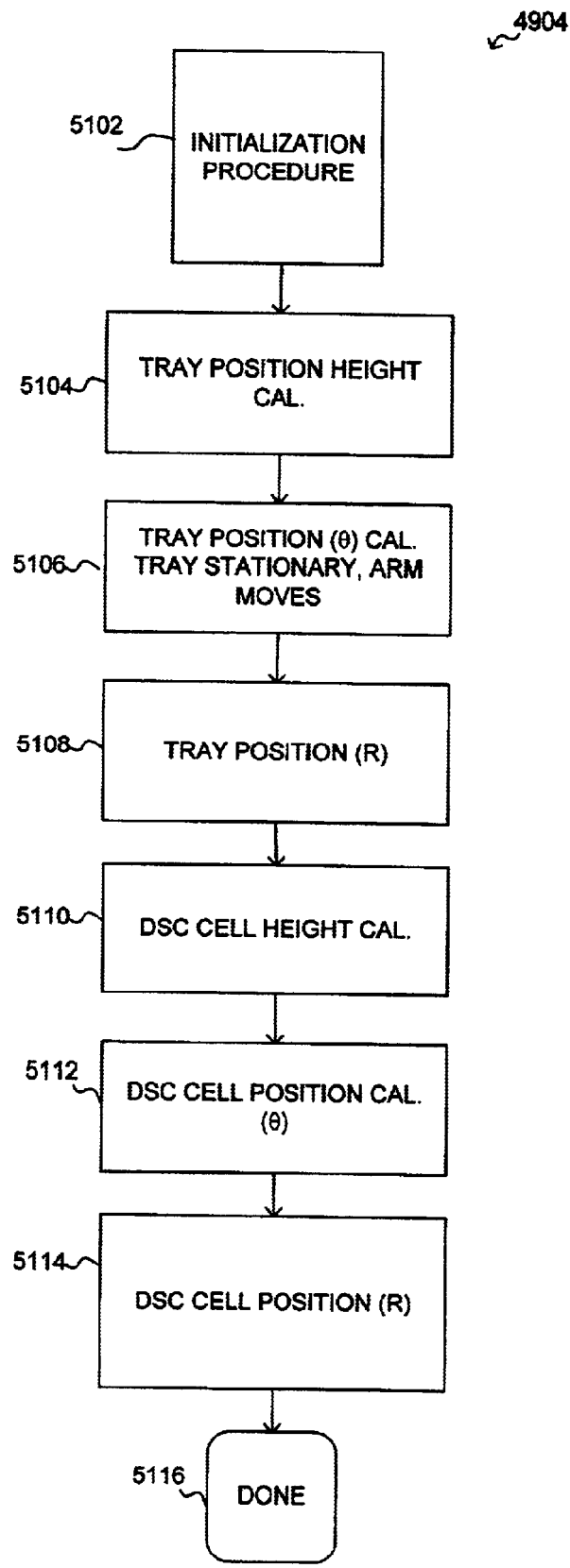
FIG. 51 is a preferred embodiment of a flow diagram for step 4904.
Figure 52A:
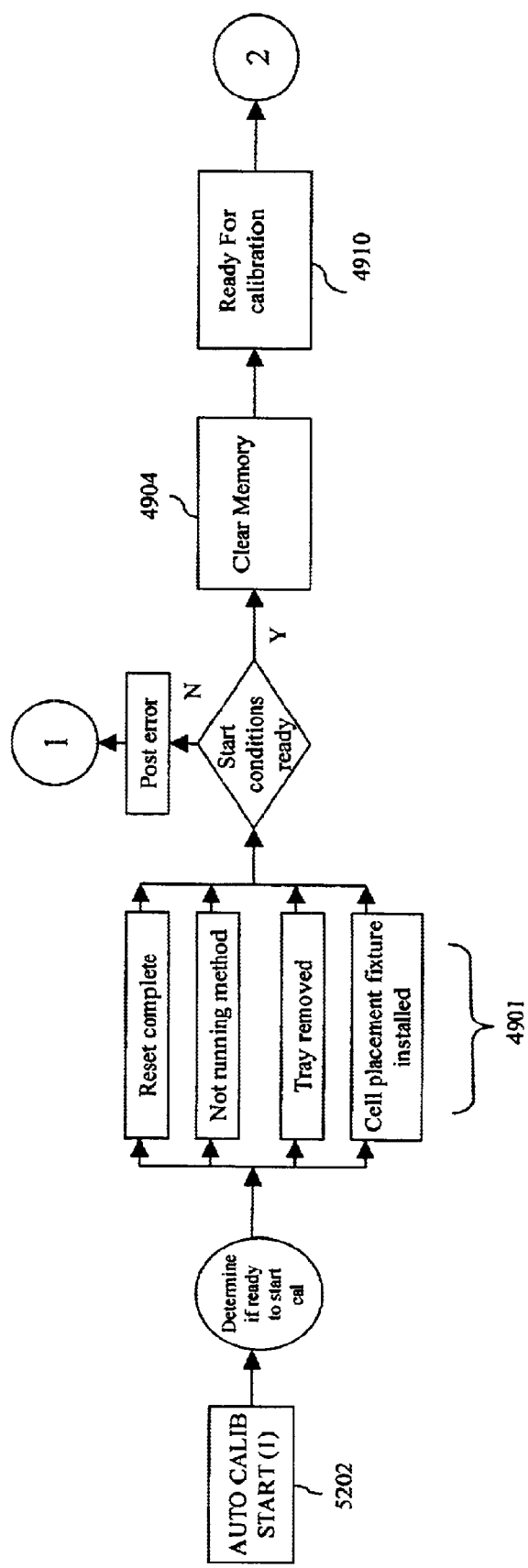
FIGS. 52A-52AF provide a flow diagram for performing a calibration procedure according to a preferred embodiment of the invention.

FIGS. 49-52AF show flow diagrams disclosing a preferred embodiment of the present invention. FIG. 49 is an overview of a preferred calibration routine. FIGS. 50 and 51 provide additional details of some of the steps shown in FIG. 49. FIGS. 52A-52AF disclose a detailed description of the preferred calibration routine.

FIG. 49 shows a flow diagram of a preferred embodiment of the calibration routine of the present invention. The calibration routine shown in FIG. 49 preferably includes several steps. Preferably, in the first step 4901 of the calibration routine, a determination is made as to whether the system is ready for a calibration routine. If the system is not ready, then an error is returned in step 4902. If the system is ready for a calibration routine, then the system proceeds to step 4904 where the system clears memory. The system clears from memory information related to the cell placement pan numbers.

After the appropriate memory locations have been cleared in step 4904, the system is then ready to run the automatic calibration routine in step 4906. After the automatic calibration routine has been completed, the technician can conduct a manual calibration routine in step 4908. This manual calibration routine is optional and need not be conducted. After all of the desired calibration steps have been performed, the system is ready to receive instructions. This is shown in step 4910.

FIG. 50 is a more detailed view of step 4901 (see FIG. 52A), the where a determination is made as to whether the system is ready to proceed with a calibration routine. Preferably, there are several steps within the "ready for calibration" step 4901. Turning to FIG. 50, the system first checks to see if the reset routine is complete in step 5002. The reset routine is a series of steps performed by the system when the system is initially turned on or if a user instructs the system to conduct a reset routine. Preferably, the system waits until the reset routine has ended before commencing a calibration routine.

Next, the system sees if a program is currently running in step 5004. A program refers to an experiment or other procedure where a system resource is currently being used in some way. One example of a program would be a condition where a technician instructed the DSC cell 120 to conduct a heating or cooling routine and the system was collecting data from the experiment. Preferably, under these conditions, the system would not permit the user to commence a calibration routine.

In order for the calibration procedure to proceed properly, tray 1300 (see FIG. 30) must be removed from moving table 220 (See FIG. 5). The system preferably includes a sensor 810 (See FIG. 14) that senses the existence or absence of tray 1300 (See FIG. 30). If the tray has not been removed, the system could prompt the user to remove tray 1300 or the system could return an error 5012 and refuse to run the calibration procedure. The system determines if tray 1300 has been removed in step 5006.

Figure 45:
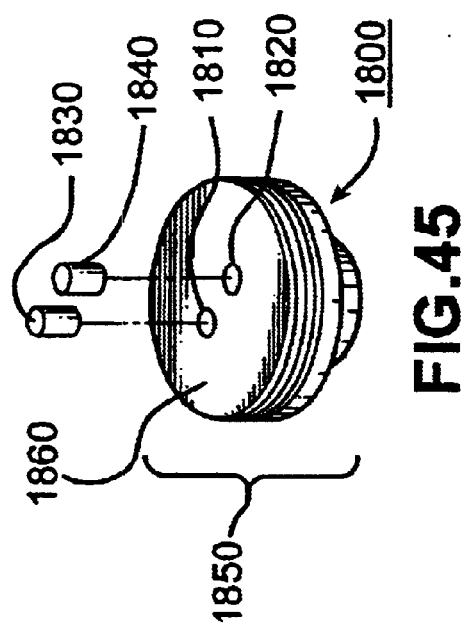
FIG. 45 is an exploded view of a cell calibration member according to a preferred embodiment of the present invention.

Another step that is necessary to run the calibration routine is the proper placement of cell fixture 1800 (see FIG. 45). Although the placement of cell fixture 1800 could be sensed, the preferred embodiment prompts the user to install cell fixture 1800 in step 5008.

If any one of the above steps is not verified, the system returns an error message in step 5012 and refuses to run the calibration routine. If all of the steps have been met, the system determines that it is ready to commence the calibration routine in step 5010.

FIG. 51 shows the preferred steps that are used to accomplish the "run automatic calibration routine" step 4906, shown in FIG. 49. As shown in FIG. 51, the automatic calibration routine preferably includes an initialization procedure, step 5102, a tray height calibration step 5104, a tray position calibration step 5106, a cell height calibration step 5108, and a cell position calibration step 5110. After the cell calibration step 5110 has been accomplished, the automatic calibration routine is finished in step 5112.

Figure 52B:
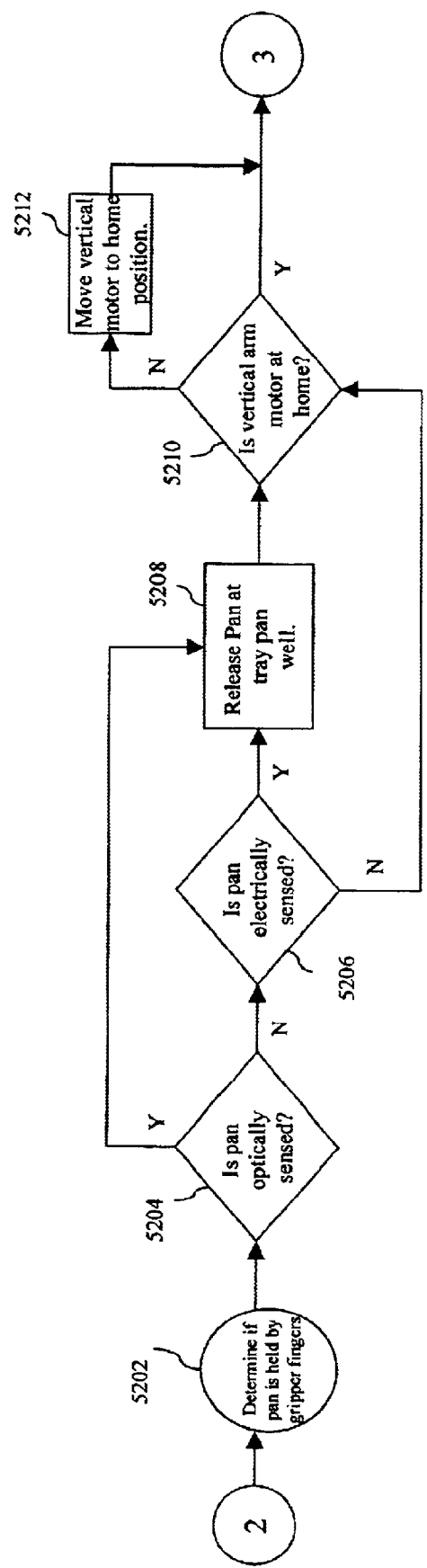
Figure 52C:
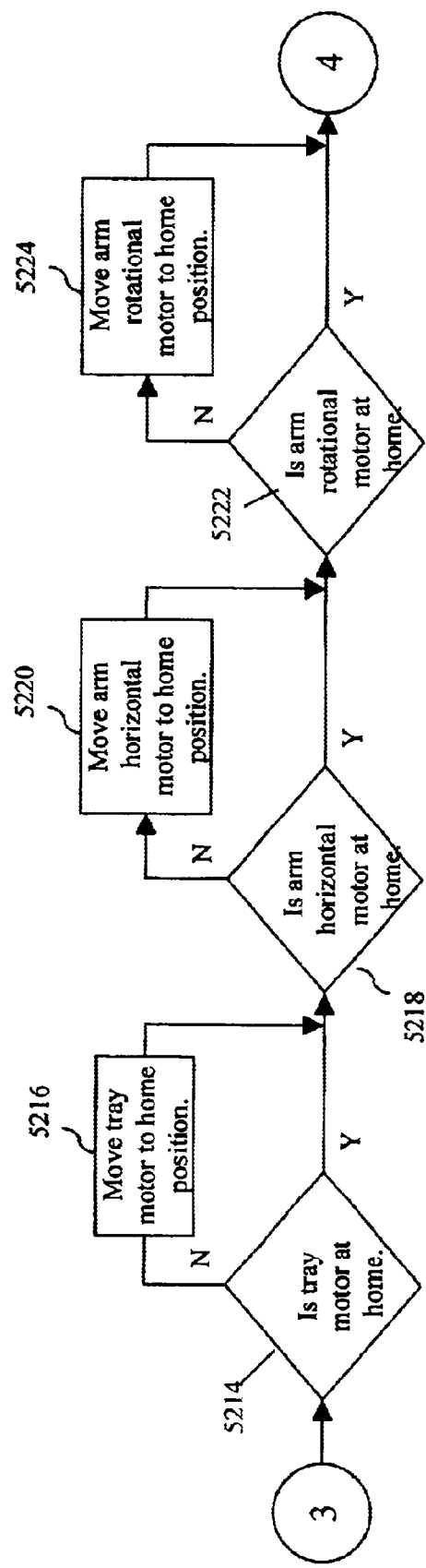
Figure 52D:
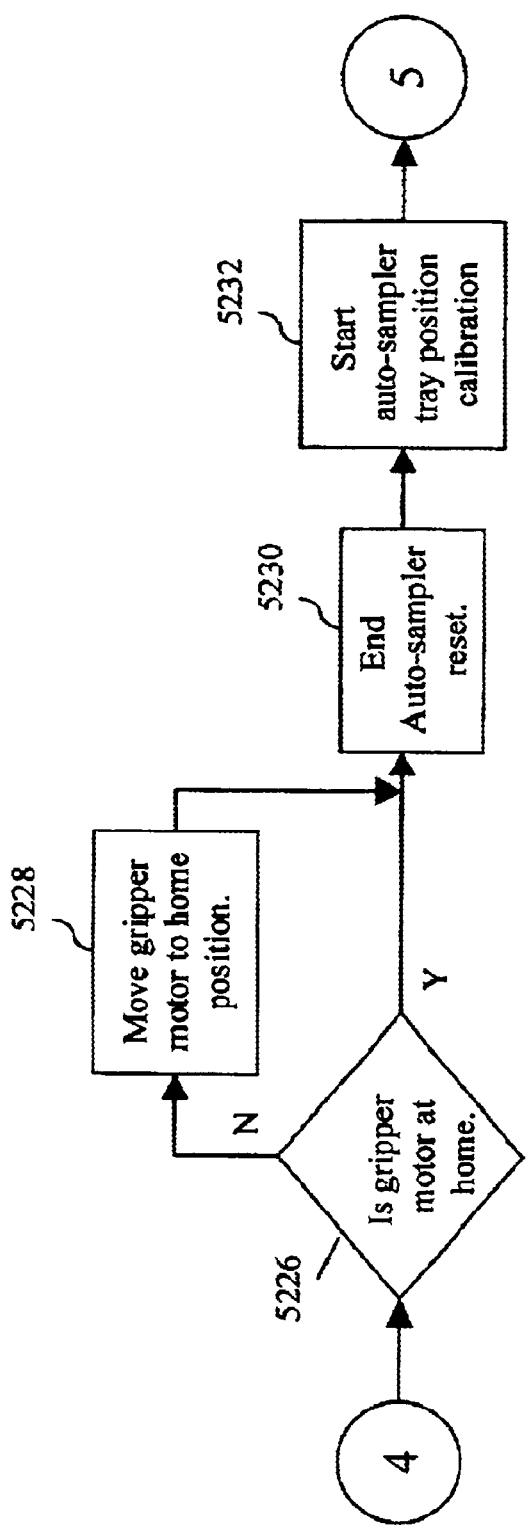

The preferred steps used to accomplish initialization procedure step 5202, are shown in FIGS. 52B-52D. The first procedure to ensure that the gripping device 710 has dropped anything it may be currently holding. This procedure begins by determining if the gripping device 710 is holding a pan in step 5202. The system determines if gripping device 710 is holding something by using optical sensor 810 in step 5204. The system then uses electrical sensor 730 in step 5208 to determine if gripping device 710 is holding a pan. If the system determines that gripper device 710 is holding a pan, the system instructs gripping device 710 to drop the pan in disposal area 140 (see FIG. 1).

In steps 5210–5228, the system returns all of the various components back to their home positions. As discussed above, each of the items found in steps 5210–5228 include provisions to assist the items in returning to their home positions and to determine when those items are in their home positions. In step 5230, the initialization procedure 5102 (see FIG. 51) has been completed. The system is now ready to commence various calibration routines.

Returning to FIG. 51, after the initialization procedure in step 5202 has been completed, the system then calibrates the relative heights of the gripper device 710 and the moving table 220 in step 5104. A preferred embodiment of this procedure is shown in FIG. 53 and in FIG. 52E, flow diagram steps 5234–5240. The system preferably calibrates the relative heights by moving the gripper device 710 towards moving table 220. Preferably, moving table 220 includes a conductive area or contact surface 1660, which is also preferably electrically conductive. Preferably, moving table 220 is placed in its home position for this height calibration procedure. Preferably, when moving table 220 is in its home position, gripper device 710 is able to move and contact the contact surface 1660.

Figure 52E:
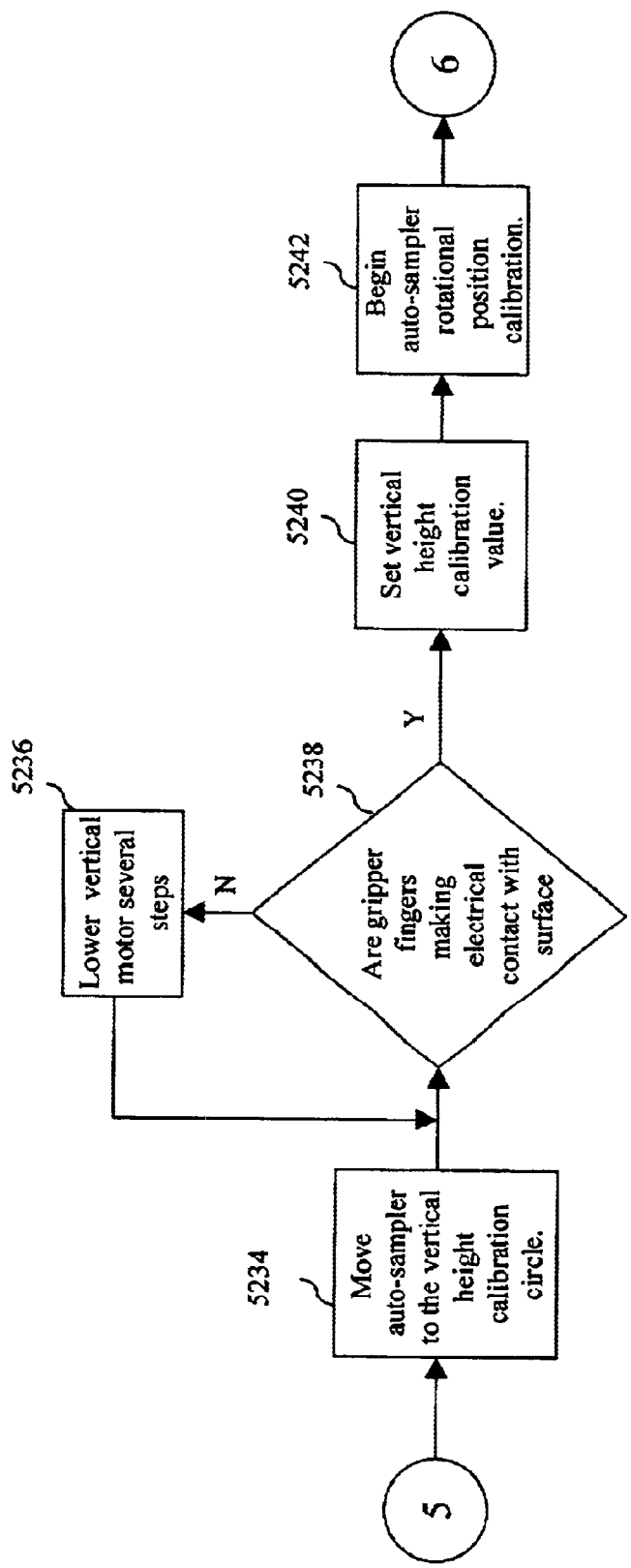

Referring to FIG. 52D, 52E and 53, in the first step 5234 gripper device 710 of sample arm 125 is moved until gripper device 710 is located over conductive area 1660, also known as the height calibration circle. Next, in steps 5238 and 5236 conductive fingers 730 are lowered by lowering sample arm 125 until conductive fingers 730 contact conductive area 1660. When conductive fingers 730 contact conductive area 1660, the system detects a contact and records the vertical position of sample arm 125 relative to conductive area 1660. This can occur in step 5242. Because the physical dimensions of the sample tray 1300 (see FIG. 30) are known, the vertical distance between sample tray 1300 relative to sample arm 125 can be easily computed. In addition, since the vertical distance between sample tray 1300 and sample arm 125 is known, the system can also determine how deep into sample tray 1300 the gripper device 710 should travel in order to retrieve sample pans. This value can also be stored in step 5240. Once a value between sample arm 125 and sample tray 1300 has been determined, and the vertical calibration procedure 5104 is complete.

In a preferred embodiment, control electronics module 235 makes the computations associated with the determination of relative vertical heights.

The height calibration may be performed during each automatic calibration, or at the request of a technician. Preferably, the height computation is performed prior to the horizontal position computation, discussed below.

The present invention can also include provisions for determining the relative horizontal positions of the gripper device 710, the tray, and the wells of tray 1300. Any suitable sensing system may be used, but preferably, an optical sensing system is used. While this procedure of determining the relative horizontal positions of the gripper device 710 and tray 1300 can be conducted in any desired order, the following procedure is preferred.

Figure 55:
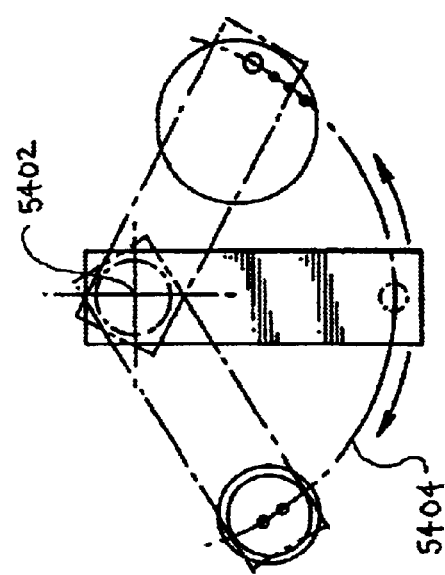
FIG. 55A is a schematic top view of a common arc according to a preferred embodiment of the present invention.
FIG. 55B is an enlarged top view view of a common arc according to a preferred embodiment of the present invention.
Figure 54:
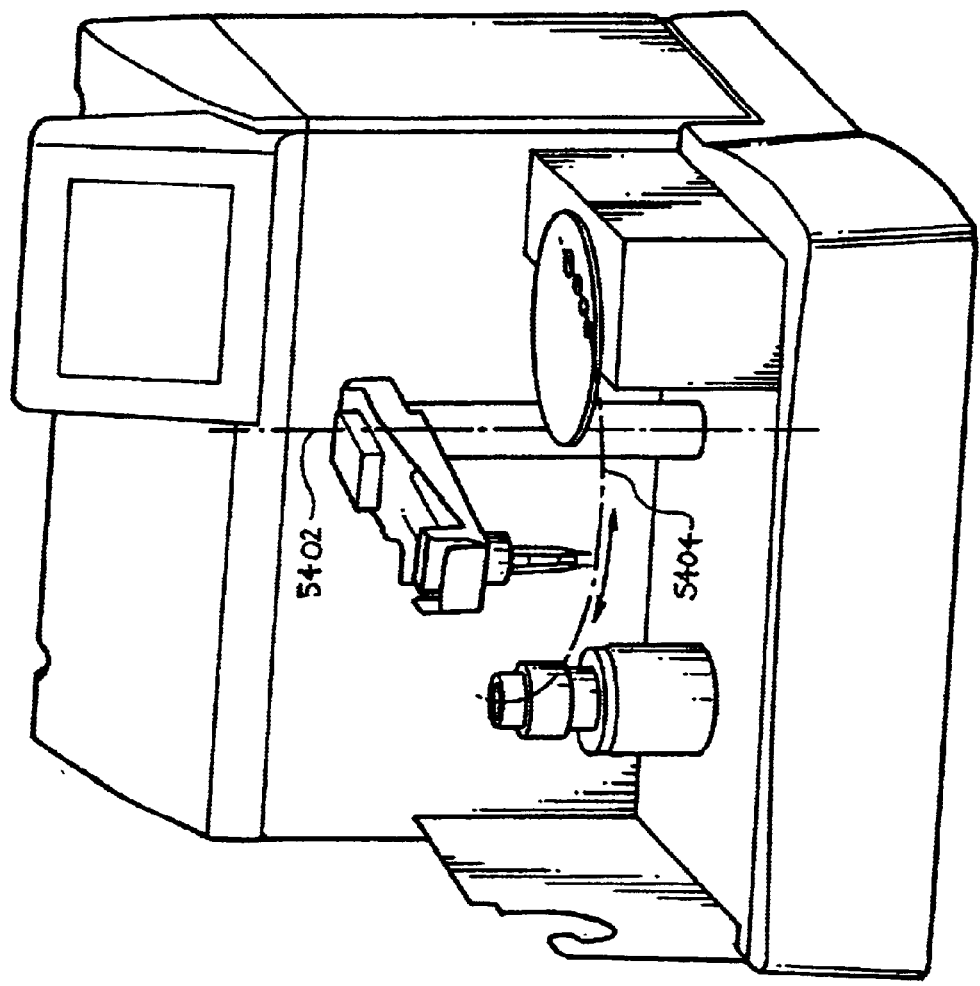
FIG. 54 is an interior view of a DSC system according to a preferred embodiment of the present invention.
Figure 55B:
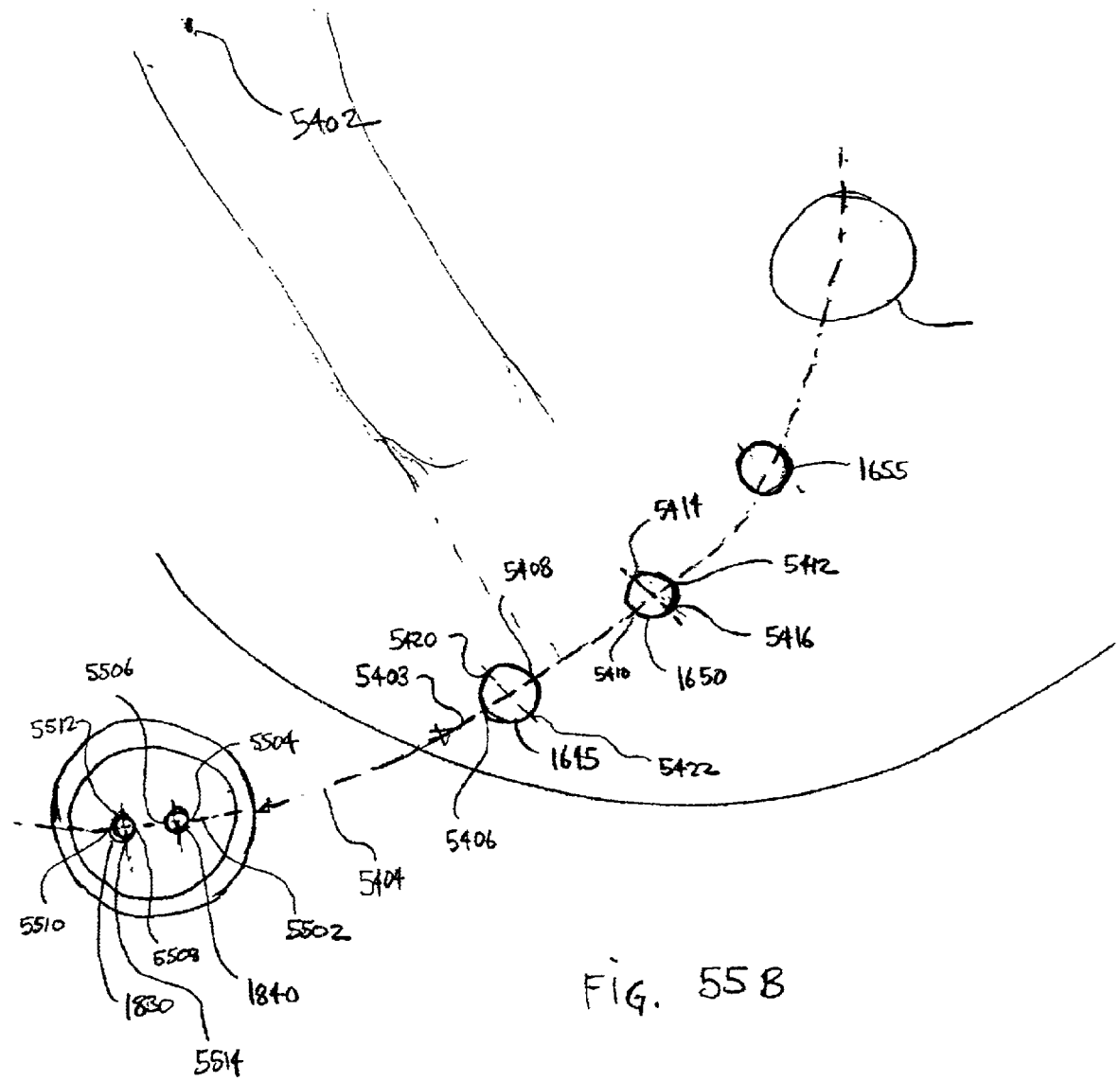

Turning to FIGS. 54, 55A and 55B, recall that moving table 220 includes at least one reflective area 1645. Preferably, moving table includes three reflecting areas 1645, 1650 and 1655. At least one of these reflecting surfaces are used in conjunction with a sensor to determine the relative positions of gripper device 710 and moving table 220.

Sample arm 125 has an arm axis of rotation 5402 and sample arm 125 is able to pivot about this arm axis of rotation 5402. Because gripper device 710 is attached to sample arm 125, gripper device 710 also pivots about arm axis of rotation 5402. As gripper device 710 is pivoted about arm axis of rotation 5402, gripper device 710 moves along a circumferential path 5404.

Preferably, moving table 220 remains in its home position for this angular calibration procedure. In the home position, contact surface 1660 is preferably disposed along circumferential path 5404 as well as reflective surfaces 1645, 1650, and 1655. Preferably, at least one of these three reflective surfaces corresponds in some way with at least one well 1340 disposed on tray 1300. In the preferred embodiment, two of the reflective surfaces are disposed underneath two respective wells. In an exemplary embodiment, reflective surface 1645 is disposed underneath well 26 and reflective surface 1650 is underneath well R1. In the exemplary embodiment, reflective surface 1655 is not disposed underneath a specific well but is disposed along circumferential arc 5404.

Figure 52F:
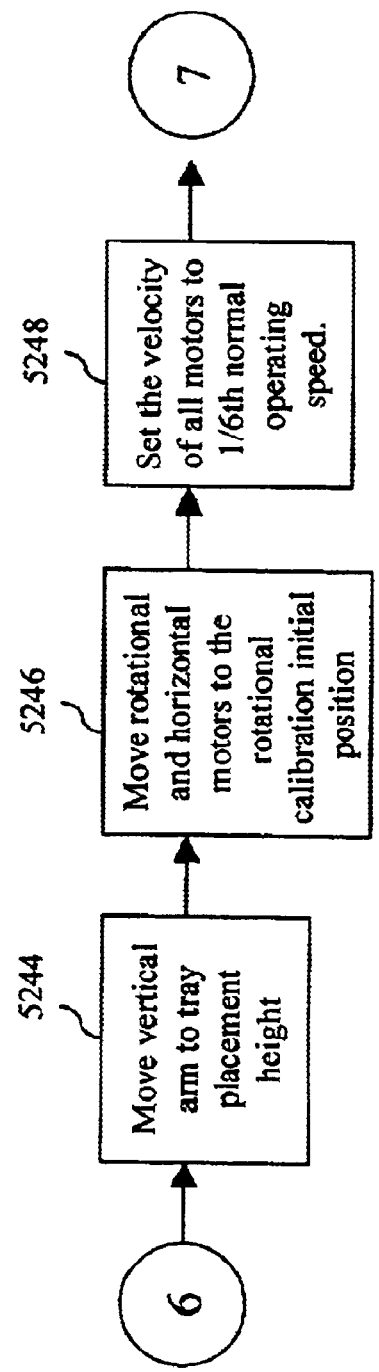

FIGS. 52E and 52F show the preferred steps that are taken before the system attempts to calibrate the relative angular positions of the gripping device 710 and the reflective surfaces. First, in step 5244, the sampling arm 125 is moved to the tray placement height. Next, in step 5246, the rotational and horizontal motors move sample arm 125 to the preferred calibration initial position. Then, the velocity of all of the motors is reduced in step 5248. Preferably, the motors are set to run at ⅟₁₆th their normal speeds.

After moving table 220 has been moved to its home position, the system commences a procedure to determine the angular locations of the reflective surfaces 1645, 1650, and 1655. Once the angular positions of the reflective surfaces are known, the angular positions of the wells on tray 1300 can be determined.

Preferably, the angular position of the moving table 220 with respect to gripper device 710 is accomplished with the use of optical sensing techniques. The motion of the various parts can be understood in the context of a cylindrical coordinate system with sampling arm axis 5402 serving as the axis of the cylindrical coordinate system. Preferably, the relative angular ($\theta$) position of each of the three mirrors 1645, 1650, and 1655 is determined. Then the distance R, or radial distance from sampling arm axis 5402 is determined for at least two of the mirrors. R and $\theta$, of course, define a point in a two dimensional cylindrical coordinate system.

Figure 52G:
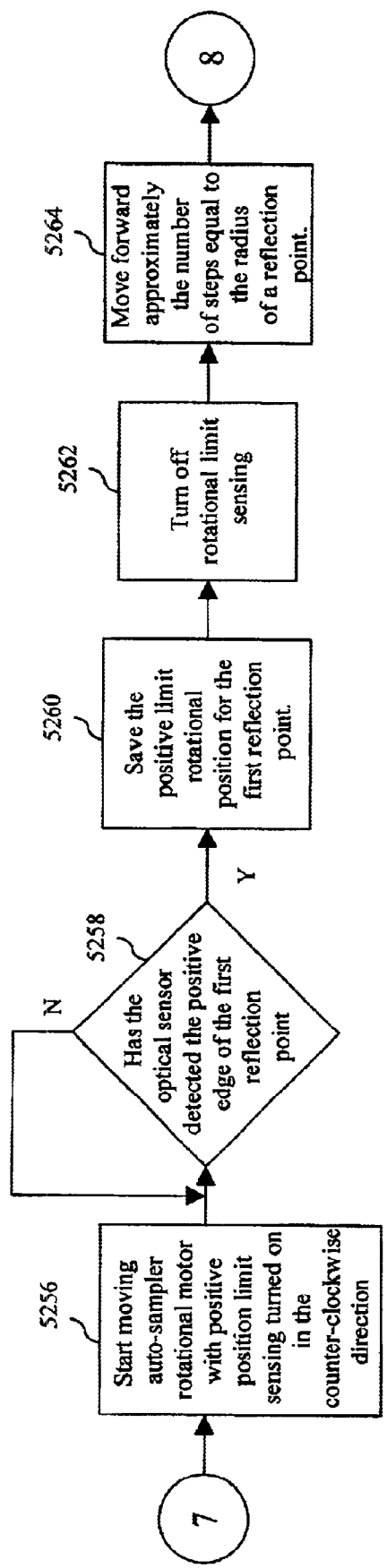
Figure 52H:
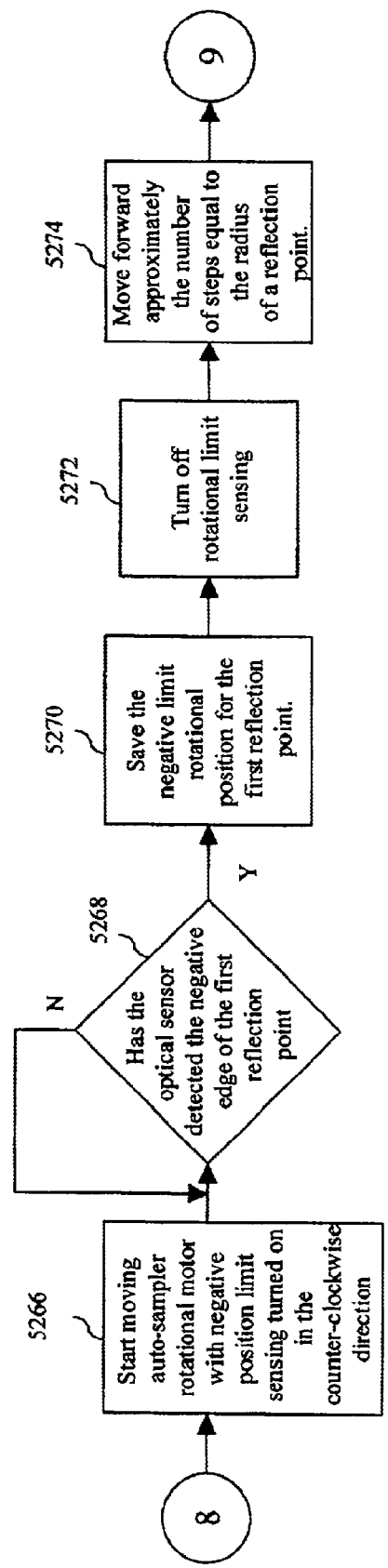
Figure 52I:
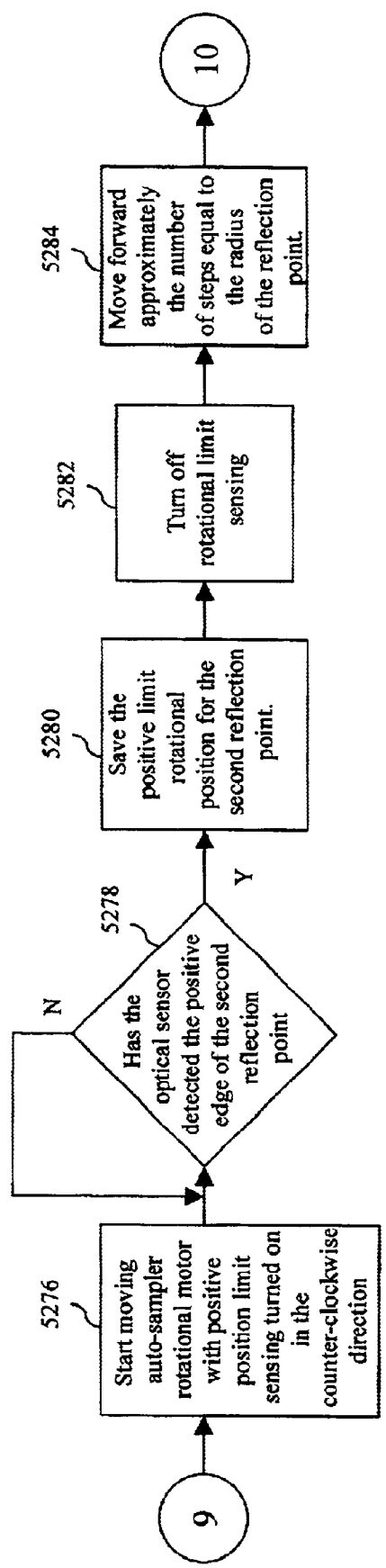
Figure 52J:
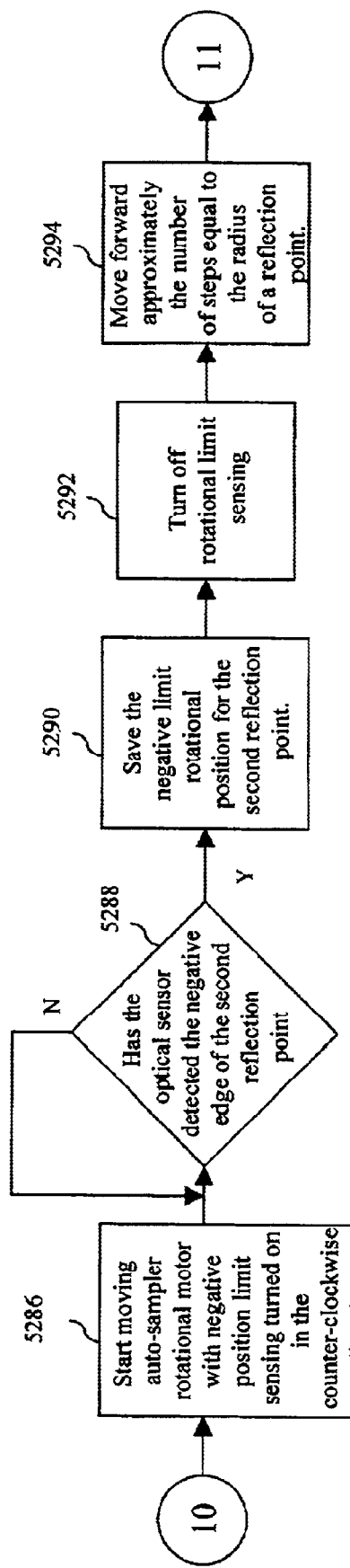
Figure 52K:
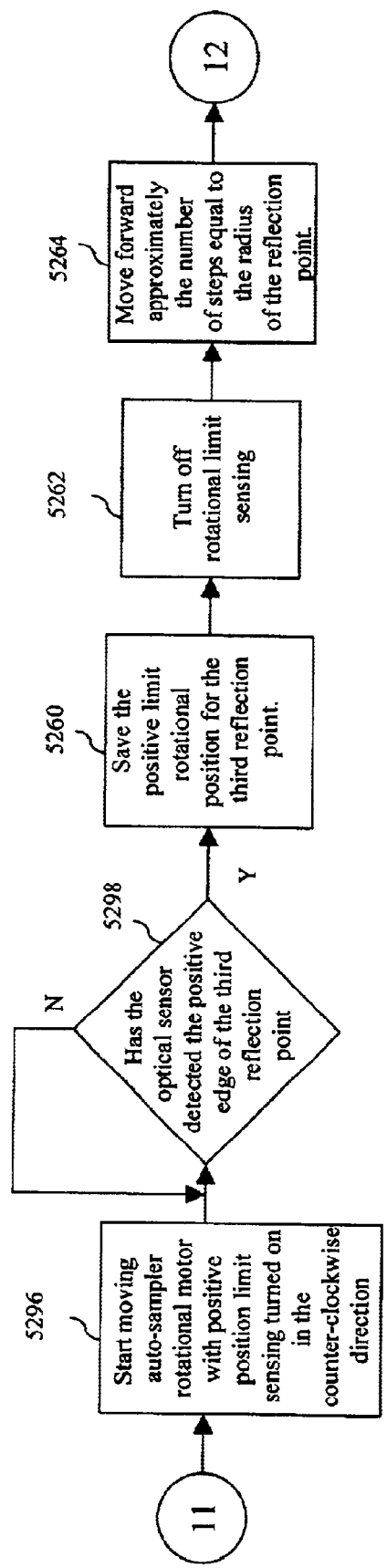
Figure 52L:
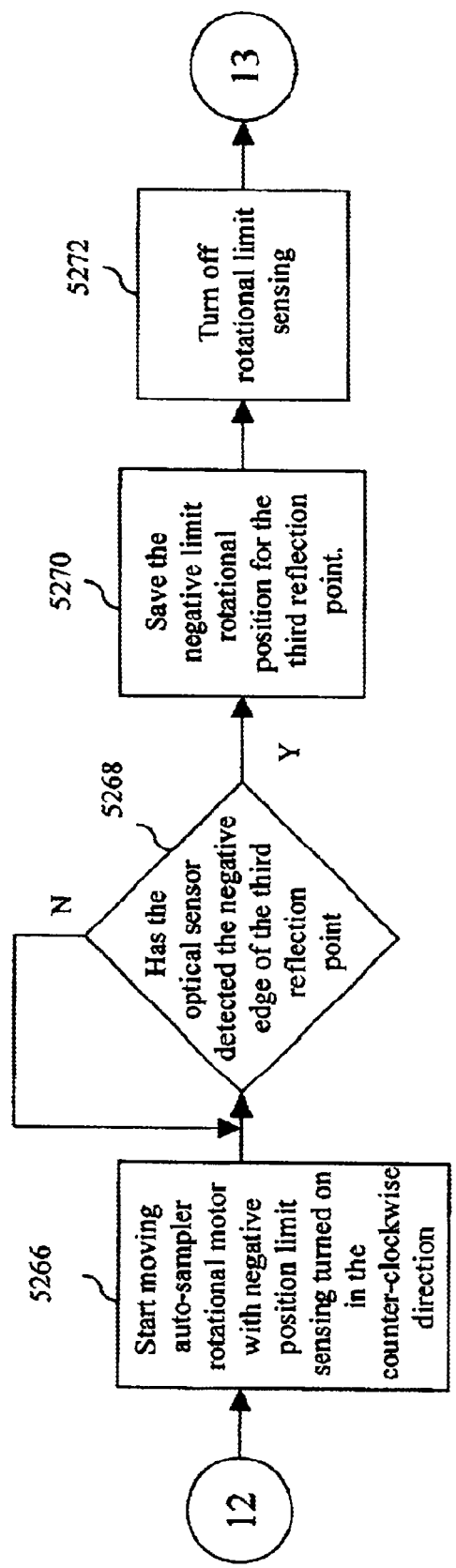
Figure 52M:
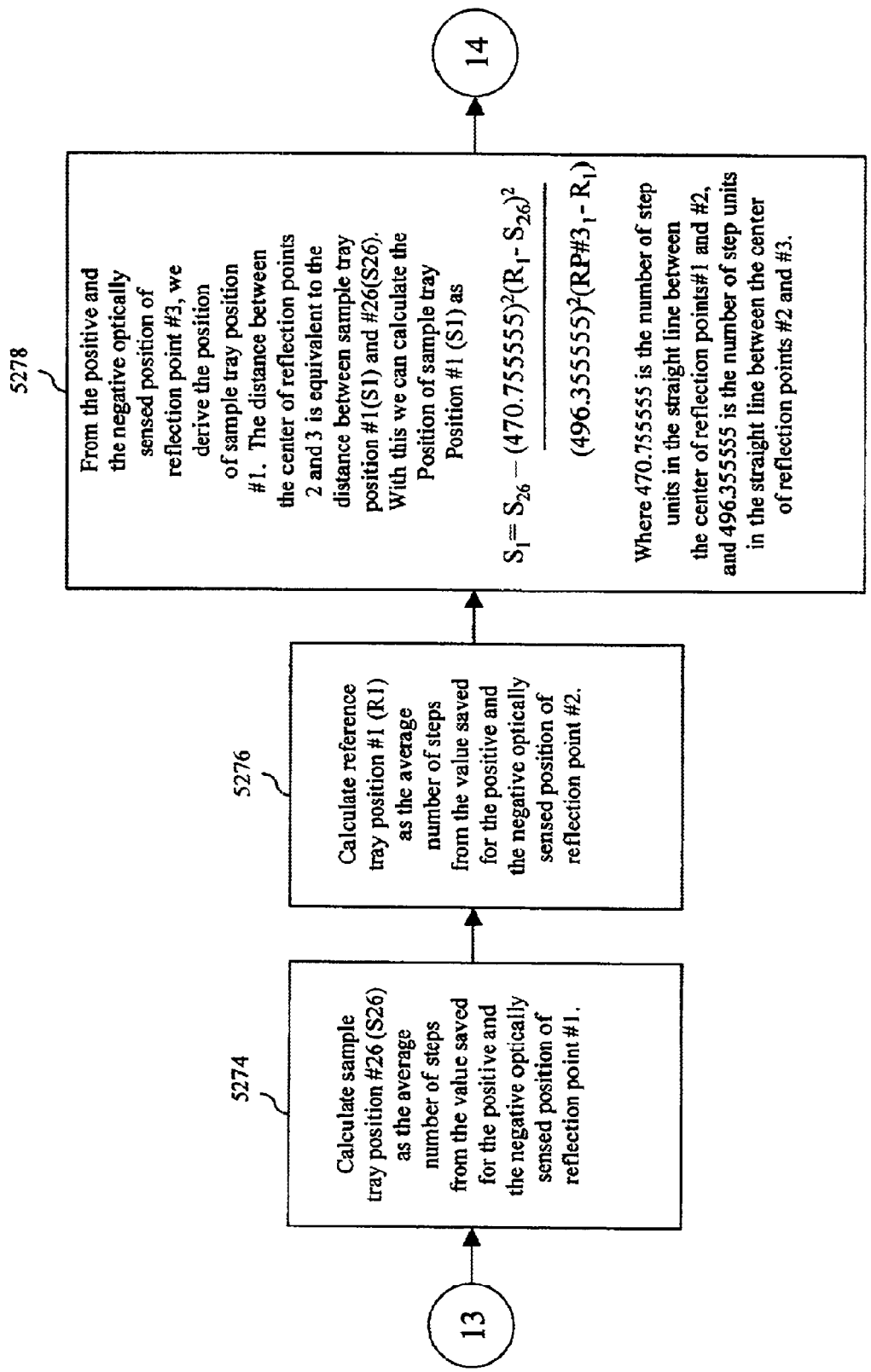
Figure 52N:
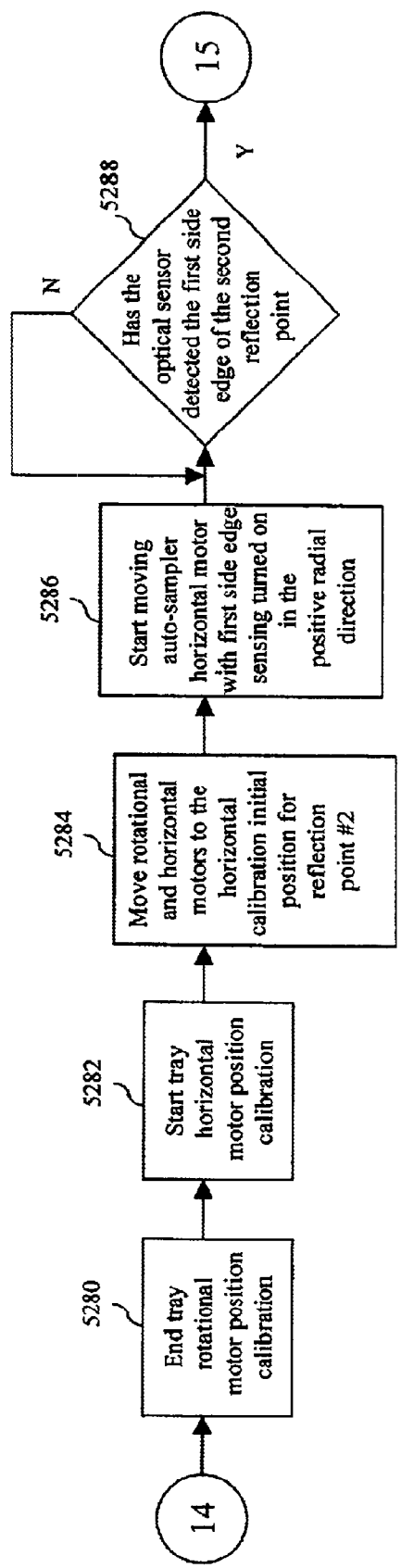
Figure 52O:
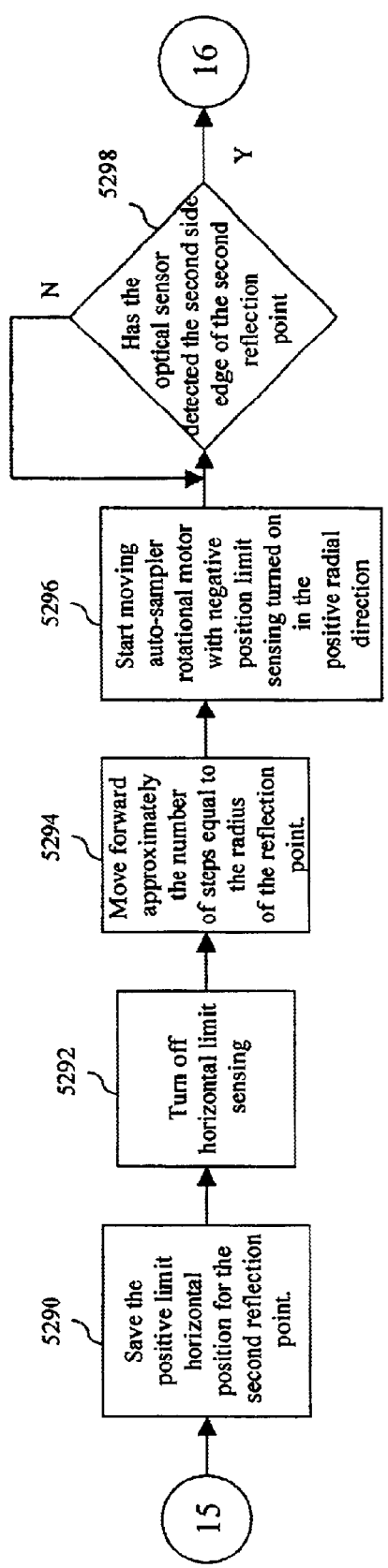
Figure 52P:
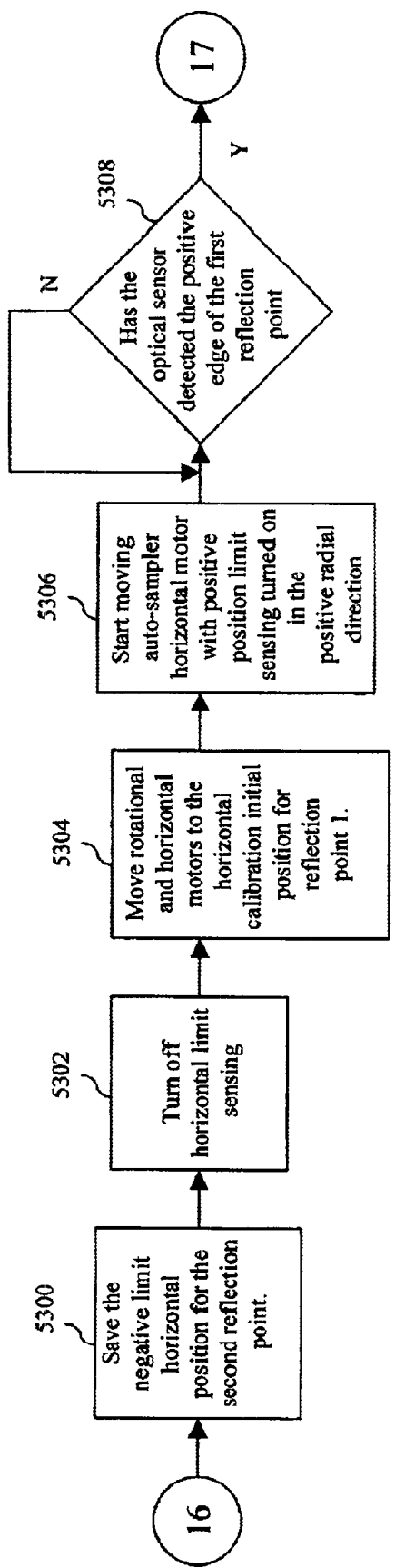
Figure 52Q:
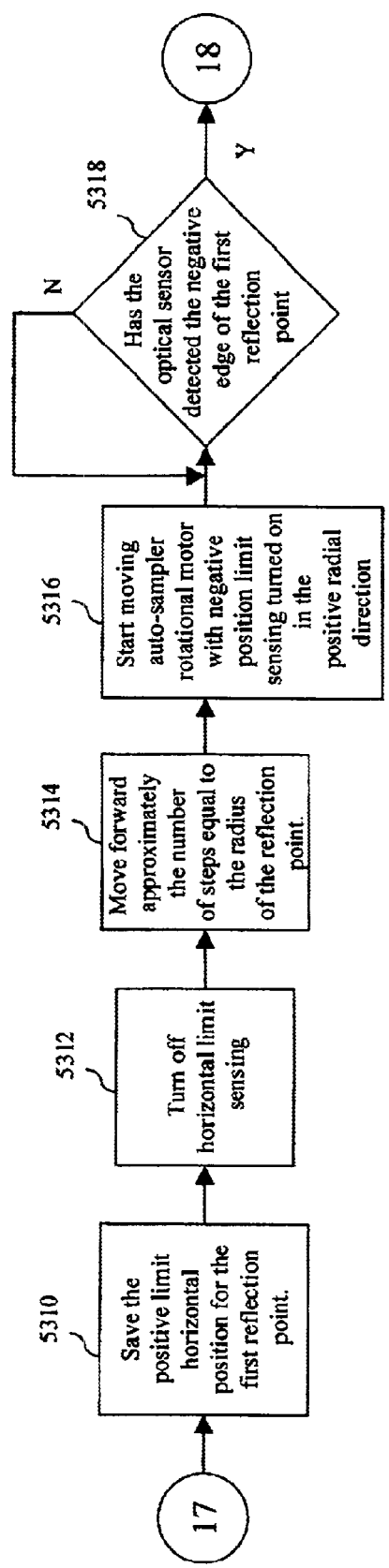
Figure 52R:
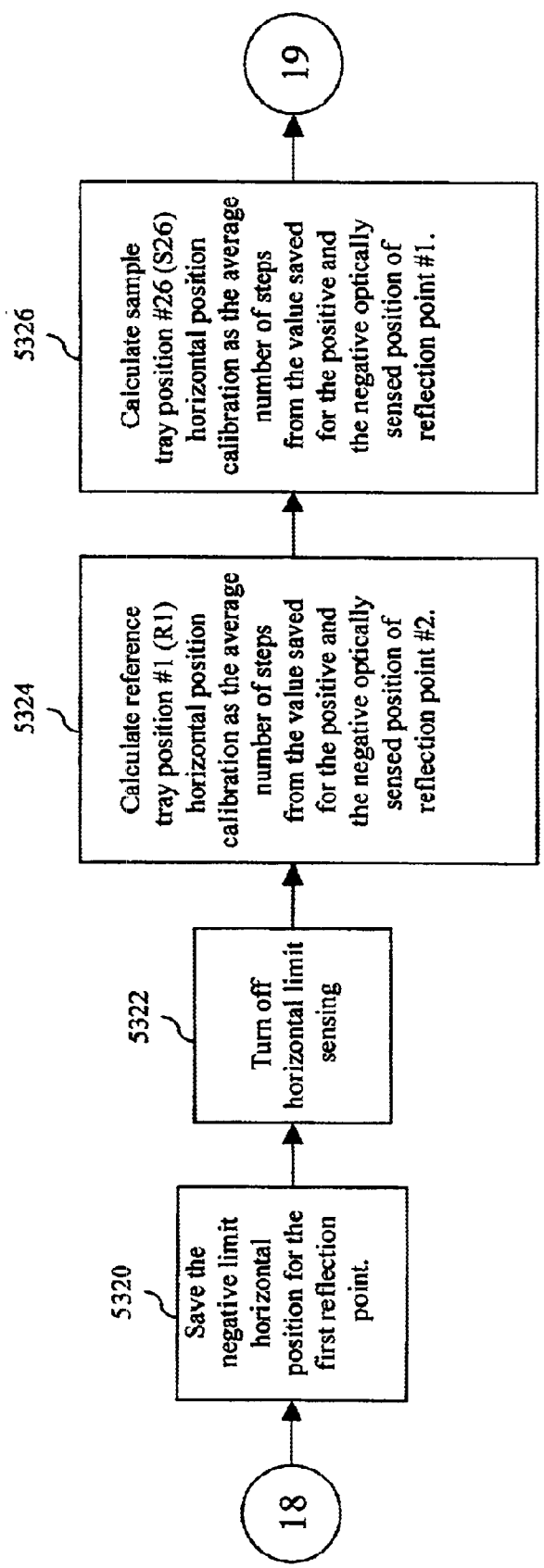
Figure 52S:
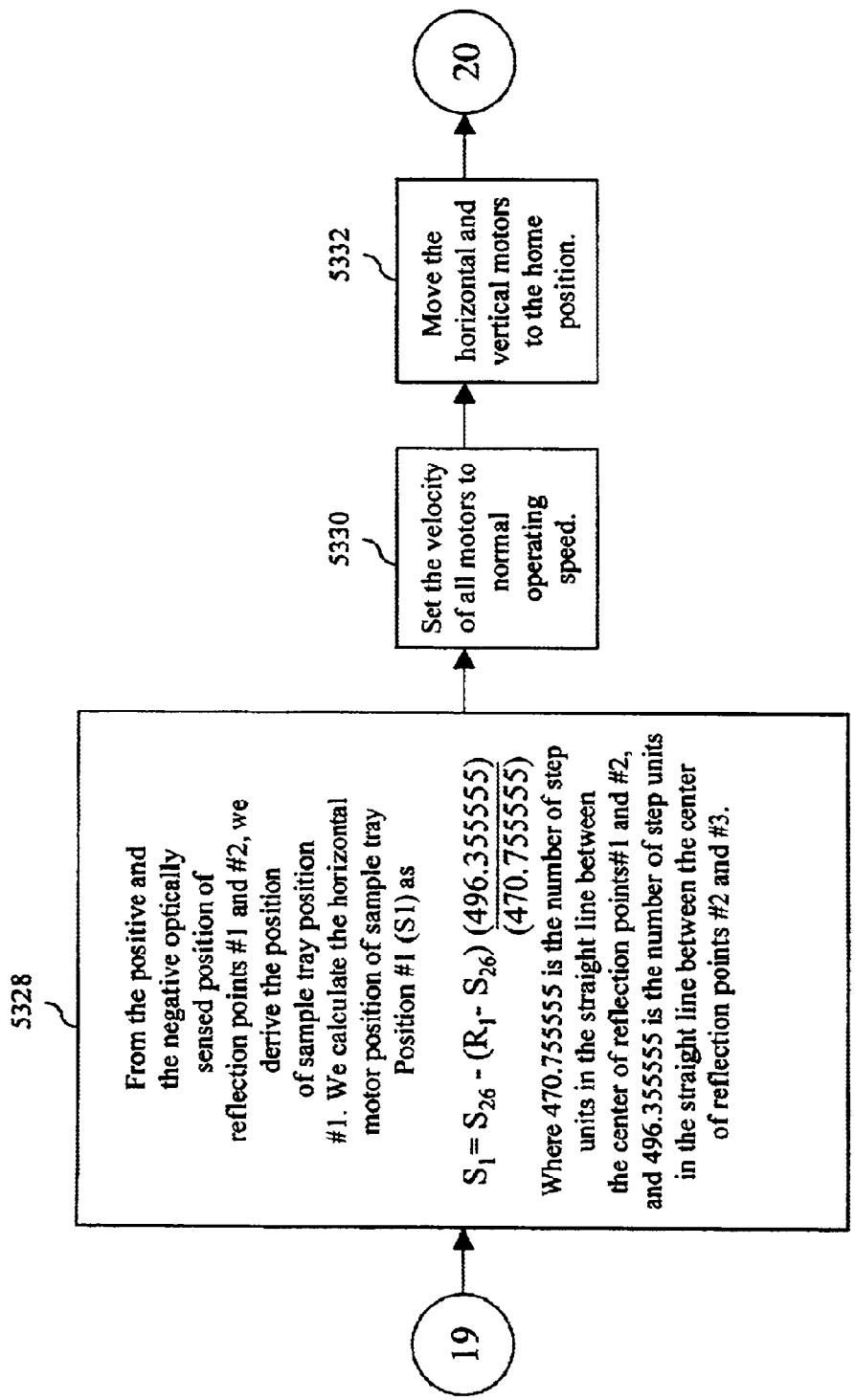
Figure 52T:
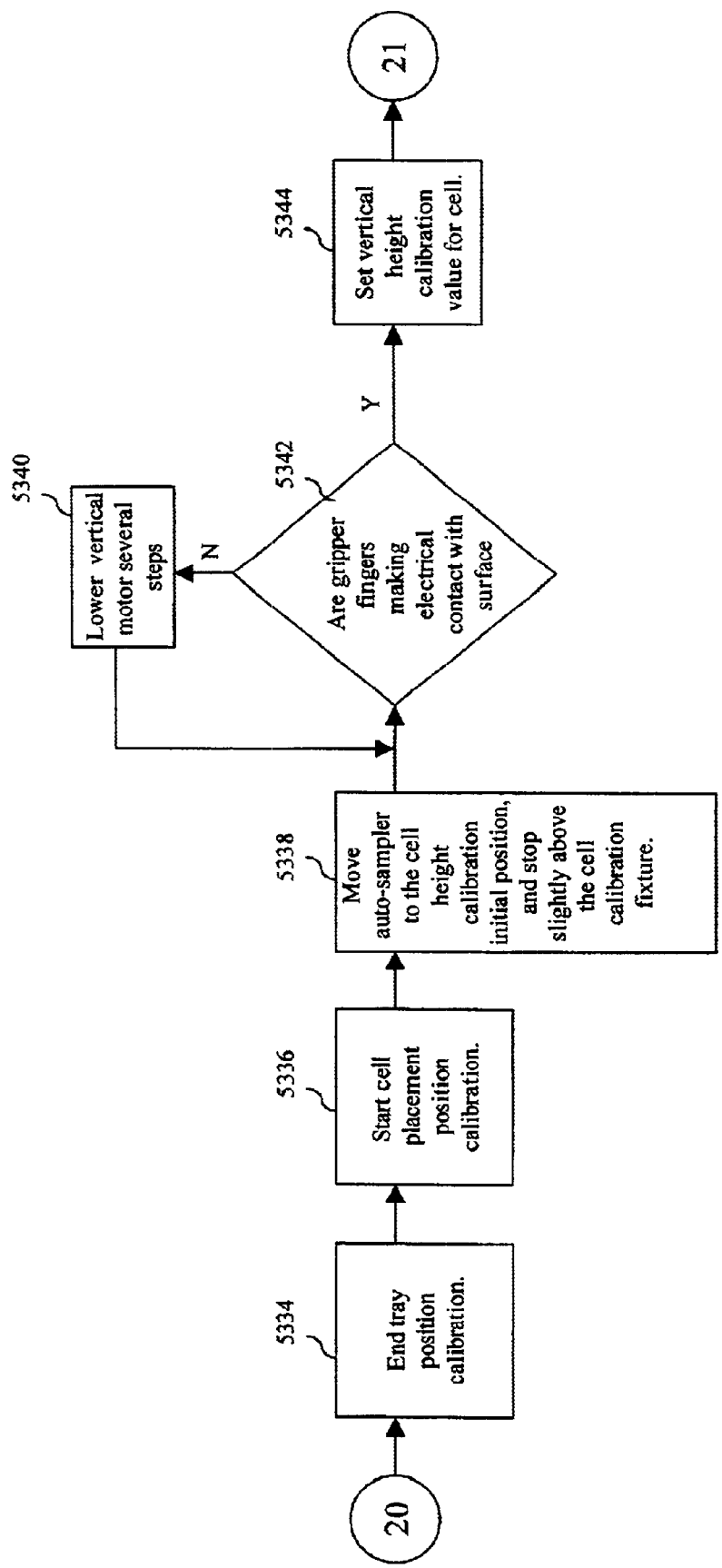
Figure 52U:
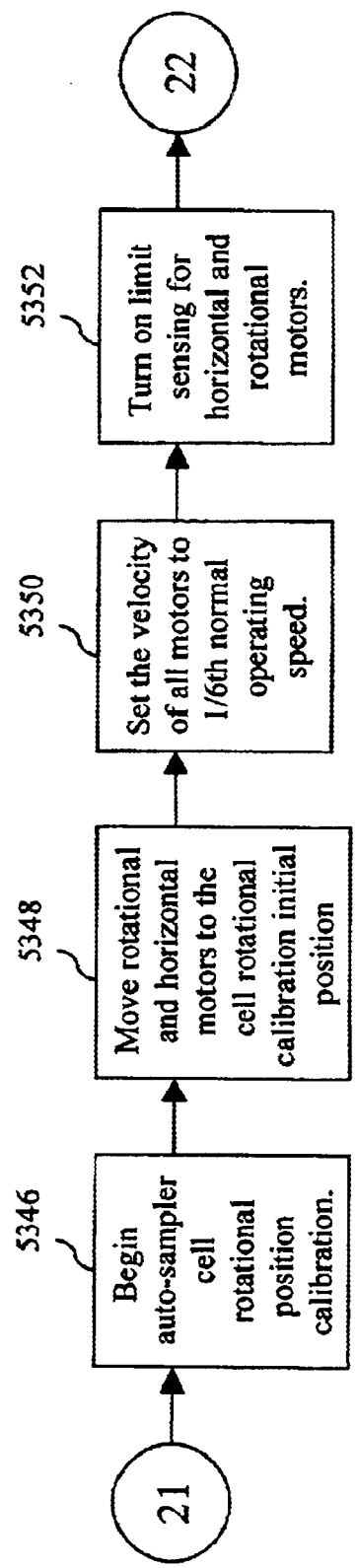

Referring to FIG. 54 and FIG. 52G, the procedure begins by sample arm 125 being raised from contact area 1660 and rotated until it is disposed at a position 5403 that is circumferentially clockwise from the first reflective surface 1645. This is the preferred initial position referred to in step 5246.

As discussed above, sample arm fiber optical sensor 1000 projects a beam of light towards moving table 220. An optical sensing calibration algorithm, which may reside in fiber optic amplifier 798 or control electronics module 235 (shown in FIG. 2), is configured to treat the non-reflective finish (for example, a black anodized finish) of moving table 220 as a low state and the reflective areas (for example, mirrors 1645, 1650, and 1655) as a high state.

As sample arm 125 is rotated along a common arc 5404 (in an exemplary embodiment, the radius of the arc is approximately 6.5 inches) in a counterclockwise fashion, starting at a point 5403 circumferentially clockwise from first reflective surface 1645. The system detects changes from the low state to the high state as the beam of light intersects the leading edge 5406 of the first reflective surface. This process is also shown in steps 5256 and 5258 in FIG. 52G. After the first leading edge 5406 has been detected, the position is saved in step 5260. The rotational limit sensing is then turned off in step 5262 so that optical sensor 810 can proceed over the first leading edge 5406 a distance equal to the radius of a reflection point. This is done in step 5264.

Optical sensor 810 on gripping device 710 is now ready to proceed over the first reflective surface and detect the trailing edge 5408 (see FIG. 55) of the first reflective surface 1645. This process is shown in steps 5266 and 5268 in FIG. 52H. Because optical sensor 810 is traversing over a reflective region, the system turns on the negative position limit sensing feature in step 5266. In other words, the system is looking for a transition from a high state to a low state, as the beam of light intersects the trailing edge 5408 of the first reflective surface 1645. Once the system detects the transition, in step 5268, the system preferably stores the value in step 5270.

The system can record the angular position of the first reflective surface in any number of suitable ways. One method is to record the angular position is to associate the angular position with the angle of the sample arm 125. Preferably, the angular position is recorded in micro-steps. A micro-step being a step of stepper motor 430 that rotates sample arm 125. Preferably, the angular positions of the leading edge 5406 and the trailing edge 5408 of the first reflective surface 1645 is recorded in terms of micro-steps.

As was done above, since the optical sensor is at a transitional region, the rotational limit sensing is turned off in step 5272, and is bumped forward a small amount so that the optical sensor can clear the transition point. This is done in step 5274. Preferably, the small amount is substantially equal to the radius of a reflection point. After the optical sensor has been bumped forward a suitable distance from the last transition, it proceeds along arc 5404 and looks for the leading edge 5410 of the second reflecting point 1650.

Sample arm 125 continues its rotation to second mirror 1650, again detecting the leading and trailing edge and recording the micro-step position of sample arm 125 at each edge. This process is similar to the process discussed above in connection with the detection of the leading and trailing edges of the first reflective surface 1645. This process is also disclosed in steps 5276–5294. The procedure is repeated for third mirror 1655. This process is disclosed in steps 5296–5272. After the system has recorded the angular position for the three reflective surfaces, the system then calculates the sample tray positions. This is shown in steps 5274, 5276 and 5278 in FIG. 52M.

Recall that the first reflective surface 1645 corresponds with well #26 and the second reflective surface corresponds to well #R1. Tray position #1 disposed radially outward of the outer periphery of moving table 220 and no reflective surface corresponds to its location. Therefore, the position of well #1 is determined by calculating its position, given the positions of well #26 and well #R1. There are many different ways the position of well #1 can be calculated. However, the equation shown in step 5278 is preferred. After the position of well #1 has been determined, the rotational position calibration is ended in step 5280. The system is now ready to determine the relative radial position of the reflective surfaces and gripper 710, as shown in step 5282 (see FIG. 52N).

The relative radial position of the reflective surfaces and the gripper 710 can be determined in many different ways. Preferably, sample arm 125 rotates to place gripper device 710 over one of the reflective surfaces. Any of the reflective surfaces could be selected, however, the second reflective surface 1650 is preferred. This is shown in step 5284 (see FIG. 52N). The center of reflective surface 1650 is calculated by using information previously obtained related to the leading edge 5410 and trailing edge 5412 of reflective surface 1650.

Once at the nominal center of reflective surface 1650, linear actuator motor 780 (FIG. 7B) of sample arm 125 is now used to retract gripper device 710 in a radial direction, that is, in a direction towards the sample arm axis 5402, past a first side edge 5414 of reflective surface 1650. The system records the radial position of the first side edge 5414. Next, gripper device 710 is extended in a radial direction past a second side edge 5416. The system also records the radial position of the second side edge 5416 by detecting the transitions in the reflected light received by optical sensor 810.

The radial calibration procedure can be terminated after the first and second side edges of one of the reflecting portions has been completed. To improve the accuracy of the radial calibration, the side edges of additional reflecting portions can also be determined. Preferably, the side edges of two reflecting portions are determined. In order to perform the radial calibration on a second reflecting portion, sample arm 125 is rotated in another reflecting portion. Preferably, sample arm 125 is rotated in a clockwise direction to first mirror 1645. In a manner similar to the sensing of the first side edge 5414 and second side edge 5416 of reflecting portion 1650, sample arm is retracted and extended in a radial direction to detect the first side edge 5420 and second side edge 5422 of first mirror 1645. The radial positions of the first mirror 1645 are recorded. Sample arm 125 could be rotated to detect the front and back edges of third mirror 1655, although radial detection of the side edges of the first two mirrors is generally sufficient.

Using the recorded positions for leading and trailing edges (for example, positions in θ in the cylindrical coordinate system) and side edges (for example, positions in R in the cylindrical coordinate system), the centers for the mirror can be determined. Because the moving table 220 and tray 1300 are designed so that representative wells, preferably, well #26, and reference well #1 are directly above mirrors 1645 and 1650, respectively, the centers of those wells correspond to the centers their respective mirrors.

The coordinate values are stored and the horizontal calibration for sample tray 1300 is complete. When other wells are to be accessed by sample arm 125, sample tray 1300 is rotated a fixed number of micro-steps relative to the stored coordinate pairs to locate the selected well. Thus, position values do not have to be stored for each well in sample tray 1300.

It is also noted that the calibration procedure may be accompanied by checking the home positions of the various motors in autosampler 100. For example, the rotational home position of sample arm 125 may be checked using home sensor 420 (FIG. 4C). The longitudinal home position of sample arm 125 may be checked using home sensor 784 (FIG. 7B). According to one embodiment, home positions are checked prior to performing the above-described electrical-sensing and optical-sensing calibration procedures.

Calibration of DSC cell platforms informs the system of the position of sample platform 1510 and reference platform 1520 (see FIG. 41). Cell calibration is conducted using a cell calibration fixture 1800, depicted in FIG. 45, which is inserted into the measurement chamber of DSC cell 120. Calibration fixture 1800 includes a fixture body 1850 having a top surface 1860. Top surface 1860 includes a first aperture 1810 and second aperture 1820 into which first plug 1830 and second plug 1840 are inserted, respectively.

According to one embodiment, top surface 1860 is an electrically conductive surface that is also optically reflective. The top portions of first plug 1830 and second plug 1840 are non-reflective. In one embodiment, plugs 1830 and 1840 are made of foam or rubber.

Figure 46:
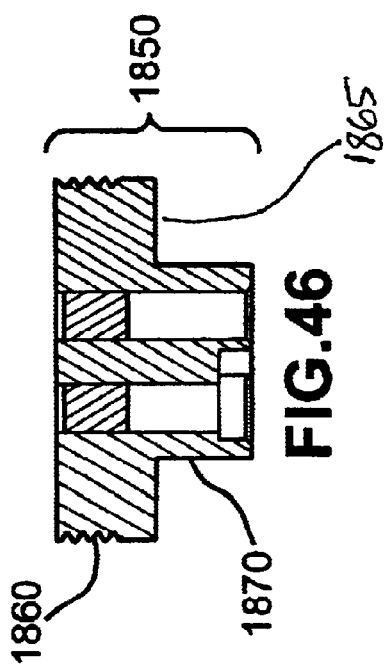
FIG. 46 is a cross-sectional view of a cell calibration member according to a preferred embodiment of the present invention.
Figure 48:
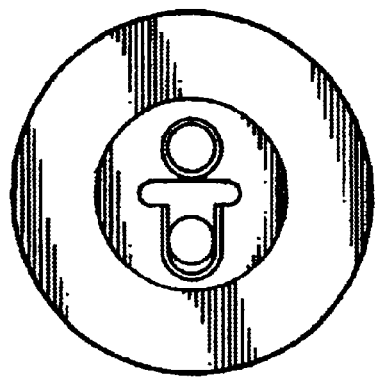
FIG. 48 is a top view of a cell calibration member according to a preferred embodiment of the present invention.
Figure 47:
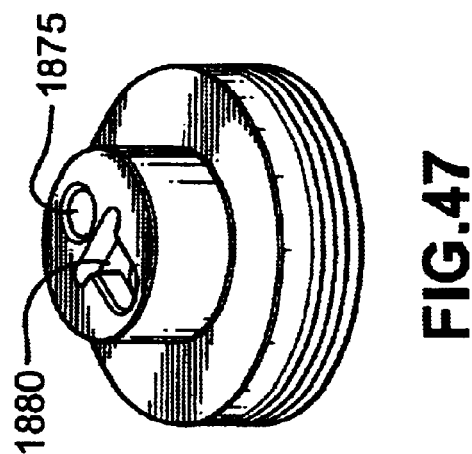
FIG. 47 is a bottom isometric view of a cell calibration member according to a preferred embodiment of the present invention.

Turning to FIG. 46, cell calibration fixture 1800 has a wide end 1860 and a narrow end 1870 separated by shoulder 1865. Shoulder 1865 rests on the top surface 1505 (See FIG. 41) of DSC cell 120. Turning to FIG. 47, cell calibration fixture 1800 includes circular hole 1875 extending through the fixture and a T-shaped recess 1880 intersecting another hole extending through the fixture. When cell calibration fixture 1800 is inserted into the DSC measurement chamber, hole 1875 and recess 1880 will engage the two platforms. A bottom view of cell calibration fixture 1800 is provided in FIG. 48.

Once inserted into DSC cell 120, cell calibration fixture 1800 can be used to calibrate the position of the cell platforms in three dimensions. Beginning with calibration using the electrical sensor in gripper device 710 (see FIG. 11), the sample arm 125 is rotated until the gripper device is located over DSC cell 120. Next, conductive fingers 730 are lowered by sample arm 125 to contact the conductive top surface 1860. When conductive top surface 1860 is detected, the platform height can be computed based on the vertical position of sample arm 125. In other words, the distance between the top surface 1860 of calibration fixture 1800 and the platforms is known. So, once the vertical position of sample arm 125 when it makes contact with the top surface 1860 of calibration fixture 1800 is known, then the system can easily compute the relative height of the platforms. Specifically, control electronics module 235 computes how deep into DSC cell 120 the gripper device 710 should travel in order to place and retrieve sample pans. The value is stored and the vertical calibration for DSC cell 120 is complete.

The height calibration for DSC cell 120 is performed during each auto-calibration. According to an embodiment, during auto-calibration the electrically-sensed height computation is performed prior to the optically-sensed horizontal position computation of DSC cell 120. This process is also shown as a flow diagram in steps 5336–5344 (see FIG. 52T).

The horizontal position calibration for DSC cell 120 is similar to that performed for sample tray 1300, as previously described. When installed, plug 1830 and plug 1840 are located over sample platform 1510 and reference platform 1520. The platforms and, therefore, the plugs, are located along the common arc of rotation 5404 (see FIGS. 54 and 55).

Turning to FIGS. 54 and 55, sample arm 125 is rotated until it is at position 5502, slightly circumferentially counterclockwise of second plug 1840. Sample arm fiber optic sensor 1000 projects a beam of light. As sample arm 125 is rotated counterclockwise along common arc 5404, the optical sensing calibration algorithm detects the transitions from the high state (reflective) to the low state (non-reflective), and then the low state to the high state, as the beam of light intersects the leading 5504 and trailing edge 5506 of second plug 1840. The rotational position, preferably measured in micro-steps, of sample arm 125 is recorded at each of these points.

Next, sample arm 125 continues its rotation to first plug 1830, again detecting the leading 5508 and trailing edge 5510 and recording the micro-position of sample arm 125 at each edge.

The distance R computation commences as rotating sample arm 125 rotates to the nominal center of one of the plugs, e.g., first plug 1830. Sample arm 125 is now engaged by linear actuator motor 780 (FIG. 7B) to retract gripper device 710 in a radial or longitudinal direction past the first side edge 5512 of first plug 1830 edge. Next, gripper device 710 is extended in a radial direction past the second side 5514 edge of plug 1830. The micro-positions corresponding to these positions are recorded. Sample arm 125 is now rotated to second plug 1840, the procedure of determining the first and second side edges of second plug 1840 is repeated, and the micro-positions are recorded.

Using the recorded micro-positions for leading and trailing edges (e.g., positions in θ) and front and back edges (e.g., positions in R), the centers of sample platform 1510 and reference platform 1520 can be computed. The coordinate values are stored and the horizontal calibration for DSC cell 120 is complete.

Figure 52V:
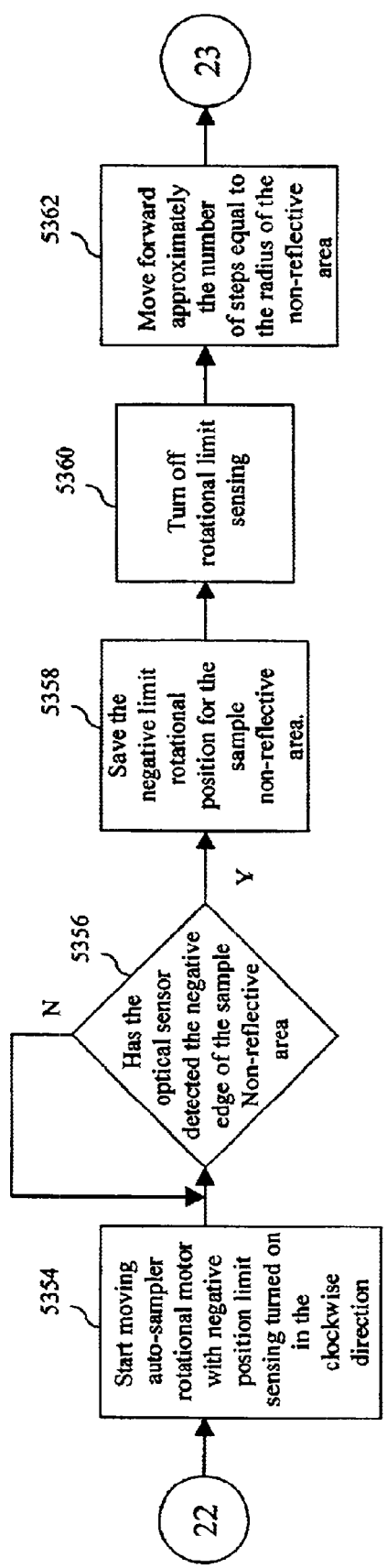
Figure 52W:
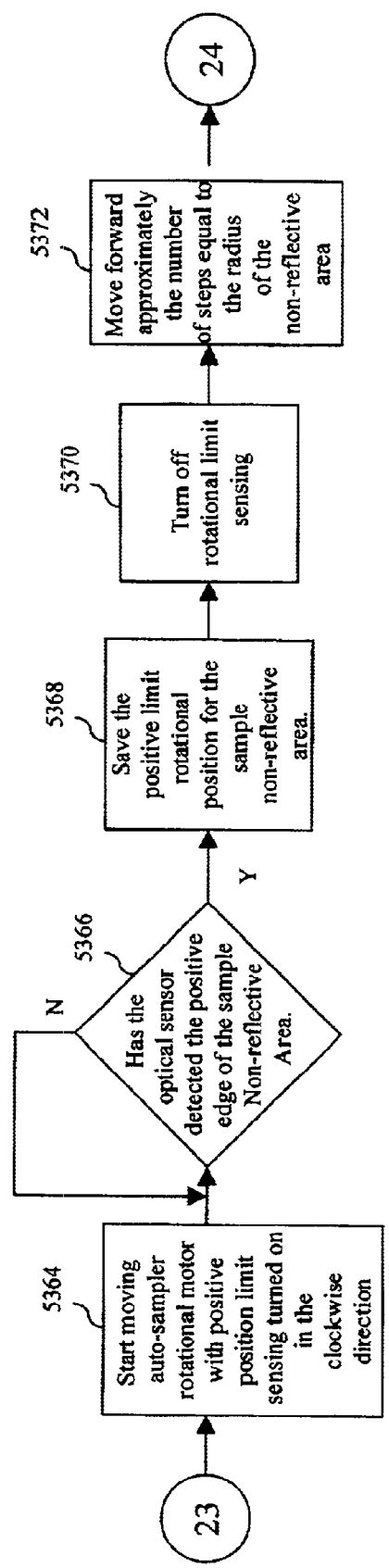
Figure 52X:
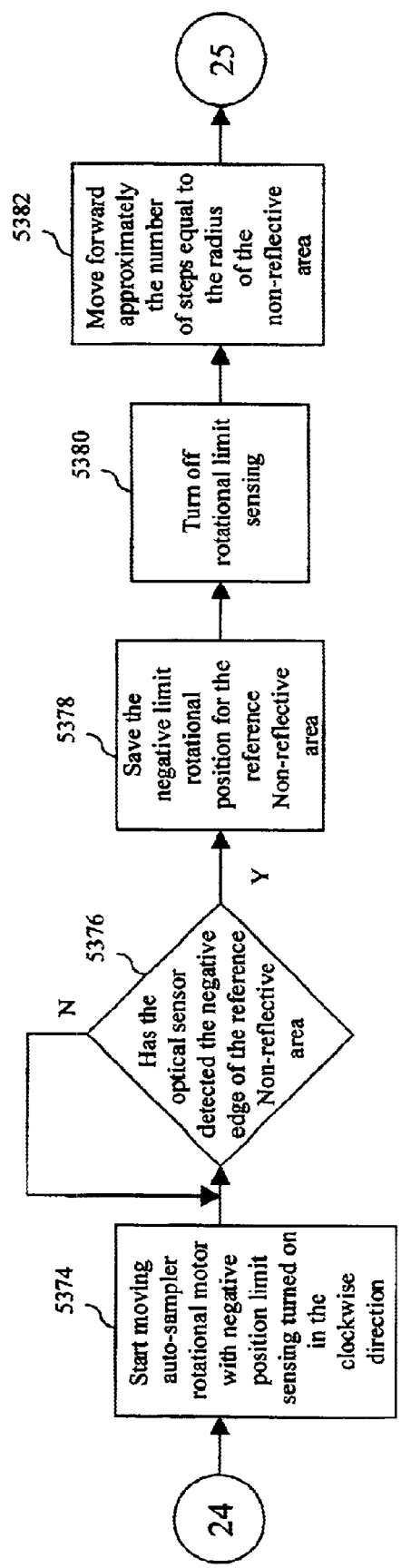
Figure 52Y:
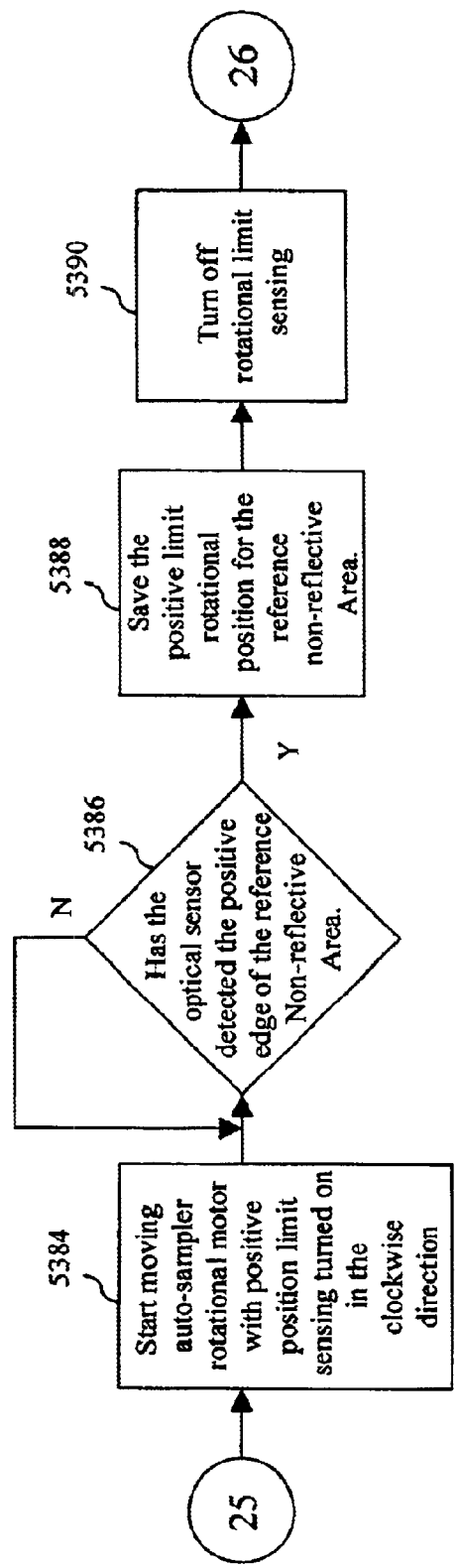
Figure 52Z:
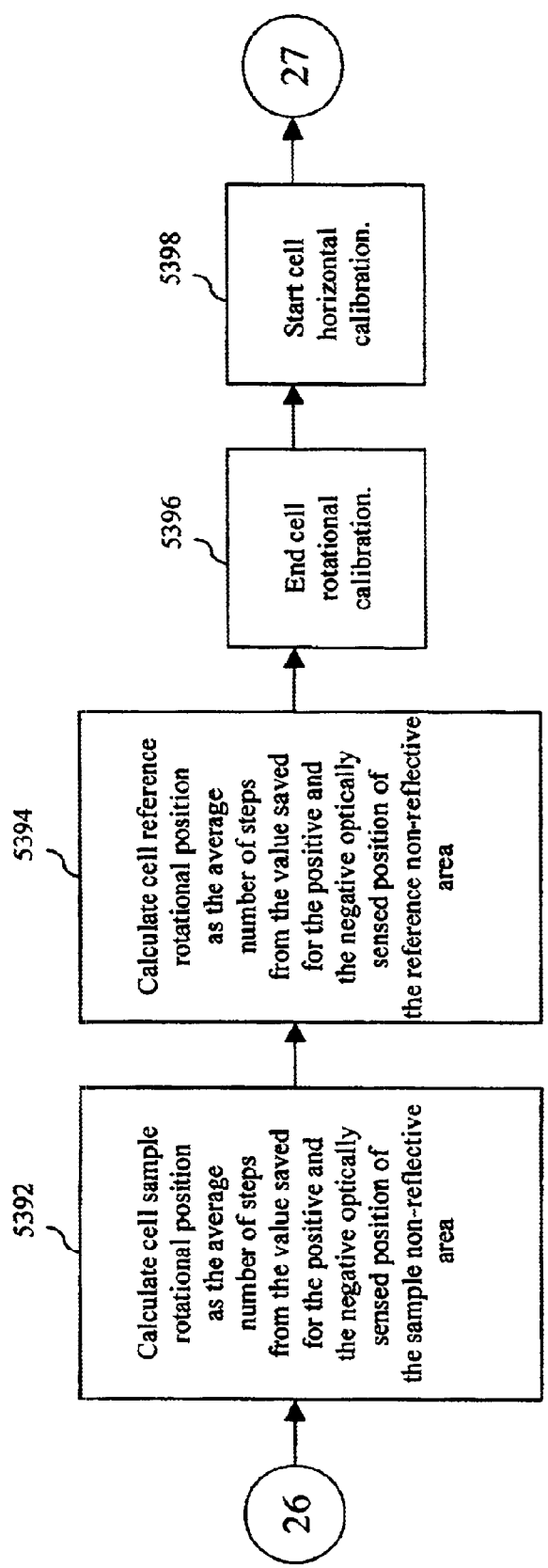
Figure 52A:
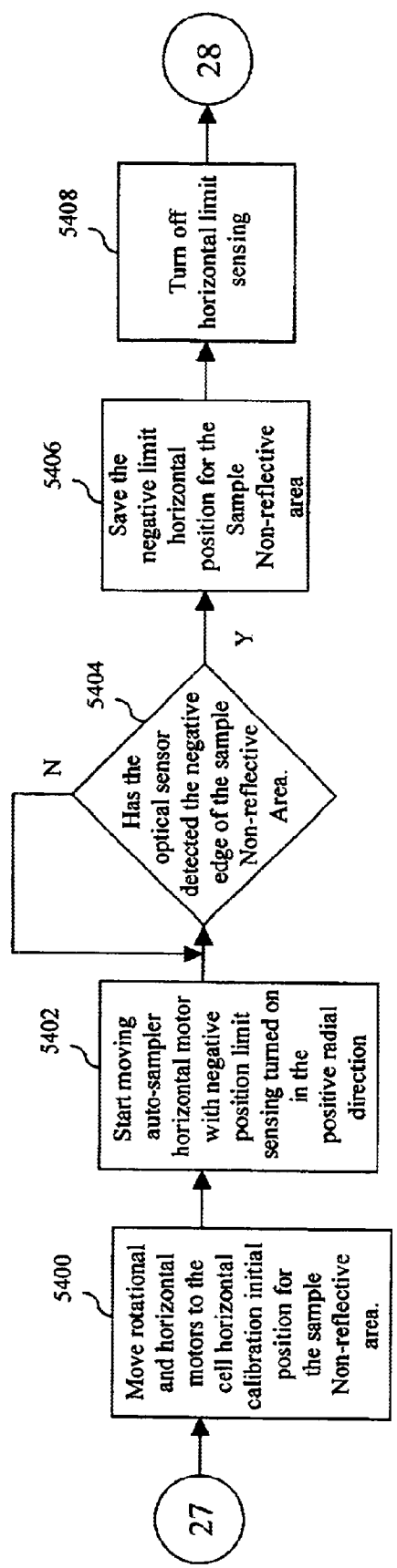
Figure 52A:
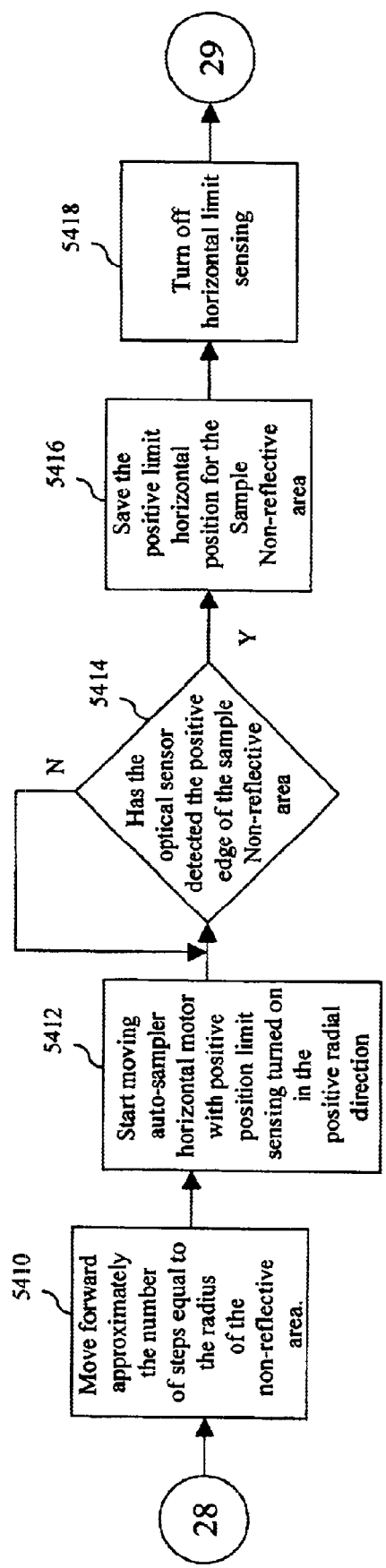
Figure 52A:
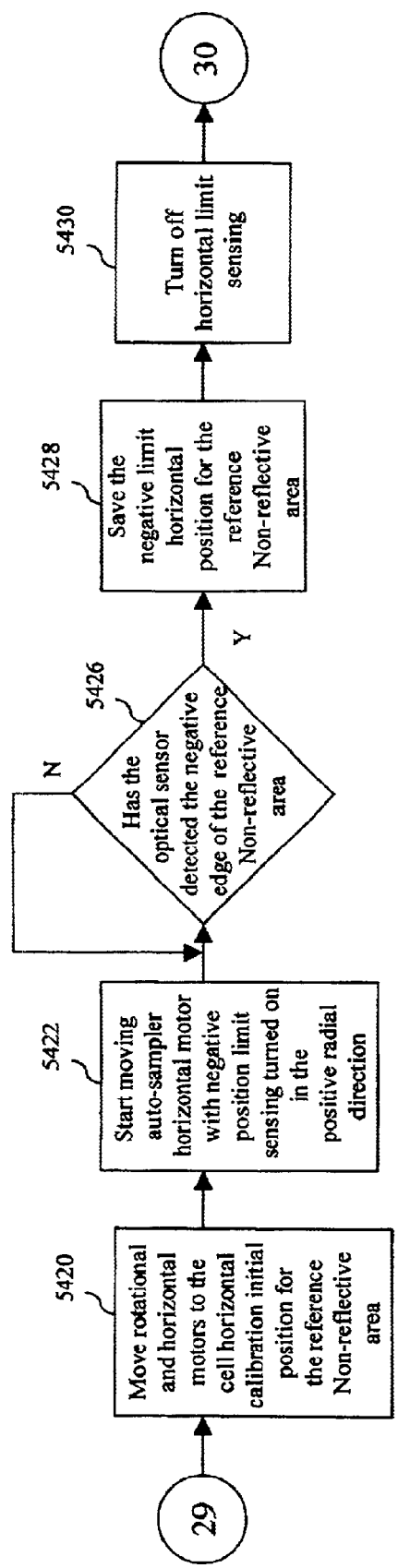
Figure 52A:
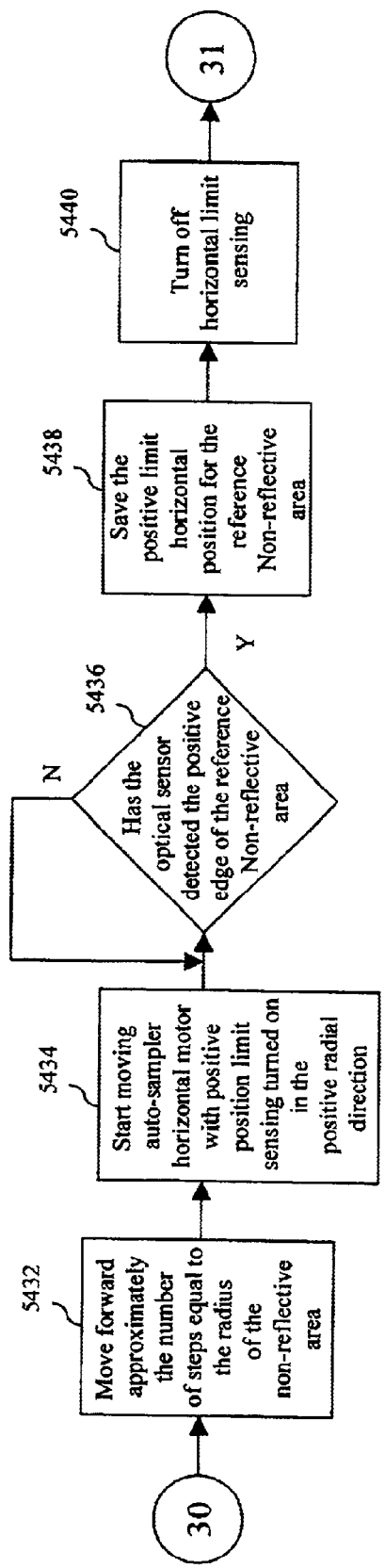
Figure 52A:
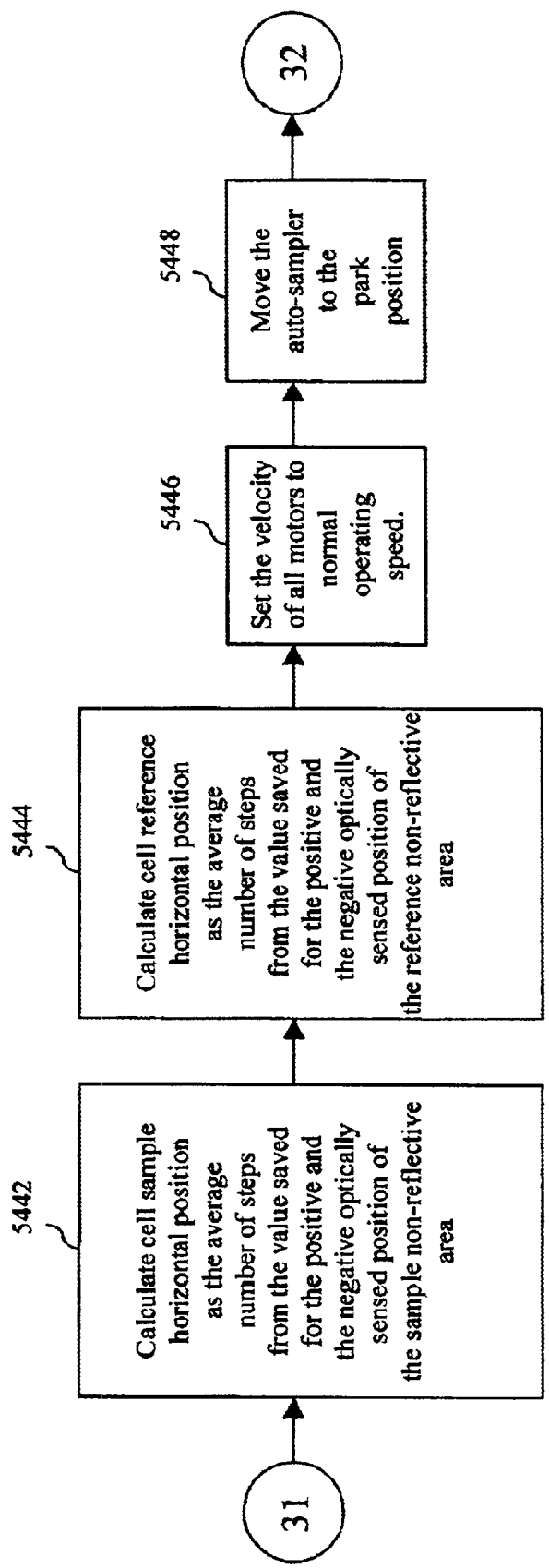
Figure 52A:
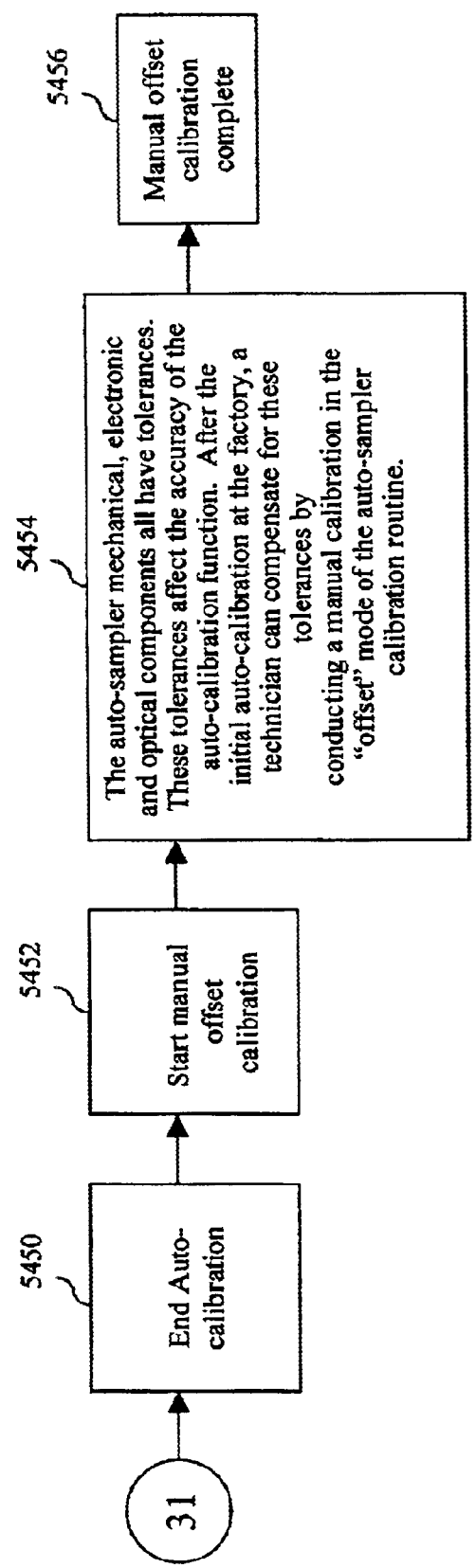

An exemplary embodiment of the calibration procedure disclosed in connection with the DSC cell 120 is shown in steps 5354–5450 (See FIGS. 52V-52AF). Steps 5354–5450 use a different method, one that is more suitable to computer implementation, of referring to the various physical elements. For example, in step 5354, the step states, "Start moving auto-sampler rotational motor with negative position limit sensing turned on in the clockwise direction." In step 5356, the procedure checks to see if a "negative edge" has been detected. What is meant by "negative edge" in both these steps is leading edge 5504 of second plug 1840. The procedure disclosed in FIGS. 52A-52AV calls one of the circumferential edges the "negative edge" and calls the other circumferential edge (trailing edge 5506 in the embodiment shown in FIG. 55B) the "positive edge." The same is true for the first and second side edges. The procedure disclosed in FIGS. 52A-52AF refers to the first side edge as the "negative edge," (see, for example, steps 5402 and 5404 (See FIG. 52AA)), and the second side edge as the "positive edge." (See, for example, 5412 and 5414 (See FIG. 52AB)). This applies to all FIGS. 52A-52AF.

The procedure disclosed in FIGS. 52A-52AF also mentions statements like "Start moving auto-sampler horizontal motor with positive position limit sensing turned on." (See, for example, step 5414 (FIG. 52AB)). This statement means that the system is trying to sense the positive position limit. In other words, the system is trying to sense a transition. This applies to all FIGS. 52A-52AF.

The "negative position" and the "positive position" are simply a naming convention used in the procedure disclosed in FIGS. 52A-52AF.

There are a number of advantages to the above-described cell calibration procedure. One beneficial aspect of the height calibration is that it can be used to recalibrate auto-sampler 100 for DSC cells of different sizes. For example, if a user replaces the DSC cell with one of a different size, the auto-calibration procedure can be used to recalibrate the sample arm 125 to the new cell height. Additionally, it is not uncommon for the position of DSC cell 120 to change when the cooling device or other components are installed or removed. The cell calibration procedure can be undertaken to account for such changes in the position of DSC cell 120 relative to sample arm 125.

It is to be understood that the sequence of operations described above in calibrating DSC cell 120 is exemplary only. The plug positions could be calculated in reverse order. The sequence of angular and radial detection could be reversed. Additionally, the auto-calibration procedure could have several options: complete auto-calibration (sample tray and DSC cell); sample tray only; or DSC cell only. According to one embodiment, the user would select from these various options using touch screen display and control 130 of FIG. 2.

According to another embodiment, the auto-calibration results can be further optimized using a stored set of offset coefficients. The various components of auto-sampler 100 have tolerances and/or biases. There are optical tolerances associated with optic lenses, optical cables, optical amplifiers, and so forth. There are mechanical tolerances associated with the mechanical parts of auto-sampler 100. There are electrical tolerances associated with electrical sensors and other electronic components.

According to this embodiment, an auto-calibration can be performed to calibrate sample tray 1300 (e.g., the positions of sample well #1, sample well #26, and reference #1) and DSC cell 120 (e.g., sample platform 1510 and reference platform 1520). A user, such as a technician, then enters an "offset mode" option using touchscreen display 130. Using touchscreen display 130, the user can then manually control the position of gripper device 710 to calibrate each of the above positions by eye. For each position, the difference between the user-controlled calibration and the auto-calibration result is stored as an offset coefficient. These offset coefficients are stored (e.g., by control electronics module 235 of FIG. 2) and applied to subsequent auto-calibrations to render a more accurate, "hand tuned" result.

By using the offset coefficients, the auto-calibration procedure provides a calibration result that is substantially automated and that is quick, but that also approaches the accuracy of a so-called "eyeball-correct," manual calibration.

The preferred embodiment can also include a "customer mode" where unauthorized personnel are not permitted to modify the offset coefficients. However, even in "customer mode," the customer can manually override and adjust any auto-calibrated tray or cell position.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A table for calibrating positions, comprising:

a surface;

an electrically-responsive area; and at least one optically-responsive area, wherein the electrically-responsive area and the at least one optically-responsive area can be detected to calibrate a position, wherein the electrically-responsive area comprises a conductive area, wherein the at least one optically-responsive area comprises at least one reflective area, wherein the at least one reflective area comprises a plurality of mirrors for calibrating the positions of wells in a sample tray, and wherein the at least one reflective area comprises a number of mirrors sufficient to calibrate each row of wells in the sample tray.

2. The table of claim 1, wherein the rows of wells are concentrically disposed on the sample tray.

3. The table of claim 1, wherein the rows of wells are linearly disposed on the sample tray.

4. The table of claim 1, further comprising a plurality of location members for locating the sample tray onto the table.

5. The table of claim 4, wherein the table has a circular shape and the location members are located around the circumference of the table.

6. The table of claim 5, further comprising a lip around the circumference of the table for locating the sample tray onto the table.

* * * * *